US010030258B2

(12) United States Patent
Kim et al.

(10) Patent No.: US 10,030,258 B2
(45) Date of Patent: *Jul. 24, 2018

(54) MICROORGANISM COMPRISING GENE FOR CODING ENZYME INVOLVED IN PRODUCING RETINOID AND METHOD FOR PRODUCING RETINOID BY USING SAME

(71) Applicant: INDUSTRY-ACADEMIC COOPERATION FOUNDATION GYEONGSANG NATIONAL UNIVERSITY, Gyeongsangnam-do (KR)

(72) Inventors: Seon-Won Kim, Gyeongsangnam-do (KR); Hui-Jeong Jang, Gyeongsangnam-do (KR); Hyeon-Seo Lee, Gyeongsangnam-do (KR); Sang-Hwal Yoon, Gyeongsangnam-do (KR)

(73) Assignee: Industrial-Academic Cooperation Foundation Gyeongsang National University, Gyeongsangnam-do (KR)

( * ) Notice: Subject to any disclaimer, the term of this patent is extended or adjusted under 35 U.S.C. 154(b) by 143 days.

This patent is subject to a terminal disclaimer.

(21) Appl. No.: 14/900,303

(22) PCT Filed: Oct. 28, 2013

(86) PCT No.: PCT/KR2013/009643
§ 371 (c)(1),
(2) Date: Dec. 21, 2015

(87) PCT Pub. No.: WO2014/204058
PCT Pub. Date: Dec. 24, 2014

(65) Prior Publication Data
US 2016/0130628 A1 May 12, 2016

(30) Foreign Application Priority Data
Jun. 20, 2013 (KR) ........................ 10-2013-0071130

(51) Int. Cl.
C12P 23/00 (2006.01)
C12R 1/865 (2006.01)
C12R 1/15 (2006.01)

(52) U.S. Cl.
CPC ............... *C12P 23/00* (2013.01); *C12R 1/15* (2013.01); *C12R 1/865* (2013.01)

(58) Field of Classification Search
None
See application file for complete search history.

(56) References Cited

U.S. PATENT DOCUMENTS

| 9,644,217 B2 * | 5/2017 | Kim ........................ C12P 7/24 |
| 2006/0228785 A1 | 10/2006 | Hoshino et al. |
| 2007/0161093 A1 | 7/2007 | Hoshino et al. |

FOREIGN PATENT DOCUMENTS

| CN | 1914326 A | 2/2007 |
| KR | 10-1137026 B1 | 4/2012 |
| KR | 10-2013-0014445 A | 2/2013 |
| WO | 2013-019051 A2 | 2/2013 |

OTHER PUBLICATIONS

Office action dated Jun. 27, 2016 from Korea Intellectual Property Office in a counterpart Korea Patent Application No. 10-2013-0071130.
Office action dated Jun. 13, 2017 from China Patent Office in a counterpart China Patent Application No. 201380077601.6.
Sabine A E Heider et al., "Carotenoid biosynthesis and overproduction in Corynebacterium glutamicum", BMC Microbiology vol. 12, No. 198, 2012.
International Search Report for PCT/KR2013/009643.
Moon, Min-Woo et al., "Analyses of enzyme II gene mutants for sugar transport and heterologous expression of fructokinase gene in Corynebacterium glutamicum ATCC 13032", FEMS Microbiology Letters, Mar. 15, 2005, vol. 244, No. 2, pp. 259-266.
NCBI, Genbank accession No. CAE26954.1, Apr. 17, 2005.
NCBI, Genbank accession No. YP_001436481.1, Jun. 10, 2013.
NCBI, Genbank accession No. NP_013636, Feb. 25, 2013.
NCBI, Genbank accession No. NP_601108.1, Jun. 10, 2013.
NCBI, Genbank accession No. WP_002357756.1, May 12, 2013.

* cited by examiner

*Primary Examiner* — Kagnew H Gebreyesus
(74) *Attorney, Agent, or Firm* — The PL Law Group, PLLC

(57) ABSTRACT

The present invention relates to a microorganism comprising a gene for coding an enzyme involved in producing retinoid and a method for producing retinoid by using the same, and more specifically, to: a microorganism capable of mass-producing retinoid at a remarkable efficiency by comprising a gene for coding an enzyme involved in producing retinoid; and a method for producing retinoid by using the same.

16 Claims, 5 Drawing Sheets

(A) RETINOL STANDARD COMPOUND (B) RETINOL PRODUCED IN YEAST (C) RETINYL ACETATE STANDARD COMPOUND (D) RETINYL ACETATE PRODUCED IN YEAST

SEQUENCE LISTING

<160> NUMBER OF SEQ ID NOS: 94

<210> SEQ ID NO 1
<211> LENGTH: 525
<212> TYPE: PRT
<213> ORGANISM: Saccharomyces cerevisiae

<400> SEQUENCE: 1

Met Asp Gln Leu Val Lys Thr Glu Val Thr Lys Lys Ser Phe Thr Ala
1               5                   10                  15

Pro Val Gln Lys Ala Ser Thr Pro Val Leu Thr Asn Lys Thr Val Ile
            20                  25                  30

Ser Gly Ser Lys Val Lys Ser Leu Ser Ser Ala Gln Ser Ser Ser Ser
        35                  40                  45

Gly Pro Ser Ser Ser Ser Glu Glu Asp Asp Ser Arg Asp Ile Glu Ser
    50                  55                  60

Leu Asp Lys Lys Ile Arg Pro Leu Glu Glu Leu Glu Ala Leu Leu Ser
65                  70                  75                  80

Ser Gly Asn Thr Lys Gln Leu Lys Asn Lys Glu Val Ala Ala Leu Val
                85                  90                  95

Ile His Gly Lys Leu Pro Leu Tyr Ala Leu Glu Lys Lys Leu Gly Asp
            100                 105                 110

Thr Thr Arg Ala Val Ala Val Arg Arg Lys Ala Leu Ser Ile Leu Ala
        115                 120                 125

Glu Ala Pro Val Leu Ala Ser Asp Arg Leu Pro Tyr Lys Asn Tyr Asp
    130                 135                 140

Tyr Asp Arg Val Phe Gly Ala Cys Cys Glu Asn Val Ile Gly Tyr Met
145                 150                 155                 160

Pro Leu Pro Val Gly Val Ile Gly Pro Leu Val Ile Asp Gly Thr Ser
                165                 170                 175

Tyr His Ile Pro Met Ala Thr Thr Glu Gly Cys Leu Val Ala Ser Ala
            180                 185                 190

Met Arg Gly Cys Lys Ala Ile Asn Ala Gly Gly Gly Ala Thr Thr Val
        195                 200                 205

Leu Thr Lys Asp Gly Met Thr Arg Gly Pro Val Val Arg Phe Pro Thr
    210                 215                 220

Leu Lys Arg Ser Gly Ala Cys Lys Ile Trp Leu Asp Ser Glu Glu Gly
225                 230                 235                 240

Gln Asn Ala Ile Lys Lys Ala Phe Asn Ser Thr Ser Arg Phe Ala Arg
                245                 250                 255

Leu Gln His Ile Gln Thr Cys Leu Ala Gly Asp Leu Leu Phe Met Arg
            260                 265                 270

Phe Arg Thr Thr Thr Gly Asp Ala Met Gly Met Asn Met Ile Ser Lys
        275                 280                 285

Gly Val Glu Tyr Ser Leu Lys Gln Met Val Glu Glu Tyr Gly Trp Glu
    290                 295                 300

Asp Met Glu Val Val Ser Val Ser Gly Asn Tyr Cys Thr Asp Lys Lys
305                 310                 315                 320

Pro Ala Ala Ile Asn Trp Ile Glu Gly Arg Gly Lys Ser Val Val Ala
                325                 330                 335

Glu Ala Thr Ile Pro Gly Asp Val Val Arg Lys Val Leu Lys Ser Asp
            340                 345                 350

Val Ser Ala Leu Val Glu Leu Asn Ile Ala Lys Asn Leu Val Gly Ser
        355                 360                 365

-continued

Ala Met Ala Gly Ser Val Gly Gly Phe Asn Ala His Ala Ala Asn Leu
    370                 375                 380

Val Thr Ala Val Phe Leu Ala Leu Gly Gln Asp Pro Ala Gln Asn Val
385                 390                 395                 400

Glu Ser Ser Asn Cys Ile Thr Leu Met Lys Glu Val Asp Gly Asp Leu
                405                 410                 415

Arg Ile Ser Val Ser Met Pro Ser Ile Glu Val Gly Thr Ile Gly Gly
            420                 425                 430

Gly Thr Val Leu Glu Pro Gln Gly Ala Met Leu Asp Leu Leu Gly Val
        435                 440                 445

Arg Gly Pro His Ala Thr Ala Pro Gly Thr Asn Ala Arg Gln Leu Ala
    450                 455                 460

Arg Ile Val Ala Cys Ala Val Leu Ala Gly Glu Leu Ser Leu Cys Ala
465                 470                 475                 480

Ala Leu Ala Ala Gly His Leu Val Gln Ser His Met Thr His Asn Arg
                485                 490                 495

Lys Pro Ala Glu Pro Thr Lys Pro Asn Asn Leu Asp Ala Thr Asp Ile
            500                 505                 510

Asn Arg Leu Lys Asp Gly Ser Val Thr Cys Ile Lys Ser
        515                 520                 525

<210> SEQ ID NO 2
<211> LENGTH: 307
<212> TYPE: PRT
<213> ORGANISM: Pantoea agglomerans

<400> SEQUENCE: 2

Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
        35                  40                  45

Ala Pro Gly Lys Arg Ile Arg Pro Leu Leu Met Leu Leu Ala Ala Arg
    50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Ala Thr Gly Asp Leu Pro Gly Glu Arg
    130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175

Thr Pro Asp Ala Ile Leu Ser Thr Asn His Leu Lys Thr Gly Ile Leu
            180                 185                 190

Phe Ser Ala Met Leu Gln Ile Val Ala Ile Ala Ser Ala Ser Ser Pro
        195                 200                 205

Ser Thr Arg Glu Thr Leu His Ala Phe Ala Leu Asp Phe Gly Gln Ala
    210                 215                 220

```
Phe Gln Leu Leu Asp Asp Leu Arg Asp His Pro Glu Thr Gly Lys
225                 230                 235                 240

Asp Arg Asn Lys Asp Ala Gly Lys Ser Thr Leu Val Asn Arg Leu Gly
            245                 250                 255

Ala Asp Ala Ala Arg Gln Lys Leu Arg Glu His Ile Asp Ser Ala Asp
        260                 265                 270

Lys His Leu Thr Phe Ala Cys Pro Gln Gly Gly Ala Ile Arg Gln Phe
            275                 280                 285

Met His Leu Trp Phe Gly His His Leu Ala Asp Trp Ser Pro Val Met
        290                 295                 300

Lys Ile Ala
305
```

<210> SEQ ID NO 3
<211> LENGTH: 302
<212> TYPE: PRT
<213> ORGANISM: Synechocystis sp. PCC6803

<400> SEQUENCE: 3

```
Met Val Ala Gln Gln Thr Arg Thr Asp Phe Asp Leu Ala Gln Tyr Leu
1               5                   10                  15

Gln Val Lys Lys Gly Val Val Glu Ala Ala Leu Asp Ser Ser Leu Ala
            20                  25                  30

Ile Ala Arg Pro Glu Lys Ile Tyr Glu Ala Met Arg Tyr Ser Leu Leu
        35                  40                  45

Ala Gly Gly Lys Arg Leu Arg Pro Ile Leu Cys Ile Thr Ala Cys Glu
    50                  55                  60

Leu Cys Gly Gly Asp Glu Ala Leu Ala Leu Pro Thr Ala Cys Ala Leu
65                  70                  75                  80

Glu Met Ile His Thr Met Ser Leu Ile His Asp Asp Leu Pro Ser Met
                85                  90                  95

Asp Asn Asp Asp Phe Arg Arg Gly Lys Pro Thr Asn His Lys Val Tyr
            100                 105                 110

Gly Glu Asp Ile Ala Ile Leu Ala Gly Asp Gly Leu Leu Ala Tyr Ala
        115                 120                 125

Phe Glu Tyr Val Val Thr His Thr Pro Gln Ala Asp Pro Gln Ala Leu
    130                 135                 140

Leu Gln Val Ile Ala Arg Leu Gly Arg Thr Val Gly Ala Ala Gly Leu
145                 150                 155                 160

Val Gly Gly Gln Val Leu Asp Leu Glu Ser Glu Gly Arg Thr Asp Ile
                165                 170                 175

Thr Pro Glu Thr Leu Thr Phe Ile His Thr His Lys Thr Gly Ala Leu
            180                 185                 190

Leu Glu Ala Ser Val Leu Thr Gly Ala Ile Leu Ala Gly Ala Thr Gly
        195                 200                 205

Glu Gln Gln Gln Arg Leu Ala Arg Tyr Ala Gln Asn Ile Gly Leu Ala
    210                 215                 220

Phe Gln Val Val Asp Asp Ile Leu Asp Ile Thr Ala Thr Gln Glu Glu
225                 230                 235                 240

Leu Gly Lys Thr Ala Gly Lys Asp Val Lys Ala Gln Lys Ala Thr Tyr
                245                 250                 255

Pro Ser Leu Leu Gly Leu Glu Ala Ser Arg Ala Gln Ala Gln Ser Leu
            260                 265                 270

Ile Asp Gln Ala Ile Val Ala Leu Glu Pro Phe Gly Pro Ser Ala Glu
```

```
                275                 280                 285
Pro Leu Gln Ala Ile Ala Glu Tyr Ile Val Ala Arg Lys Tyr
    290                 295                 300

<210> SEQ ID NO 4
<211> LENGTH: 309
<212> TYPE: PRT
<213> ORGANISM: Pantoea agglomerans

<400> SEQUENCE: 4

Met Ser Gln Pro Pro Leu Leu Asp His Ala Thr Gln Thr Met Ala Asn
1               5                   10                  15

Gly Ser Lys Ser Phe Ala Thr Ala Lys Leu Phe Asp Pro Ala Thr
            20                  25                  30

Arg Arg Ser Val Leu Met Leu Tyr Thr Trp Cys Arg His Cys Asp Asp
            35                  40                  45

Val Ile Asp Asp Gln Thr His Gly Phe Ala Ser Glu Ala Ala Ala Glu
    50                  55                  60

Glu Glu Ala Thr Gln Arg Leu Ala Arg Leu Arg Thr Leu Thr Leu Ala
65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
            100                 105                 110

Leu Asp Gly Phe Ala Met Asp Val Ala Gln Thr Arg Tyr Val Thr Phe
        115                 120                 125

Glu Asp Thr Leu Arg Tyr Cys Tyr His Val Ala Gly Val Val Gly Leu
    130                 135                 140

Met Met Ala Arg Val Met Gly Val Arg Asp Glu Arg Val Leu Asp Arg
145                 150                 155                 160

Ala Cys Asp Leu Gly Leu Ala Phe Gln Leu Thr Asn Ile Ala Arg Asp
                165                 170                 175

Ile Ile Asp Asp Ala Ala Ile Asp Arg Cys Tyr Leu Pro Ala Glu Trp
            180                 185                 190

Leu Gln Asp Ala Gly Leu Thr Pro Glu Asn Tyr Ala Ala Arg Glu Asn
        195                 200                 205

Arg Ala Ala Leu Ala Arg Val Ala Glu Arg Leu Ile Asp Ala Ala Glu
    210                 215                 220

Pro Tyr Tyr Ile Ser Ser Gln Ala Gly Leu His Asp Leu Pro Pro Arg
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
            260                 265                 270

Thr Ser Lys Gly Glu Lys Ile Ala Met Leu Met Ala Ala Pro Gly Gln
        275                 280                 285

Val Ile Arg Ala Lys Thr Thr Arg Val Thr Pro Arg Pro Ala Gly Leu
    290                 295                 300

Trp Gln Arg Pro Val
305

<210> SEQ ID NO 5
<211> LENGTH: 492
<212> TYPE: PRT
<213> ORGANISM: Pantoea agglomerans
```

<400> SEQUENCE: 5

```
Met Lys Lys Thr Val Val Ile Gly Ala Gly Phe Gly Gly Leu Ala Leu
1               5                   10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Ala Glu Leu Glu Ala Gln Ile Thr Gln
            100                 105                 110

Phe Asn Pro Arg Asp Val Glu Gly Tyr Arg Arg Phe Leu Ala Tyr Ser
        115                 120                 125

Gln Ala Val Phe Gln Glu Gly Tyr Leu Arg Leu Gly Ser Val Pro Phe
    130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
                165                 170                 175

Glu His Leu Arg Gln Ala Phe Ser Phe His Ser Leu Leu Val Gly Gly
            180                 185                 190

Asn Pro Phe Thr Thr Ser Ser Ile Tyr Thr Leu Ile His Ala Leu Glu
        195                 200                 205

Arg Glu Trp Gly Val Trp Phe Pro Glu Gly Gly Thr Gly Ala Leu Val
    210                 215                 220

Asn Gly Met Val Lys Leu Phe Thr Asp Leu Gly Gly Glu Ile Glu Leu
225                 230                 235                 240

Asn Ala Arg Val Glu Glu Leu Val Val Ala Asp Asn Arg Val Ser Gln
                245                 250                 255

Val Arg Leu Ala Asp Gly Arg Ile Phe Asp Thr Asp Ala Val Ala Ser
            260                 265                 270

Asn Ala Asp Val Val Asn Thr Tyr Lys Lys Leu Leu Gly His His Pro
        275                 280                 285

Val Gly Gln Lys Arg Ala Ala Ala Leu Glu Arg Lys Ser Met Ser Asn
    290                 295                 300

Ser Leu Phe Val Leu Tyr Phe Gly Leu Asn Gln Pro His Ser Gln Leu
305                 310                 315                 320

Ala His His Thr Ile Cys Phe Gly Pro Arg Tyr Arg Glu Leu Ile Asp
                325                 330                 335

Glu Ile Phe Thr Gly Ser Ala Leu Ala Asp Asp Phe Ser Leu Tyr Leu
            340                 345                 350

His Ser Pro Cys Val Thr Asp Pro Ser Leu Ala Pro Gly Cys Ala
        355                 360                 365

Ser Phe Tyr Val Leu Ala Pro Val Pro His Leu Gly Asn Ala Pro Leu
    370                 375                 380

Asp Trp Ala Gln Glu Gly Pro Lys Leu Arg Asp Arg Ile Phe Asp Tyr
385                 390                 395                 400

Leu Glu Glu Arg Tyr Met Pro Gly Leu Arg Ser Gln Leu Val Thr Gln
                405                 410                 415
```

```
Arg Ile Phe Thr Pro Ala Asp Phe His Asp Thr Leu Asp Ala His Leu
            420                 425                 430

Gly Ser Ala Phe Ser Ile Glu Pro Leu Leu Thr Gln Ser Ala Trp Phe
            435                 440                 445

Arg Pro His Asn Arg Asp Ser Asp Ile Ala Asn Leu Tyr Leu Val Gly
            450                 455                 460

Ala Gly Thr His Pro Gly Ala Gly Ile Pro Gly Val Val Ala Ser Ala
465                 470                 475                 480

Lys Ala Thr Ala Ser Leu Met Ile Glu Asp Leu Gln
                    485                 490

<210> SEQ ID NO 6
<211> LENGTH: 511
<212> TYPE: PRT
<213> ORGANISM: Rhodopseudomonas palustris

<400> SEQUENCE: 6

Met Leu Asp Pro Gly Pro Asn Pro Ala Pro Arg Pro Ser Arg Asp Arg
1               5                   10                  15

Ala Pro His Ala Val Val Ile Gly Ser Gly Phe Gly Gly Leu Ala Ala
            20                  25                  30

Ala Val Arg Leu Gly Ala Lys Gly Tyr Arg Val Thr Val Leu Glu Lys
            35                  40                  45

Leu Asp Lys Ala Gly Gly Arg Ala Tyr Val His Lys Gln Asp Gly Phe
        50                  55                  60

Ser Phe Asp Ala Gly Pro Thr Ile Val Thr Ala Pro Tyr Leu Phe Glu
65                  70                  75                  80

Glu Leu Trp Lys Leu Cys Gly Lys Arg Met Ser Asp Asp Ile Thr Leu
                85                  90                  95

Lys Pro Met Ser Pro Phe Tyr Arg Ile Arg Phe Asp Asp Gly Thr His
            100                 105                 110

Phe Asp Tyr Ser Asp Asp Arg Asp Ala Val Leu Asp Gln Ile Ala Lys
            115                 120                 125

Phe Cys Pro Asp Asp Val Pro Ala Tyr Asp Arg Phe Met Ala Ala Ser
        130                 135                 140

His Glu Ile Phe Lys Val Gly Phe Glu Gln Leu Gly Asp Gln Pro Phe
145                 150                 155                 160

Ser His Phe Thr Asp Met Leu Lys Ile Ala Pro Ala Met Ile Lys Leu
                165                 170                 175

Glu Ser Tyr Arg Ser Val Tyr Gly Leu Val Ala Lys His Phe Lys Asp
            180                 185                 190

Pro Lys Leu Arg Gln Val Phe Ser Phe His Pro Leu Leu Ile Gly Gly
            195                 200                 205

Asn Pro Phe Met Ser Ser Val Tyr Cys Leu Ile Thr Tyr Leu Glu
        210                 215                 220

Lys Gln Trp Gly Val His Ser Ala Met Gly Gly Thr Gly Ala Leu Val
225                 230                 235                 240

Thr Gly Leu Val Asn Leu Ile Glu Gly Gln Gly Asn Thr Ile Arg Tyr
                245                 250                 255

Asn Gln Asp Val Arg Gln Ile Val Val Glu Asn Gly Thr Ala Cys Gly
            260                 265                 270

Val Lys Leu Ala Asp Gly Glu Val Ile Lys Ala Asp Ile Val Val Ser
            275                 280                 285

Asn Ala Asp Ser Ala Ser Thr Tyr Arg Tyr Leu Leu Pro Pro Glu Thr
```

```
            290                 295                 300
Arg Lys Arg Trp Thr Asp Ala Lys Ile Glu Lys Ser Arg Tyr Ser Met
305                 310                 315                 320

Ser Leu Phe Val Trp Tyr Phe Gly Thr Lys Arg Arg Tyr Glu Asp Val
                325                 330                 335

Lys His His Thr Ile Leu Leu Gly Pro Arg Tyr Lys Glu Leu Ile Ser
                340                 345                 350

Asp Ile Phe Ser Arg Lys Val Val Ala Glu Asp Phe Ser Leu Tyr Leu
                355                 360                 365

His Arg Pro Thr Ala Thr Asp Pro Ser Leu Ala Pro Gln Gly Cys Asp
                370                 375                 380

Thr Phe Tyr Val Leu Ser Pro Val Pro Asn Leu Leu Gly Asp Thr Asp
385                 390                 395                 400

Trp His Thr Lys Ala Glu Thr Tyr Arg Ala Ser Ile Ala Lys Met Leu
                405                 410                 415

Gly Ala Thr Val Leu Pro Asp Leu Glu Asn Gln Ile Ala Thr Ser Lys
                420                 425                 430

Ile Thr Thr Pro Ile Asp Phe Gln Asp Arg Leu Ser Ser Phe Arg Gly
                435                 440                 445

Ala Ala Phe Gly Leu Glu Pro Val Leu Trp Gln Ser Ala Trp Phe Arg
                450                 455                 460

Pro His Asn Gln Ser Glu Asp Val Lys Arg Leu Tyr Leu Val Gly Ala
465                 470                 475                 480

Gly Thr His Pro Gly Ala Gly Leu Pro Gly Val Leu Ser Ser Ala Arg
                485                 490                 495

Val Leu Asp Ala Leu Val Pro Glu Ala Asp Ser Leu Val Thr Ser
                500                 505                 510

<210> SEQ ID NO 7
<211> LENGTH: 382
<212> TYPE: PRT
<213> ORGANISM: Pantoea ananatis

<400> SEQUENCE: 7

Met Gln Pro His Tyr Asp Leu Ile Leu Val Gly Ala Gly Leu Ala Asn
1               5                   10                  15

Gly Leu Ile Ala Leu Arg Leu Gln Gln Gln Gln Pro Asp Met Arg Ile
                20                  25                  30

Leu Leu Ile Asp Ala Ala Pro Gln Ala Gly Gly Asn His Thr Trp Ser
                35                  40                  45

Phe His His Asp Asp Leu Thr Glu Ser Gln His Arg Trp Ile Ala Pro
                50                  55                  60

Leu Val Val His His Trp Pro Asp Tyr Gln Val Arg Phe Pro Thr Arg
65                  70                  75                  80

Arg Arg Lys Leu Asn Ser Gly Tyr Phe Cys Ile Thr Ser Gln Arg Phe
                85                  90                  95

Ala Glu Val Leu Gln Arg Gln Phe Gly Pro His Leu Trp Met Asp Thr
                100                 105                 110

Ala Val Ala Glu Val Asn Ala Glu Ser Val Arg Leu Lys Lys Gly Gln
                115                 120                 125

Val Ile Gly Ala Arg Ala Val Ile Asp Gly Arg Gly Tyr Ala Ala Asn
                130                 135                 140

Ser Ala Leu Ser Val Gly Phe Gln Ala Phe Ile Gly Gln Glu Trp Arg
145                 150                 155                 160
```

Leu Ser His Pro His Gly Leu Ser Ser Pro Ile Ile Met Asp Ala Thr
            165                 170                 175

Val Asp Gln Gln Asn Gly Tyr Arg Phe Val Tyr Ser Leu Pro Leu Ser
        180                 185                 190

Pro Thr Arg Leu Leu Ile Glu Asp Thr His Tyr Ile Asp Asn Ala Thr
        195                 200                 205

Leu Asp Pro Glu Cys Ala Arg Gln Asn Ile Cys Asp Tyr Ala Ala Gln
    210                 215                 220

Gln Gly Trp Gln Leu Gln Thr Leu Leu Arg Glu Gln Gly Ala Leu
225                 230                 235                 240

Pro Ile Thr Leu Ser Gly Asn Ala Asp Ala Phe Trp Gln Gln Arg Pro
                245                 250                 255

Leu Ala Cys Ser Gly Leu Arg Ala Gly Leu Phe His Pro Thr Thr Gly
            260                 265                 270

Tyr Ser Leu Pro Leu Ala Val Ala Val Ala Asp Arg Leu Ser Ala Leu
        275                 280                 285

Asp Val Phe Thr Ser Ala Ser Ile His His Ala Ile Thr His Phe Ala
    290                 295                 300

Arg Glu Arg Trp Gln Gln Gln Gly Phe Phe Arg Met Leu Asn Arg Met
305                 310                 315                 320

Leu Phe Leu Ala Gly Pro Ala Asp Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Leu Thr Asp Arg Leu Arg Ile Leu Ser Gly Lys Pro Pro Val
        355                 360                 365

Pro Val Leu Ala Ala Leu Gln Ala Ile Met Thr Thr His Arg
    370                 375                 380

<210> SEQ ID NO 8
<211> LENGTH: 275
<212> TYPE: PRT
<213> ORGANISM: uncultured marine bacterium 66A03

<400> SEQUENCE: 8

Met Gly Leu Met Leu Ile Asp Trp Cys Ala Leu Ala Leu Val Val Phe
1               5                   10                  15

Ile Gly Leu Pro His Gly Ala Leu Asp Ala Ala Ile Ser Phe Ser Met
            20                  25                  30

Ile Ser Ser Ala Lys Arg Ile Ala Arg Leu Ala Gly Ile Leu Leu Ile
        35                  40                  45

Tyr Leu Leu Leu Ala Thr Ala Phe Phe Leu Ile Trp Tyr Gln Leu Pro
    50                  55                  60

Ala Phe Ser Leu Leu Ile Phe Leu Leu Ile Ser Ile His Phe Gly
65                  70                  75                  80

Met Ala Asp Phe Asn Ala Ser Pro Ser Lys Leu Lys Trp Pro His Ile
                85                  90                  95

Ile Ala His Gly Gly Val Val Thr Val Trp Leu Pro Leu Ile Gln Lys
            100                 105                 110

Asn Glu Val Thr Lys Leu Phe Ser Ile Leu Thr Asn Gly Pro Thr Pro
        115                 120                 125

Ile Leu Trp Asp Ile Leu Leu Ile Phe Phe Leu Cys Trp Ser Ile Gly
    130                 135                 140

Val Cys Leu His Thr Tyr Glu Thr Leu Arg Ser Lys His Tyr Asn Ile
145                 150                 155                 160

```
Ala Phe Glu Leu Ile Gly Leu Ile Phe Leu Ala Trp Tyr Ala Pro Pro
                165                 170                 175

Leu Val Thr Phe Ala Thr Tyr Phe Cys Phe Ile His Ser Arg Arg His
            180                 185                 190

Phe Ser Phe Val Trp Lys Gln Leu Gln His Met Ser Ser Lys Lys Met
        195                 200                 205

Met Ile Gly Ser Ala Ile Ile Leu Ser Cys Thr Ser Trp Leu Ile Gly
        210                 215                 220

Gly Gly Ile Tyr Phe Phe Leu Asn Ser Lys Met Ile Ala Ser Glu Ala
225                 230                 235                 240

Ala Leu Gln Thr Val Phe Ile Gly Leu Ala Ala Leu Thr Val Pro His
            245                 250                 255

Met Ile Leu Ile Asp Phe Ile Phe Arg Pro His Ser Ser Arg Ile Lys
        260                 265                 270

Ile Lys Asn
        275

<210> SEQ ID NO 9
<211> LENGTH: 347
<212> TYPE: PRT
<213> ORGANISM: Cronobacter sakazakii

<400> SEQUENCE: 9

Met Lys Asp Lys Glu Leu Ser Gln Arg Lys Asn Asp His Leu Asp Ile
1               5                   10                  15

Val Leu His Pro Glu Arg Ala Lys Gln Thr Ile Arg Thr Gly Phe Glu
            20                  25                  30

Gln Trp Arg Phe Glu His Cys Ala Leu Pro Glu Leu Ala Leu Asp Asp
        35                  40                  45

Ile Asp Leu Ser Thr Arg Leu Phe Gly Arg Val Met Lys Ala Pro Leu
    50                  55                  60

Leu Ile Ser Ser Met Thr Gly Gly Ala Arg Arg Ala Ser Asp Ile Asn
65                  70                  75                  80

Arg His Leu Ala Glu Ala Ala Gln Thr Leu Gly Leu Ala Met Gly Val
                85                  90                  95

Gly Ser Gln Arg Val Ala Leu Glu Ser Glu Asp Asn Trp Gly Leu Thr
            100                 105                 110

Gly Glu Leu Arg Arg Tyr Ala Pro Asp Ile Pro Leu Leu Ala Asn Leu
        115                 120                 125

Gly Ala Ala Gln Ile Gly Ser Leu Gln Gly Leu Asp Tyr Ala Arg Arg
    130                 135                 140

Ala Val Glu Met Val Glu Ala Asp Ala Leu Ile Ile His Leu Asn Pro
145                 150                 155                 160

Leu Gln Glu Ala Leu Gln Thr Gly Gly Asp Arg Asp Trp Arg Gly Val
                165                 170                 175

Leu Ala Ala Ile Lys Arg Val Val Asn Ala Leu Ser Val Pro Val Val
            180                 185                 190

Val Lys Glu Val Gly Ala Gly Leu Ser Val Pro Val Ala Arg Gln Leu
        195                 200                 205

Ala Glu Ala Gly Val Thr Met Leu Asp Val Ala Gly Ala Gly Gly Thr
    210                 215                 220

Ser Trp Ala Ala Val Glu Gly Glu Arg Ala Ala Ser Asp His Ala Arg
225                 230                 235                 240

Ser Val Ala Met Ala Phe Ala Asp Trp Gly Ile Pro Thr Ala Gln Ala
```

```
                        245                 250                 255
Leu Arg Gln Ile His Gln Ala Phe Pro Ser Met Pro Leu Ile Ala Ser
            260                 265                 270

Gly Gly Ile Arg Asp Gly Ile Asp Thr Ala Lys Ala Leu Ala Met Gly
        275                 280                 285

Ala Ser Leu Val Gly Gln Ala Ala Ala Val Leu Gly Ser Ala Thr Thr
    290                 295                 300

Ser Thr Ser Ala Val Leu Asp His Phe Ala Val Val Ile Glu Gln Leu
305                 310                 315                 320

Arg Val Ala Cys Phe Cys Thr Gly Ser Ala Ser Leu Ser Ala Leu Arg
                325                 330                 335

Glu Ala Arg Leu Ala Arg Val Gly Asp Glu Glu
            340                 345

<210> SEQ ID NO 10
<211> LENGTH: 382
<212> TYPE: PRT
<213> ORGANISM: Corynebacterium glutamicum

<400> SEQUENCE: 10

Leu Arg Asp Asn Trp Pro Cys Asp Thr Arg Met Asp Asn Gly Met Thr
1               5                   10                  15

Ile Thr Thr Glu His Ser Thr His Pro Asp Leu Asp Phe Asn Asp Glu
            20                  25                  30

Ile Tyr Arg Glu Leu Asn Arg Ile Cys Ala Ser Leu Ser Gln Gln Cys
        35                  40                  45

Ser Thr Tyr Gln Pro Glu Phe Arg Thr Cys Leu Asp Ala Ala Phe Gln
    50                  55                  60

Ala Leu Arg Gly Gly Lys Leu Ile Arg Pro Arg Met Leu Leu Gly Leu
65                  70                  75                  80

Tyr Asn Thr Leu Val Asp Asp Ile Glu Val Lys Leu Asn Thr Val
            85                  90                  95

Leu Gln Val Ala Val Ala Leu Glu Leu Leu His Phe Ser Leu Leu Val
            100                 105                 110

His Asp Asp Val Ile Asp Gly Asp Leu Tyr Arg Arg Gly Lys Leu Asn
        115                 120                 125

Phe Ile Gly Gln Ile Leu Met His Arg Thr Pro Glu Ser Phe Ala Gln
130                 135                 140

Ile Gln Arg Asp Pro Glu His Leu Asp Trp Ala Gln Ser Asn Gly Leu
145                 150                 155                 160

Leu Met Gly Asn Leu Phe Leu Ala Ala Thr His Gln Ile Phe Ala Arg
                165                 170                 175

Leu Asp Leu Pro His His Gln Arg Val Arg Leu Leu Asp Leu Leu Asn
            180                 185                 190

His Thr Ile Asn Asp Thr Ile Val Gly Glu Phe Leu Asp Val Gly Leu
        195                 200                 205

Ser Ser Lys Ala Ile Ser Pro Asn Met Asp Ile Ala Leu Glu Met Ser
    210                 215                 220

Arg Leu Lys Thr Ala Thr Tyr Thr Phe Glu Leu Pro Met Arg Ala Ala
225                 230                 235                 240

Ala Ile Leu Ala Glu Leu Pro Gln Glu Ile Glu Thr Lys Ile Gly Glu
                245                 250                 255

Ile Gly Thr Asn Leu Gly Ile Ala Tyr Gln Leu Gln Asp Asp Tyr Leu
            260                 265                 270
```

```
Ser Thr Phe Gly Asp Ala Ala Glu His Gly Lys Asp Ala Phe Ser Asp
            275                 280                 285

Leu Arg Glu Gly Lys Glu Thr Thr Ile Ile Ala Phe Ala Arg Asp Thr
290                 295                 300

Ala Lys Trp Thr Asp Ile Gln Asp Asn Phe Gly Ser Ala Asp Leu Ser
305                 310                 315                 320

Thr Ser Gln Ala Glu Arg Ile Gln His Leu Leu Ile Gln Cys Gly Ala
            325                 330                 335

Lys Asn His Ser Leu Asn Ala Ile Ser Asp His Leu Asn Ile Cys Arg
            340                 345                 350

Ser Met Ile Lys Thr Leu Ser Pro Gln Val Asp Pro Lys Ala Gln Asn
            355                 360                 365

Leu Leu Leu Lys Gln Val Glu Gln Leu Ala Ser Arg Lys Ser
            370                 375                 380

<210> SEQ ID NO 11
<211> LENGTH: 304
<212> TYPE: PRT
<213> ORGANISM: Corynebacterium glutamicum

<400> SEQUENCE: 11

Met Thr His Gln Asn Ser Pro Leu Phe Leu Lys Ser Ala Leu Arg Leu
1               5                   10                  15

Tyr Asn Arg Ala Ser Phe Lys Ala Ser His Lys Val Ile Glu Glu Tyr
            20                  25                  30

Ser Thr Ser Phe Ser Leu Ser Thr Trp Leu Leu Ser Pro Arg Ile Arg
            35                  40                  45

Asn Asp Ile Arg Asn Leu Tyr Ala Val Val Arg Ile Ala Asp Glu Ile
        50                  55                  60

Val Asp Gly Thr Ala His Ala Ala Gly Cys Ser Thr Ala Lys Ile Glu
65                  70                  75                  80

Glu Ile Leu Asp Ala Tyr Glu Ile Ala Val Leu Ala Ala Pro Gln Gln
                85                  90                  95

Arg Phe Asn Thr Asp Leu Val Leu Gln Ala Tyr Gly Glu Thr Ala Arg
            100                 105                 110

Arg Cys Asp Phe Glu Gln Glu His Val Ile Ala Phe Ala Ser Met
            115                 120                 125

Arg Lys Asp Leu Lys Ala Asn Thr His Asp Pro Asp Ser Phe Thr Thr
        130                 135                 140

Tyr Val Tyr Gly Ser Ala Glu Val Ile Gly Leu Leu Cys Leu Ser Val
145                 150                 155                 160

Phe Asn Gln Gly Arg Thr Ile Ser Lys Lys Arg Leu Glu Ile Met Gln
                165                 170                 175

Asn Gly Ala Arg Ser Leu Gly Ala Ala Phe Gln Lys Ile Asn Phe Leu
            180                 185                 190

Arg Asp Leu Ala Glu Asp Gln Gln Asn Leu Gly Arg Phe Tyr Phe Pro
            195                 200                 205

Lys Thr Ser Gln Gly Thr Leu Thr Lys Glu Gln Lys Glu Asp Leu Ile
        210                 215                 220

Ala Asp Ile Arg Gln Asp Leu Ala Ile Ala His Asp Ala Phe Pro Glu
225                 230                 235                 240

Ile Pro Val Gln Ala Arg Ile Gly Val Ile Ser Ala Tyr Leu Leu Phe
                245                 250                 255

Gln Lys Leu Thr Asp Arg Ile Glu Ala Thr Pro Thr Ala Asp Leu Leu
            260                 265                 270
```

Arg Glu Arg Ile Arg Val Pro Leu His Ile Lys Leu Ser Thr Leu Ala
            275                 280                 285

Arg Ala Thr Met Lys Gly Leu Ser Met Ser Ile Tyr Arg Lys Asn Ser
    290                 295                 300

<210> SEQ ID NO 12
<211> LENGTH: 548
<212> TYPE: PRT
<213> ORGANISM: Corynebacterium glutamicum

<400> SEQUENCE: 12

Met Lys Val Ser Thr Lys Thr Pro Arg Ser Ser Gly Thr Ala Val Val
1               5                   10                  15

Ile Gly Ala Gly Val Ala Gly Leu Ala Thr Ser Ala Leu Leu Ala Arg
            20                  25                  30

Asp Gly Trp Gln Val Thr Val Leu Glu Lys Asn Thr Asp Val Gly Gly
        35                  40                  45

Arg Ala Gly Ser Leu Glu Ile Ser Gly Phe Pro Gly Phe Arg Trp Asp
    50                  55                  60

Thr Gly Pro Ser Trp Tyr Leu Met Pro Glu Ala Phe Asp His Phe Phe
65                  70                  75                  80

Ala Leu Phe Gly Ala Cys Thr Ser Asp Tyr Leu Asp Leu Val Glu Leu
                85                  90                  95

Thr Pro Gly Tyr Arg Val Phe Ser Gly Thr His Asp Ala Val Asp Val
            100                 105                 110

Pro Thr Gly Arg Glu Glu Ala Ile Ala Leu Phe Glu Ser Ile Glu Pro
        115                 120                 125

Gly Ala Gly Ala Lys Leu Gly Asn Tyr Leu Asp Ser Ala Ala Asp Ala
    130                 135                 140

Tyr Asp Ile Ala Ile Asp Arg Phe Leu Tyr Asn Asn Phe Ser Thr Leu
145                 150                 155                 160

Gly Pro Leu Leu His Arg Asp Val Leu Thr Arg Ala Gly Arg Leu Phe
                165                 170                 175

Ser Leu Leu Thr Arg Ser Leu Gln Lys Tyr Val Asn Ser Gln Phe Ser
            180                 185                 190

Ser Pro Val Leu Arg Gln Ile Leu Thr Tyr Pro Ala Val Phe Leu Ser
        195                 200                 205

Ser Arg Pro Thr Thr Thr Pro Ser Met Tyr His Leu Met Ser His Thr
    210                 215                 220

Asp Leu Val Gln Gly Val Lys Tyr Pro Ile Gly Gly Phe Thr Ala Val
225                 230                 235                 240

Val Asn Ala Leu His Gln Leu Ala Leu Glu Asn Gly Val Glu Phe Gln
                245                 250                 255

Leu Asp Ser Glu Val Ile Ser Ile Asn Thr Ala Ser Ser Arg Gly Asn
            260                 265                 270

Thr Ser Ala Thr Gly Val Ser Leu Leu His Asn Arg Lys Val Gln Asn
        275                 280                 285

Leu Asp Ala Asp Leu Val Val Ser Ala Gly Asp Leu His His Thr Glu
    290                 295                 300

Asn Asn Leu Leu Pro Arg Glu Leu Arg Thr Tyr Pro Glu Arg Tyr Trp
305                 310                 315                 320

Ser Asn Arg Asn Pro Gly Ile Gly Ala Val Leu Ile Leu Leu Gly Val
                325                 330                 335

Lys Gly Glu Leu Pro Gln Leu Asp His His Asn Leu Phe Phe Ser Glu

```
            340                 345                 350
Asp Trp Thr Asp Asp Phe Ala Val Val Phe Asp Gly Pro Gln Leu Thr
        355                 360                 365

Arg Pro His Asn Ala Ser Asn Ser Ile Tyr Val Ser Lys Pro Ser Thr
    370                 375                 380

Ser Glu Asp Gly Val Ala Pro Ala Gly Tyr Glu Asn Leu Phe Val Leu
385                 390                 395                 400

Ile Pro Thr Lys Ala Ser Ser Ile Gly His Gly Asp Ala Tyr Met
                405                 410                 415

Gln Ser Ala Ser Ala Ser Val Glu Thr Ile Ala Ser His Ala Ile Asn
                420                 425                 430

Gln Ile Ala Thr Gln Ala Gly Ile Pro Asp Leu Thr Asp Arg Ile Val
            435                 440                 445

Val Lys Arg Thr Ile Gly Pro Ala Asp Phe Glu His Arg Tyr His Ser
    450                 455                 460

Trp Val Gly Ser Ala Leu Gly Pro Ala His Thr Leu Arg Gln Ser Ala
465                 470                 475                 480

Phe Leu Arg Gly Arg Asn Ser Ser Arg Lys Val Asn Asn Leu Phe Tyr
                485                 490                 495

Ser Gly Ala Thr Thr Val Pro Gly Val Gly Ile Pro Met Cys Leu Ile
                500                 505                 510

Ser Ala Glu Asn Ile Ile Lys Arg Leu His Ala Asp Thr Ser Ala Gly
            515                 520                 525

Pro Leu Pro Glu Pro Leu Pro Pro Lys Thr Thr Pro Ser Gln Lys Thr
    530                 535                 540

Ser Tyr Asp His
545

<210> SEQ ID NO 13
<211> LENGTH: 195
<212> TYPE: PRT
<213> ORGANISM: Corynebacterium glutamicum

<400> SEQUENCE: 13

Met Ser Lys Leu Arg Gly Met Thr Thr Glu Val Glu Leu Val Val Leu
1               5                   10                  15

Ala Asp Ser Glu Gly Asn Pro Ile Gly Thr Ala Pro Lys Ala Thr Val
                20                  25                  30

His Thr Lys Asp Thr Pro Leu His Phe Ala Phe Ser Thr Tyr Ile Leu
            35                  40                  45

Asn Pro Arg Gly Glu Leu Leu Val Thr Arg Arg Ala Leu Ser Lys Lys
        50                  55                  60

Thr Trp Pro Gly Val Trp Thr Asn Ser Met Cys Gly His Pro Gly Pro
65                  70                  75                  80

Asp Glu Thr Asn Ala Asp Ala Ile Arg Arg Gly Val Asp Glu Leu
                85                  90                  95

Gly Leu Glu Val Asp Ser Phe Leu Asp Ile Gln Glu Ile Leu Pro Asp
                100                 105                 110

Tyr Gln Tyr Arg Ala Val Asp Ala Ser Gly Ile Val Glu Trp Glu Leu
            115                 120                 125

Cys Pro Val His Leu Val Arg Leu Ala Val Gly Glu Phe Val Glu Pro
        130                 135                 140

Leu Asp Asp Glu Val Glu Glu Phe Glu Trp Ala Glu Pro Gln Lys Leu
145                 150                 155                 160
```

```
Phe Asp Ala Val Asp Ala Thr Pro Phe Val Phe Ser Pro Trp Leu Val
                165                 170                 175

Asp Gln Leu Ser Ala Pro Glu Leu Arg Gln Ala Ile Leu Glu Ala Phe
            180                 185                 190

Asp Ala Glu
        195

<210> SEQ ID NO 14
<211> LENGTH: 627
<212> TYPE: PRT
<213> ORGANISM: escherichia coli

<400> SEQUENCE: 14

Met Glu Phe Arg Arg Pro Leu Met Ser Phe Asp Ile Ala Lys Tyr Pro
1               5                   10                  15

Thr Leu Ala Leu Val Asp Ser Thr Gln Glu Leu Arg Leu Leu Pro Lys
            20                  25                  30

Glu Ser Leu Pro Lys Leu Cys Asp Glu Leu Arg Arg Tyr Leu Leu Asp
        35                  40                  45

Ser Val Ser Arg Ser Ser Gly His Phe Ala Ser Gly Leu Gly Thr Val
    50                  55                  60

Glu Leu Thr Val Ala Leu His Tyr Val Tyr Asn Thr Pro Phe Asp Gln
65                  70                  75                  80

Leu Ile Trp Asp Val Gly His Gln Ala Tyr Pro His Lys Ile Leu Thr
                85                  90                  95

Gly Arg Arg Asp Lys Ile Gly Thr Ile Arg Gln Lys Gly Gly Leu His
            100                 105                 110

Pro Phe Pro Trp Arg Gly Glu Ser Glu Tyr Asp Val Leu Ser Val Gly
        115                 120                 125

His Ser Ser Thr Ser Ile Ser Ala Gly Ile Gly Ile Ala Val Ala Ala
    130                 135                 140

Glu Lys Glu Gly Lys Asn Arg Arg Thr Val Cys Val Ile Gly Asp Gly
145                 150                 155                 160

Ala Ile Thr Ala Gly Met Ala Phe Glu Ala Met Asn His Ala Gly Asp
                165                 170                 175

Ile Arg Pro Asp Met Leu Val Ile Leu Asn Asp Asn Glu Met Ser Ile
            180                 185                 190

Ser Glu Asn Val Gly Ala Leu Asn Asn His Leu Ala Gln Leu Leu Ser
        195                 200                 205

Gly Lys Leu Tyr Ser Ser Leu Arg Glu Gly Gly Lys Lys Val Phe Ser
    210                 215                 220

Gly Val Pro Pro Ile Lys Glu Leu Leu Lys Arg Thr Glu Glu His Ile
225                 230                 235                 240

Lys Gly Met Val Val Pro Gly Thr Leu Phe Glu Glu Leu Gly Phe Asn
                245                 250                 255

Tyr Ile Gly Pro Val Asp Gly His Asp Val Leu Gly Leu Ile Thr Thr
            260                 265                 270

Leu Lys Asn Met Arg Asp Leu Lys Gly Pro Gln Phe Leu His Ile Met
        275                 280                 285

Thr Lys Lys Gly Arg Gly Tyr Glu Pro Ala Glu Lys Asp Pro Ile Thr
    290                 295                 300

Phe His Ala Val Pro Lys Phe Asp Pro Ser Ser Gly Cys Leu Pro Lys
305                 310                 315                 320

Ser Ser Gly Gly Leu Pro Ser Tyr Ser Lys Ile Phe Gly Asp Trp Leu
                325                 330                 335
```

```
Cys Glu Thr Ala Ala Lys Asp Asn Lys Leu Met Ala Ile Thr Pro Ala
            340                 345                 350

Met Arg Glu Gly Ser Gly Met Val Glu Phe Ser Arg Lys Phe Pro Asp
            355                 360                 365

Arg Tyr Phe Asp Val Ala Ile Ala Glu Gln His Ala Val Thr Phe Ala
        370                 375                 380

Ala Gly Leu Ala Ile Gly Gly Tyr Lys Pro Ile Val Ala Ile Tyr Ser
385                 390                 395                 400

Thr Phe Leu Gln Arg Ala Tyr Asp Gln Val Leu His Asp Val Ala Ile
                405                 410                 415

Gln Lys Leu Pro Val Leu Phe Ala Ile Asp Arg Ala Gly Ile Val Gly
            420                 425                 430

Ala Asp Gly Gln Thr His Gln Gly Ala Phe Asp Leu Ser Tyr Leu Arg
            435                 440                 445

Cys Ile Pro Glu Met Val Ile Met Thr Pro Ser Asp Glu Asn Glu Cys
            450                 455                 460

Arg Gln Met Leu Tyr Thr Gly Tyr His Tyr Asn Asp Gly Pro Ser Ala
465                 470                 475                 480

Val Arg Tyr Pro Arg Gly Asn Ala Val Gly Val Glu Leu Thr Pro Leu
                485                 490                 495

Glu Lys Leu Pro Ile Gly Lys Gly Ile Val Lys Arg Gly Glu Lys
            500                 505                 510

Leu Ala Ile Leu Asn Phe Gly Thr Leu Met Pro Glu Ala Ala Lys Val
            515                 520                 525

Ala Glu Ser Leu Asn Ala Thr Leu Val Asp Met Arg Phe Val Lys Pro
            530                 535                 540

Leu Asp Glu Ala Leu Ile Leu Glu Met Ala Ala Ser His Glu Ala Leu
545                 550                 555                 560

Val Thr Val Glu Glu Asn Ala Ile Met Gly Gly Ala Gly Ser Gly Val
                565                 570                 575

Asn Glu Val Leu Met Ala His Arg Lys Pro Val Pro Val Leu Asn Ile
            580                 585                 590

Gly Leu Pro Asp Phe Phe Ile Pro Gln Gly Thr Gln Glu Glu Met Arg
            595                 600                 605

Ala Glu Leu Gly Leu Asp Ala Ala Gly Met Glu Ala Lys Ile Lys Ala
            610                 615                 620

Trp Leu Ala
625

<210> SEQ ID NO 15
<211> LENGTH: 636
<212> TYPE: PRT
<213> ORGANISM: Corynebacterium glutamicum

<400> SEQUENCE: 15

Met Gly Ile Leu Asn Ser Ile Ser Thr Pro Ala Asp Leu Lys Ala Leu
1               5                   10                  15

Asn Asp Glu Asp Leu Asp Ala Leu Ala Lys Glu Ile Arg Thr Phe Leu
            20                  25                  30

Val Asp Lys Val Ala Ala Thr Gly Gly His Leu Gly Pro Asn Leu Gly
        35                  40                  45

Val Val Glu Leu Thr Ile Gly Leu His Arg Val Phe Asp Ser Pro Gln
    50                  55                  60

Asp Pro Ile Ile Phe Asp Thr Ser His Gln Ser Tyr Val His Lys Ile
```

-continued

```
              65                  70                  75                  80
Leu Thr Gly Arg Ala Lys Asp Phe Asp Ser Leu Arg Gln Lys Asp Gly
                    85                  90                  95
Leu Ser Gly Tyr Thr Cys Arg Ala Glu Ser Glu His Asp Trp Thr Glu
                    100                 105                 110
Ser Ser His Ala Ser Ala Ala Leu Ser Tyr Ala Asp Gly Leu Ser Lys
                    115                 120                 125
Ala Lys Gln Leu Asp Gly Asp Thr Thr His Ser Val Val Ala Val Val
                    130                 135                 140
Gly Asp Gly Ala Leu Thr Gly Gly Met Cys Trp Glu Ala Leu Asn Asn
145                 150                 155                 160
Ile Ala Ala Gly Lys Asp Arg Lys Val Val Val Val Asn Asp Asn
                    165                 170                 175
Gly Arg Ser Tyr Ser Pro Thr Ile Gly Gly Phe Ala Glu Asn Leu Ala
                    180                 185                 190
Gly Leu Arg Met Gln Pro Phe Tyr Asp Arg Phe Met Glu Lys Gly Lys
                    195                 200                 205
Thr Ser Leu Lys Ser Met Gly Trp Val Gly Glu Arg Thr Phe Glu Ala
                    210                 215                 220
Leu His Ala Phe Lys Glu Gly Val Lys Ser Thr Val Ile Pro Thr Glu
225                 230                 235                 240
Met Phe Pro Glu Leu Gly Met Lys Tyr Val Gly Pro Val Asp Gly His
                    245                 250                 255
Asn Gln Lys Ala Val Asp Asn Ala Leu Lys Tyr Ala His Asp Tyr Asp
                    260                 265                 270
Gly Pro Ile Ile Val His Met Val Thr Glu Lys Gly Arg Gly Tyr Ala
                    275                 280                 285
Pro Ala Glu Gln Asp Leu Asp Glu Leu Met His Ser Thr Gly Val Ile
                    290                 295                 300
Asp Pro Leu Thr Gly Ala Pro Lys Ser Ala Ser Lys Pro Gly Trp Thr
305                 310                 315                 320
Ser Val Phe Ser Asp Glu Leu Val Lys Ile Gly Ala Gln Asn Glu Asn
                    325                 330                 335
Val Val Ala Ile Thr Ala Ala Met Ala Gly Pro Thr Gly Leu Ser Lys
                    340                 345                 350
Phe Glu Ala Asn Phe Pro Asn Arg Phe Phe Asp Val Gly Ile Ala Glu
                    355                 360                 365
Gln His Ala Val Thr Ser Ala Ala Gly Leu Ala Leu Gly Gly Lys His
                    370                 375                 380
Pro Val Val Ala Ile Tyr Ser Thr Phe Leu Asn Arg Ala Phe Asp Gln
385                 390                 395                 400
Leu Leu Met Asp Val Gly Met Leu Asn Gln Pro Val Thr Leu Val Leu
                    405                 410                 415
Asp Arg Ser Gly Val Thr Gly Ser Asp Gly Ala Ser His Asn Gly Val
                    420                 425                 430
Trp Asp Met Ala Leu Thr Ser Ile Val Pro Gly Val Gln Val Ala Ala
                    435                 440                 445
Pro Arg Asp Glu Asp Ser Leu Arg Glu Leu Leu Asn Glu Ala Ile Ser
                    450                 455                 460
Ile Asp Asp Gly Pro Thr Val Val Arg Phe Pro Lys Gly Asp Leu Pro
465                 470                 475                 480
Thr Pro Ile Val Ala Ile Asp Thr Leu Glu Asp Gly Val Asp Val Leu
                    485                 490                 495
```

```
Ala Tyr Glu Asp Ala Thr Asp Val Glu Ser Thr Asp Ala Pro Ser
            500                 505                 510

Val Leu Ile Ile Ala Val Gly Glu Arg Ala Thr Val Ala Leu Asp Val
            515                 520                 525

Ala Ser Arg Ile Lys Gln His Gly Val Asn Val Thr Val Val Asp Pro
        530                 535                 540

Arg Trp Ile Val Pro Ile Pro Gln Ser Leu Val Ala Leu Ser Asp Asp
545                 550                 555                 560

His Asp Leu Val Ile Thr Ile Glu Asp Gly Val Ile His Gly Gly Val
                565                 570                 575

Gly Ser Leu Leu Ser Asp Ala Leu Asn Ala Ser Glu Val Asp Thr Pro
            580                 585                 590

Arg Arg Gln Ile Ala Val Pro Gln Lys Tyr Leu Asp His Ala Ser Arg
        595                 600                 605

Asn Glu Val Leu Ala Asp Tyr Gly Leu Asp Ala Asp Gly Ile Glu Thr
            610                 615                 620

Thr Val Val Gly Trp Leu Asp Ser Leu Phe Gly Glu
625                 630                 635

<210> SEQ ID NO 16
<211> LENGTH: 803
<212> TYPE: PRT
<213> ORGANISM: Enterococcus faecalis

<400> SEQUENCE: 16

Leu Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
        115                 120                 125

Tyr Glu Thr Glu Ser Tyr Asp Ala Pro Phe Ser Ser Met Met Tyr Asp
    130                 135                 140

Gly Leu Thr Asp Ala Phe Ser Gly Gln Ala Met Gly Leu Thr Ala Glu
145                 150                 155                 160

Asn Val Ala Glu Lys Tyr His Val Thr Arg Glu Glu Gln Asp Gln Phe
                165                 170                 175

Ser Val His Ser Gln Leu Lys Ala Ala Gln Ala Gln Ala Glu Gly Ile
            180                 185                 190

Phe Ala Asp Glu Ile Ala Pro Leu Glu Val Ser Gly Thr Leu Val Glu
        195                 200                 205

Lys Asp Glu Gly Ile Arg Pro Asn Ser Ser Val Glu Lys Leu Gly Thr
    210                 215                 220

Leu Lys Thr Val Phe Lys Glu Asp Gly Thr Val Thr Ala Gly Asn Ala
```

```
                225                 230                 235                 240
Ser Thr Ile Asn Asp Gly Ala Ser Ala Leu Ile Ile Ala Ser Gln Glu
                    245                 250                 255
Tyr Ala Glu Ala His Gly Leu Pro Tyr Leu Ala Ile Ile Arg Asp Ser
                    260                 265                 270
Val Glu Val Gly Ile Asp Pro Ala Tyr Met Gly Ile Ser Pro Ile Lys
                    275                 280                 285
Ala Ile Gln Lys Leu Leu Ala Arg Asn Gln Leu Thr Thr Glu Glu Ile
                    290                 295                 300
Asp Leu Tyr Glu Ile Asn Glu Ala Phe Ala Ala Thr Ser Ile Val Val
305                 310                 315                 320
Gln Arg Glu Leu Ala Leu Pro Glu Glu Lys Val Asn Ile Tyr Gly Gly
                    325                 330                 335
Gly Ile Ser Leu Gly His Ala Ile Gly Ala Thr Gly Ala Arg Leu Leu
                    340                 345                 350
Thr Ser Leu Ser Tyr Gln Leu Asn Gln Lys Glu Lys Lys Tyr Gly Val
                    355                 360                 365
Ala Ser Leu Cys Ile Gly Gly Gly Leu Gly Leu Ala Met Leu Leu Glu
                    370                 375                 380
Arg Pro Gln Gln Lys Lys Asn Ser Arg Phe Tyr Gln Met Ser Pro Glu
385                 390                 395                 400
Glu Arg Leu Ala Ser Leu Leu Asn Glu Gly Gln Ile Ser Ala Asp Thr
                    405                 410                 415
Lys Lys Glu Phe Glu Asn Thr Ala Leu Ser Ser Gln Ile Ala Asn His
                    420                 425                 430
Met Ile Glu Asn Gln Ile Ser Glu Thr Glu Val Pro Met Gly Val Gly
                    435                 440                 445
Leu His Leu Thr Val Asp Glu Thr Asp Tyr Leu Val Pro Met Ala Thr
                    450                 455                 460
Glu Glu Pro Ser Val Ile Ala Ala Leu Ser Asn Gly Ala Lys Ile Ala
465                 470                 475                 480
Gln Gly Phe Lys Thr Val Asn Gln Gln Arg Leu Met Arg Gly Gln Ile
                    485                 490                 495
Val Phe Tyr Asp Val Ala Asp Ala Glu Ser Leu Ile Asp Glu Leu Gln
                    500                 505                 510
Val Arg Glu Thr Glu Ile Phe Gln Gln Ala Glu Leu Ser Tyr Pro Ser
                    515                 520                 525
Ile Val Lys Arg Gly Gly Gly Leu Arg Asp Leu Gln Tyr Arg Ala Phe
                    530                 535                 540
Asp Glu Ser Phe Val Ser Val Asp Phe Leu Val Asp Val Lys Asp Ala
545                 550                 555                 560
Met Gly Ala Asn Ile Val Asn Ala Met Leu Glu Gly Val Ala Glu Leu
                    565                 570                 575
Phe Arg Glu Trp Phe Ala Glu Gln Lys Ile Leu Phe Ser Ile Leu Ser
                    580                 585                 590
Asn Tyr Ala Thr Glu Ser Val Val Thr Met Lys Thr Ala Ile Pro Val
                    595                 600                 605
Ser Arg Leu Ser Lys Gly Ser Asn Gly Arg Glu Ile Ala Glu Lys Ile
                    610                 615                 620
Val Leu Ala Ser Arg Tyr Ala Ser Leu Asp Pro Tyr Arg Ala Val Thr
625                 630                 635                 640
His Asn Lys Gly Ile Met Asn Gly Ile Glu Ala Val Val Leu Ala Thr
                    645                 650                 655
```

```
Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
        675                 680                 685

Gln Leu Ile Gly Glu Ile Ser Val Pro Leu Ala Leu Ala Thr Val Gly
    690                 695                 700

Gly Ala Thr Lys Val Leu Pro Lys Ser Gln Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
        755                 760                 765

Gly Ala Thr Gly Lys Glu Val Glu Ala Val Ala Gln Gln Leu Lys Arg
    770                 775                 780

Gln Lys Thr Met Asn Gln Asp Arg Ala Leu Ala Ile Leu Asn Asp Leu
785                 790                 795                 800

Arg Lys Gln

<210> SEQ ID NO 17
<211> LENGTH: 383
<212> TYPE: PRT
<213> ORGANISM: Enterococcus faecalis

<400> SEQUENCE: 17

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220
```

```
Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
            245                 250                 255

Glu Arg Ile Leu Ala Arg Tyr Glu Glu Ser Ile Ile Tyr Ser Arg Arg
        260                 265                 270

Val Gly Asn Leu Tyr Thr Gly Ser Leu Tyr Leu Gly Leu Ile Ser Leu
    275                 280                 285

Leu Glu Asn Ala Thr Thr Leu Thr Ala Gly Asn Gln Ile Gly Leu Phe
290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
            325                 330                 335

Asp Asn Arg Thr Glu Leu Ser Ile Ala Glu Tyr Glu Ala Met Phe Ala
        340                 345                 350

Glu Thr Leu Asp Thr Asp Ile Asp Gln Thr Leu Glu Asp Glu Leu Lys
    355                 360                 365

Tyr Ser Ile Ser Ala Ile Asn Asn Thr Val Arg Ser Tyr Arg Asn
370                 375                 380

<210> SEQ ID NO 18
<211> LENGTH: 292
<212> TYPE: PRT
<213> ORGANISM: Streptococcus pneumonia

<400> SEQUENCE: 18

Met Thr Lys Lys Val Gly Val Gly Gln Ala His Ser Lys Ile Ile Leu
1               5                   10                  15

Ile Gly Glu His Ala Val Val Tyr Gly Tyr Pro Ala Ile Ser Leu Pro
            20                  25                  30

Leu Leu Glu Val Glu Val Thr Cys Lys Val Val Pro Ala Glu Ser Pro
        35                  40                  45

Trp Arg Leu Tyr Glu Glu Asp Thr Leu Ser Met Ala Val Tyr Ala Ser
    50                  55                  60

Leu Glu Tyr Leu Asn Ile Thr Glu Ala Cys Ile Arg Cys Glu Ile Asp
65                  70                  75                  80

Ser Ala Ile Pro Glu Lys Arg Gly Met Gly Ser Ser Ala Ala Ile Ser
                85                  90                  95

Ile Ala Ala Ile Arg Ala Val Phe Asp Tyr Tyr Gln Ala Asp Leu Pro
            100                 105                 110

His Asp Val Leu Glu Ile Leu Val Asn Arg Ala Glu Met Ile Ala His
        115                 120                 125

Met Asn Pro Ser Gly Leu Asp Ala Lys Thr Cys Leu Ser Asp Gln Pro
    130                 135                 140

Ile Arg Phe Ile Lys Asn Val Gly Phe Thr Glu Leu Glu Met Asp Leu
145                 150                 155                 160

Ser Ala Tyr Leu Val Ile Ala Asp Thr Gly Val Tyr Gly His Thr Arg
                165                 170                 175

Glu Ala Ile Gln Val Val Gln Asn Lys Gly Lys Asp Ala Leu Pro Phe
            180                 185                 190

Leu His Ala Leu Gly Glu Leu Thr Gln Gln Ala Glu Val Ala Ile Ser
        195                 200                 205

Gln Lys Asp Ala Glu Gly Leu Gly Gln Ile Leu Ser Gln Ala His Leu
```

```
            210                 215                 220
His Leu Lys Glu Ile Gly Val Ser Ser Pro Glu Ala Asp Phe Leu Val
225                 230                 235                 240

Glu Thr Thr Leu Ser His Gly Ala Leu Gly Ala Lys Met Ser Gly Gly
                245                 250                 255

Gly Leu Gly Gly Cys Ile Ile Ala Leu Val Thr Asn Leu Thr His Ala
            260                 265                 270

Gln Glu Leu Ala Glu Arg Leu Glu Lys Gly Ala Val Gln Thr Trp
        275                 280                 285

Ile Glu Ser Leu
        290

<210> SEQ ID NO 19
<211> LENGTH: 336
<212> TYPE: PRT
<213> ORGANISM: Streptococcus pneumonia

<400> SEQUENCE: 19

Met Ile Ala Val Lys Thr Cys Gly Lys Leu Tyr Trp Ala Gly Glu Tyr
1               5                   10                  15

Ala Ile Leu Glu Pro Gly Gln Leu Ala Leu Ile Lys Asp Ile Pro Ile
            20                  25                  30

Tyr Met Arg Ala Glu Ile Ala Phe Ser Asp Ser Tyr Arg Ile Tyr Ser
        35                  40                  45

Asp Met Phe Asp Phe Ala Val Asp Leu Arg Pro Asn Pro Asp Tyr Ser
    50                  55                  60

Leu Ile Gln Glu Thr Ile Ala Leu Met Gly Asp Phe Leu Ala Val Arg
65                  70                  75                  80

Gly Gln Asn Leu Arg Pro Phe Ser Leu Lys Ile Cys Gly Lys Met Glu
                85                  90                  95

Arg Glu Gly Lys Lys Phe Gly Leu Gly Ser Ser Gly Ser Val Val Val
            100                 105                 110

Leu Val Val Lys Ala Leu Leu Ala Leu Tyr Asn Leu Ser Val Asp Gln
        115                 120                 125

Asn Leu Leu Phe Lys Leu Thr Ser Ala Val Leu Leu Lys Arg Gly Asp
    130                 135                 140

Asn Gly Ser Met Gly Asp Leu Ala Cys Ile Val Ala Glu Asp Leu Val
145                 150                 155                 160

Leu Tyr Gln Ser Phe Asp Arg Gln Lys Ala Ala Trp Leu Glu Glu
                165                 170                 175

Glu Asn Leu Ala Thr Val Leu Glu Arg Asp Trp Gly Phe Phe Ile Ser
            180                 185                 190

Gln Val Lys Pro Thr Leu Glu Cys Asp Phe Leu Val Gly Trp Thr Lys
        195                 200                 205

Glu Val Ala Val Ser Ser His Met Val Gln Gln Ile Lys Gln Asn Ile
    210                 215                 220

Asn Gln Asn Phe Leu Ser Ser Lys Glu Thr Val Val Ser Leu Val
225                 230                 235                 240

Glu Ala Leu Glu Gln Gly Lys Ala Glu Lys Val Ile Glu Gln Val Glu
                245                 250                 255

Val Ala Ser Lys Leu Leu Glu Gly Leu Ser Thr Asp Ile Tyr Thr Pro
            260                 265                 270

Leu Leu Arg Gln Leu Lys Glu Ala Ser Gln Asp Leu Gln Ala Val Ala
        275                 280                 285
```

```
Lys Ser Ser Gly Ala Gly Gly Gly Asp Cys Gly Ile Ala Leu Ser Phe
    290                 295                 300

Asp Ala Gln Ser Ser Arg Asn Thr Leu Lys Asn Arg Trp Ala Asp Leu
305                 310                 315                 320

Gly Ile Glu Leu Leu Tyr Gln Glu Arg Ile Gly His Asp Asp Lys Ser
                325                 330                 335

<210> SEQ ID NO 20
<211> LENGTH: 317
<212> TYPE: PRT
<213> ORGANISM: Streptococcus pneumonia

<400> SEQUENCE: 20

Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
                20                  25                  30

Ser Ser Ile Ser Leu Thr Leu Glu Asn Met Tyr Thr Glu Thr Thr Leu
            35                  40                  45

Ser Pro Leu Pro Ala Asn Val Thr Ala Asp Glu Phe Tyr Ile Asn Gly
    50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285

Asp Leu Glu His Leu Ser Glu Ile Phe Gly Arg Tyr Arg Leu Ile
    290                 295                 300

Val Ser Lys Thr Lys Asp Leu Ser Gln Asp Asp Cys Cys
305                 310                 315

<210> SEQ ID NO 21
```

```
<211> LENGTH: 182
<212> TYPE: PRT
<213> ORGANISM: escherichia coli

<400> SEQUENCE: 21

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

Thr Arg Arg Ala Leu Ser Lys Lys Ala Trp Pro Gly Val Trp Thr Asn
50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 22
<211> LENGTH: 149
<212> TYPE: PRT
<213> ORGANISM: Corynebacterium glutamicum

<400> SEQUENCE: 22

Met Ile Pro Ile Ile Asp Ile Ser Gln Asn Glu Gln Asp Ser Asp Ile
1               5                   10                  15

Phe Met Ala Phe Ile Tyr Leu Gly Thr Leu Leu Val Leu Ile Gly Cys
            20                  25                  30

Met Ala Leu Cys Asp His Arg Trp Lys Leu Ala Phe Phe Arg His Pro
        35                  40                  45

Leu Arg Ala Ile Leu Ser Val Gly Ala Ala Tyr Ile Gly Phe Leu Leu
    50                  55                  60

Trp Asp Ile Phe Gly Ile Ile Thr Gly Thr Phe Tyr Arg Gly Asp Ser
65                  70                  75                  80

Ala Phe Met Ser Gly Ile Asn Leu Ala Pro His Met Pro Ile Glu Glu
                85                  90                  95

Leu Phe Phe Leu Phe Phe Leu Cys Tyr Ile Thr Leu Asn Leu Thr Ser
            100                 105                 110

Ala Ala Ala Leu Trp Leu Lys Ala Pro Leu Pro Lys Lys Pro Gly Lys
        115                 120                 125

Lys Ser Pro Leu Thr Pro Gln Arg Asp Thr Phe Gln Pro Thr Thr Thr
    130                 135                 140

Pro Glu Val Glu Pro
145
```

<210> SEQ ID NO 23
<211> LENGTH: 130
<212> TYPE: PRT
<213> ORGANISM: Corynebacterium glutamicum

<400> SEQUENCE: 23

Met Thr Tyr Ile Phe Ile Ser Ile Pro Phe Leu Ala Ile Ala Met Val
1               5                   10                  15

Leu Phe Val Leu Lys Leu Gln Ser Gly Thr Pro Lys Leu Leu Pro Ile
            20                  25                  30

Thr Ala Val Ser Ala Leu Thr Leu Cys Ser Leu Thr Ile Ile Phe Asp
        35                  40                  45

Asn Leu Met Val Trp Ala Asp Leu Phe Gly Tyr Gly Asp Thr Gln His
    50                  55                  60

Leu Gly Ile Trp Leu Gly Leu Ile Pro Leu Glu Asp Leu Phe Tyr Pro
65                  70                  75                  80

Leu Phe Ala Val Leu Leu Ile Pro Ala Leu Trp Leu Pro Gly Asn Met
                85                  90                  95

Phe Lys Arg Arg Lys Lys Arg Pro His His Ser Leu Pro Thr Ile Ala
            100                 105                 110

Asn Gly Ser Ile Thr Thr Arg Ser Thr Thr Thr Gln Ser Glu Pro Glu
        115                 120                 125

Lys Pro
    130

<210> SEQ ID NO 24
<211> LENGTH: 287
<212> TYPE: PRT
<213> ORGANISM: Corynebacterium glutamicum

<400> SEQUENCE: 24

Met Met Glu Lys Ile Arg Leu Ile Leu Leu Ser Ser Arg Pro Ile Ser
1               5                   10                  15

Trp Ile Asn Thr Ala Tyr Pro Phe Gly Leu Ala Tyr Leu Leu Asn Ala
            20                  25                  30

Gly Glu Ile Asp Trp Leu Phe Trp Leu Gly Ile Val Phe Leu Ile
        35                  40                  45

Pro Tyr Asn Ile Ala Met Tyr Gly Ile Asn Asp Val Phe Asp Tyr Glu
    50                  55                  60

Ser Asp Met Arg Asn Pro Arg Lys Gly Gly Val Glu Gly Ala Val Leu
65                  70                  75                  80

Pro Lys Ser Ser His Ser Thr Leu Leu Trp Ala Ser Ala Ile Ser Thr
                85                  90                  95

Ile Pro Phe Leu Val Ile Leu Phe Ile Phe Gly Thr Trp Met Ser Ser
            100                 105                 110

Leu Trp Leu Thr Leu Ser Val Leu Ala Val Ile Ala Tyr Ser Ala Pro
        115                 120                 125

Lys Leu Arg Phe Lys Glu Arg Pro Phe Ile Asp Ala Leu Thr Ser Ser
    130                 135                 140

Thr His Phe Thr Ser Pro Ala Leu Ile Gly Ala Thr Ile Thr Gly Thr
145                 150                 155                 160

Ser Pro Ser Ala Ala Met Trp Ile Ala Leu Gly Ser Phe Phe Leu Trp
                165                 170                 175

Gly Met Ala Ser Gln Ile Leu Gly Ala Val Gln Asp Val Asn Ala Asp
            180                 185                 190

```
Arg Glu Ala Asn Leu Ser Ser Ile Ala Thr Val Ile Gly Ala Arg Gly
        195                 200                 205

Ala Ile Arg Leu Ser Val Val Leu Tyr Leu Leu Ala Ala Val Leu Val
    210                 215                 220

Thr Thr Leu Pro Asn Pro Ala Trp Ile Ile Gly Ile Ala Ile Leu Thr
225                 230                 235                 240

Tyr Val Phe Asn Ala Ala Arg Phe Trp Asn Ile Thr Asp Ala Ser Cys
                245                 250                 255

Glu Gln Ala Asn Arg Ser Trp Lys Val Phe Leu Trp Leu Asn Tyr Phe
            260                 265                 270

Val Gly Ala Val Ile Thr Ile Leu Leu Ile Ala Ile His Gln Ile
        275                 280                 285

<210> SEQ ID NO 25
<211> LENGTH: 1578
<212> TYPE: DNA
<213> ORGANISM: saccharomyces cerevisiae

<400> SEQUENCE: 25
```

| | | | | |
|---|---|---|---|---|
| atggaccaat | tggtgaaaac | tgaagtcacc | aagaagtctt | ttactgctcc tgtacaaaag | 60 |
| gcttctacac | cagttttaac | caataaaaca | gtcatttctg | gatcgaaagt caaaagttta | 120 |
| tcatctgcgc | aatcgagctc | atcaggacct | tcatcatcta | gtgaggaaga tgattcccgc | 180 |
| gatattgaaa | gcttggataa | gaaaatacgt | cctttagaag | aattagaagc attattaagt | 240 |
| agtggaaata | caaacaatt | gaagaacaaa | gaggtcgctg | ccttggttat tcacggtaag | 300 |
| ttacctttgt | acgctttgga | gaaaaaatta | ggtgatacta | cgagagcggt tgcggtacgt | 360 |
| aggaaggctc | tttcaatttt | ggcagaagct | cctgtattag | catctgatcg tttaccatat | 420 |
| aaaaattatg | actacgaccg | cgtatttggc | gcttgttgtg | aaaatgttat aggttacatg | 480 |
| cctttgcccg | ttggtgttat | aggccccttg | gttatcgatg | gtacatctta tcatatacca | 540 |
| atggcaacta | cagagggttg | tttggtagct | tctgccatgc | gtggctgtaa ggcaatcaat | 600 |
| gctggcggtg | gtgcaacaac | tgttttaact | aaggatggta | tgacaagagg cccagtagtc | 660 |
| cgtttcccaa | ctttgaaaag | atctggtgcc | tgtaagatat | ggttagactc agaagaggga | 720 |
| caaaacgcaa | ttaaaaaagc | ttttaactct | acatcaagat | tgcacgtctc gcaacatatt | 780 |
| caaacttgtc | tagcaggaga | tttactcttc | atgagattta | gaacaactac tggtgacgca | 840 |
| atgggtatga | atatgatttc | taaaggtgtc | gaatactcat | taaagcaaat ggtagaagag | 900 |
| tatggctggg | aagatatgga | ggttgtctcc | gtttctggta | actactgtac cgacaaaaaa | 960 |
| ccagctgcca | tcaactggat | cgaaggtcgt | ggtaagagtg | tcgtcgcaga agctactatt | 1020 |
| cctggtgatg | ttgtcagaaa | agtgttaaaa | agtgatgttt | ccgcattggt tgagttgaac | 1080 |
| attgctaaga | atttggttgg | atctgcaatg | gctgggtctg | ttggtggatt taacgcacat | 1140 |
| gcagctaatt | tagtgacagc | tgtttttctg | gcattaggac | aagatcctgc acaaaatgtt | 1200 |
| gaaagttcca | actgtataac | attgatgaaa | gaagtggacg | tgatttgag aatttccgta | 1260 |
| tccatgccat | ccatcgaagt | aggtaccatc | ggtggtggta | ctgttctaga accacaaggt | 1320 |
| gccatgttgg | acttattagg | tgtaagaggc | ccgcatgcta | ccgctcctgg taccaacgca | 1380 |
| cgtcaattag | caagaatagt | tgcctgtgcc | gtcttggcag | gtgaattatc cttatgtgct | 1440 |
| gccctagcag | ccggccattt | ggttcaaagt | catatgaccc | acaacaggaa acctgctgaa | 1500 |
| ccaacaaaac | ctaacaattt | ggacgccact | gatataaatc | gtttgaaaga tgggtccgtc | 1560 | acctgcatta aatcctaa                                                 1578

<210> SEQ ID NO 26
<211> LENGTH: 924
<212> TYPE: DNA
<213> ORGANISM: Pantoea agglomerans

<400> SEQUENCE: 26

```
atggtgagtg gcagtaaagc gggcgtttcg cctcatcgcg aaatagaagt aatgagacaa      60
tccattgacg atcacctggc tggcctgtta cctgaaaccg acagccagga tatcgtcagc     120
cttgcgatgc gtgaaggcgt catggcaccc ggtaaacgga tccgtccgct gctgatgctg     180
ctggccgccc gcgacctccg ctaccagggc agtatgccta cgctgctcga tctcgcctgc     240
gccgttgaac tgacccatac cgcgtcgctg atgctcgacg acatgccctg catggacaac     300
gccgagctgc gccgcggtca gcccactacc cacaaaaaat tggtgagag cgtggcgatc      360
cttgcctccg ttgggctgct ctctaaagcc tttggtctga tcgccgccac cggcgatctg     420
ccgggggaga ggcgtgccca ggcggtcaac gagctctcta ccgccgtggg cgtgcagggc     480
ctggtactgg ggcagtttcg cgatcttaac gatgccgccc tcgaccgtac ccctgacgct     540
atcctcagca ccaaccacct caagaccggc attctgttca gcgcgatgct gcagatcgtc     600
gccattgctt ccgcctcgtc gccgagcacg cgagagacgc tgcacgcctt cgccctcgac     660
ttcggccagg cgtttcaact gctggacgat ctgcgtgacg atcacccgga aaccggtaaa     720
gatcgcaata aggacgcggg aaaatcgacg ctggtcaacc ggctgggcgc agacgcggcc     780
cggcaaaagc tgcgcgagca tattgattcc gccgacaaac acctcacttt tgcctgtccg     840
cagggcggcg ccatccgaca gtttatgcat ctgtggtttg gccatcacct tgccgactgg     900
tcaccggtca tgaaaatcgc ctga                                            924
```

<210> SEQ ID NO 27
<211> LENGTH: 906
<212> TYPE: DNA
<213> ORGANISM: Synechocystis sp. PCC6803

<400> SEQUENCE: 27

```
atggttgccc aacaaacacg aaccgacttt gatttagccc aatacttaca agttaaaaaa      60
ggtgtggtcg aggcagccct ggatagttcc ctggcgatcg cccggccgga aaagatttac     120
gaagccatgc gttattctct gttggcgggg ggcaaacgat tgcgaccgat tttatgcatt     180
acggcctgcg aactgtgtgg cggtgatgaa gccctggcct tgcccacggc ctgtgccctg     240
gaaatgatcc acaccatgtc cctcatccat gatgatttgc cctccatgga taatgacgat     300
ttccgccggg gtaaacccac taaccacaaa gtgtacgggg aagacattgc cattttggcc     360
ggggatggac tgctagccta tgcgtttgag tatgtagtta cccacacccc ccaggctgat     420
ccccaagctt tactccaagt tattgcccgt ttgggtcgca cggtggggc cgccggttta     480
gtgggggac aagttctaga cctggaatcg gaggggcgca ctgacatcac cccggaaacc     540
ctaacttta tccatacccca taaaaccggg gcattgctgg aagcttccgt gctcacaggc     600
gcaattttgg ccggggccac tgggaacaa caacagagac tggcccgcta tgcccagaat     660
attggcttag cttttcaagt ggtggatgac atcctcgaca tcaccgccac ccaggaagag     720
ttgggtaaaa ccgctggtaa agatgtcaaa gcccaaaaag ccacctatcc cagtctcctc     780
ggtttggaag cttcccgggc ccaggcccaa agtttgattg accaggccat tgtcgccctg     840
gaaccctttg gccccctccgc cgagcccctc caggcgatcg ccgaatatat tgttgccaga     900
``` aaatat 906

<210> SEQ ID NO 28
<211> LENGTH: 930
<212> TYPE: DNA
<213> ORGANISM: Pantoea agglomerans

<400> SEQUENCE: 28

```
atgagccaac cgccgctgct tgaccacgcc acgcagacca tggccaacgg ctcgaaaagt    60
tttgccaccg ctgcgaagct gttcgacccg gccacccgcc gtagcgtgct gatgctctac   120
acctggtgcc gccactgcga tgacgtcatt gacgaccaga cccacggctt cgccagcgag   180
gccgcggcgg aggaggaggc cacccagcgc ctggcccggc tgcgcacgct gaccctggcg   240
gcgtttgaag gggccgagat gcaggatccg gccttcgctg cctttcagga ggtggcgctg   300
acccacggta ttacgccccg catggcgctc gatcacctcg acggctttgc gatggacgtg   360
gctcagaccc gctatgtcac ctttgaggat acgctgcgct actgctatca cgtgcgggc   420
gtggtgggtc tgatgatggc cagggtgatg ggcgtgcggg atgagcgggt gctggatcgc   480
gcctgcgatc tggggctggc cttccagctg acgaatatcg cccgggatat tattgacgat   540
gcggctattg accgctgcta tctgcccgcc gagtggctgc aggatgccgg gctgaccccg   600
gagaactatg ccgcgcggga gaatcgggcc gcgctggcgc gggtggcgga gcggcttatt   660
gatgccgcag agccgtacta catctcctcc caggccgggc tacacgatct gccgccgcgc   720
tgcgcctggg cgatcgccac cgcccgcagc gtctaccggg agatcggtat taaggtaaaa   780
gcggcgggag gcagcgcctg ggatcgccgc cagcacacca gcaaaggtga aaaaattgcc   840
atgctgatgg cggcaccggg gcaggttatt cgggcgaaga cgacgagggt gacgccgcgt   900
ccggccggtc tttggcagcg tcccgtttag                                    930
```

<210> SEQ ID NO 29
<211> LENGTH: 1479
<212> TYPE: DNA
<213> ORGANISM: Pantoea agglomerans

<400> SEQUENCE: 29

```
atgaaaaaaa ccgttgtgat tggcgcaggc tttggtggcc tggcgctggc gattcgcctg    60
caggcggcag ggatcccaac cgtactgctg gagcagcggg acaagcccgg cggtcgggcc   120
tacgtctggc atgaccaggg cttaccttt gacgccgggc cgacggtgat caccgatcct   180
accgcgcttg aggcgctgtt caccctggcc ggcaggcgca tggaggatta cgtcaggctg   240
ctgccggtaa aacccttcta ccgactctgc tgggagtccg ggaagaccct cgactatgct   300
aacgacagcg ccgagcttga ggcgcagatt acccagttca accccgcga cgtcgagggc   360
taccggcgct ttctggctta ctcccaggcg gtattccagg agggatattt cgcctcggc   420
agcgtgccgt tcctctcttt cgcgacatg ctgcgcgccg gccgcagct gcttaagctc   480
caggcgtggc agagcgtcta ccagtcggtt tcgcgcttta ttgaggatga gcatctgcgg   540
caggccttct cgttccactc cctgctggta ggcggcaacc ccttcaccac ctcgtccatc   600
tacacccctga tccacgccct tgagcgggag tgggggggtct ggttccctga gggcggcacc   660
ggggcgctgg tgaacggcat ggtgaagctg tttaccgatc tgggcgggga gatcgaactc   720
aacgcccggg tcgaagagct ggtggtggcc gataaccgcg taagccaggt ccggctggcg   780
gatggtcgga tctttgacac cgacgccgta gcctcgaacg ctgacgtggt gaacacctat   840
```

| | |
|---|---|
| aaaaagctgc tcggccacca tccggtgggg cagaagcggg cggcagcgct ggagcgcaag | 900 |
| agcatgagca actcgctgtt tgtgctctac ttcggcctga accagcctca ttcccagctg | 960 |
| gcgcaccata ccatctgttt tggtccccgc taccgggagc tgatcgacga gatctttacc | 1020 |
| ggcagcgcgc tggcggatga cttctcgctc tacctgcact cgccctgcgt gaccgatccc | 1080 |
| tcgctcgcgc ctcccggctg cgccagcttc tacgtgctgg ccccggtgcc gcatcttggc | 1140 |
| aacgcgccgc tggactgggc gcaggagggg ccgaagctgc gcgaccgcat ctttgactac | 1200 |
| cttgaagagc gctatatgcc cggcctgcgt agccagctgg tgacccagcg gatctttacc | 1260 |
| ccggcagact tccacgacac gctggatgcg catctgggat cggccttctc catcgagccg | 1320 |
| ctgctgaccc aaagcgcctg gttccgcccg cacaaccgcg acagcgacat tgccaacctc | 1380 |
| tacctggtgg cgcaggtac tcaccctggg gcgggcattc ctggcgtagt ggcctcggcg | 1440 |
| aaagccaccg ccagcctgat gattgaggat ctgcaatga | 1479 |

<210> SEQ ID NO 30
<211> LENGTH: 1533
<212> TYPE: DNA
<213> ORGANISM: Rhodopseudomonas palustris

<400> SEQUENCE: 30

| | |
|---|---|
| atgctcgatc ctggccccaa tcctgctccc cgtccttctc gcgatcgtgc cccgcatgcg | 60 |
| gtggtgatcg gctctggttt cggcggcttg gccgcagcgg tgcgtcttgg cgccaagggg | 120 |
| tatcgagtaa ccgttcttga aaagctcgat aaggccggcg ccgcgctta cgtccacaag | 180 |
| caggacggct tctcattcga cgccggtccg accatcgtca ccgcgccgta tctgttcgaa | 240 |
| gagctgtgga agctgtgcgg caagcggatg tcggacgaca tcaccttgaa gccgatgtcg | 300 |
| ccgttctatc gcatccgctt cgacgacggc acgcacttcg attactccga cgaccgcgac | 360 |
| gcggtgctcg accagatcgc caagttctgc ccggacgacg tgccggccta tgaccgcttc | 420 |
| atggcggcct cgcacgagat tttcaaagtc ggtttcgagc agctcggcga tcagccattc | 480 |
| agtcacttca ccgacatgct gaagatcgcg ccggcgatga tcaagctgga gagctatcgc | 540 |
| agcgtttacg gcctcgtcgc caagcacttc aaggatccga agctgcgcca ggtgttcagc | 600 |
| ttccatccgc tgctgatcgg cggcaacccg ttcatgtcca gctcggtgta ctgcctgatc | 660 |
| acctatctgg aaaagcagtg gggcgtgcat tcagcgatgg gcggcaccgg cgcgctcgtc | 720 |
| accggtctgg tcaacctgat cgagggccag ggcaatacga tccgctacaa tcaggatgtc | 780 |
| cgccagatcg tcgtggaaaa cggcaccgcg tgcggcgtca gctcgccga tggcgaggtg | 840 |
| attaaggccg atatcgtggt gtccaacgcc gattcggcct cgacttatcg ctatctgctg | 900 |
| ccgccggaga cgcgcaagcg ttggaccgac gccaagatcg agaagtcgcg ctattcgatg | 960 |
| agcctattcg tctggtactt cggcacgaag cgtcgctacg aagacgtcaa gcaccacacc | 1020 |
| attctgctcg accgcgcta caaggaactg atcagcgaca tcttcagccg gaaggtggtc | 1080 |
| gccgaggatt tcagcctgta tctgcatcgc ccgactgcga ccgaccgtc gctcgcgccg | 1140 |
| cagggctgcg acactttcta cgtcctgtcg ccggtgccga atctgctcgg tgatactgat | 1200 |
| tggcacacca aggccgagac ttatcgcgcc tcgatcgcca agatgctcgg tgcgaccgtt | 1260 |
| ctgcccgatc tggaaaacca gatcgcgacc tccaagatca ccacgccgat cgatttccag | 1320 |
| gaccggctgt cgtcgttccg cggcgcggcg ttcggtctgg agccggtgtt gtggcagagc | 1380 |
| gcctggttca ggccgcacaa tcagagcgaa gacgtcaaac gcctttatct cgtcggcgcc | 1440 |
| ggaacgcatc ccggcgctgg cctgcccggg gtactgtcct cggcgcgggt actcgatgcg | 1500 |

```
ctggtccccg aggccgacag tctggtgaca tca                                 1533
```

<210> SEQ ID NO 31
<211> LENGTH: 1146
<212> TYPE: DNA
<213> ORGANISM: Pantoea ananatis

<400> SEQUENCE: 31

```
atgcaaccgc attatgatct gattctcgtg ggggctggac tcgcgaatgg ccttatcgcc     60
ctgcgtcttc agcagcagca acctgatatg cgtattttgc ttatcgacgc cgcaccccag    120
gcgggcggga atcatacgtg gtcatttcac cacgatgatt tgactgagag ccaacatcgt    180
tggatagctc cgctggtggt tcatcactgg cccgactatc aggtacgctt tcccacacgc    240
cgtcgtaagc tgaacagcgg ctactttgt attacttctc agcgtttcgc tgaggtttta    300
cagcgacagt ttggcccgca cttgtggatg ataccgcgg tcgcagaggt taatgcggaa    360
tctgttcggt tgaaaaaggg tcaggttatc ggtgcccgcg cggtgattga cgggcgggt    420
tatgcggcaa attcagcact gagcgtgggc ttccaggcgt ttattggcca ggaatggcga    480
ttgagccacc cgcatggttt atcgtctccc attatcatgg atgccacggt cgatcagcaa    540
aatggttatc gcttcgtgta cagcctgccg ctctcgccga ccagattgtt aattgaagac    600
acgcactata ttgataatgc gacattagat cctgaatgcg cgcggcaaaa tatttgcgac    660
tatgccgcgc aacagggttg gcagcttcag acactgctgc gagaagaaca gggcgcctta    720
cccattactc tgtcgggcaa tgccgacgca ttctggcagc agcgcccct ggcctgtagt    780
ggattacgtg ccggtctgtt ccatcctacc accggctatt cactgccgct ggcggttgcc    840
gtggccgacc gctgagtgc acttgatgtc tttacgtcgg cctcaattca ccatgccatt    900
acgcattttg cccgcgagcg ctggcagcag cagggctttt ccgcatgct gaatcgcatg    960
ctgttttta g ccggacccgc cgattcacgc tggcgggtta tgcagcgttt ttatggttta   1020
cctgaagatt taattgcccg ttttatgcg ggaaaactca cgctgaccga tcggctacgt    1080
attctgagcg gcaagccgcc tgttccggta ttagcagcat tgcaagccat tatgacgact   1140
catcgt                                                              1146
```

<210> SEQ ID NO 32
<211> LENGTH: 828
<212> TYPE: DNA
<213> ORGANISM: uncultured marine bacterium 66A03

<400> SEQUENCE: 32

```
atgggtctga tgctgattga ttggtgtgca ctggctctgg ttgttttcat tggcctgccg     60
cacggcgcgc tggatgctgc catttctttt tctatgatct cttctgcaaa acgcattgct    120
cgtctggctg gtattctgct gatctatctg ctgctggcga ccgcgttctt cctgatctgg    180
tatcagctgc cagcgtttag cctgctgatc ttcctgctga tctccattat ccactttggt    240
atggcagact tcaacgcgtc cccaagcaaa ctgaaatggc cgcatatcat cgcccacggc    300
ggtgttgtta ctgtttggct gccgctgatc cagaaaaacg aagtaactaa actgtttagc    360
atcctgacta acggtccgac tccgatcctg tgggacatcc tgctgatttt cttcctgtgt    420
tggtctattg gcgtgtgtct gcacacgtac gaaaccctgc gctctaaaca ttacaacatc    480
gcctttgaac tgatccggtct gattttcctg gcgtggtatg cgccgcctct ggttacgttt    540
gccacttact tctgcttcat tcattcccgt cgccacttct cctttgtgtg gaagcagctg    600
```

| | |
|---|---|
| caacacatgt cttccaaaaa gatgatgatt ggcagcgcga ttatcctgtc ctgtacctct | 660 |
| tggctgatcg gcggtggtat ctatttcttc ctgaactcca aaatgatcgc ctctgaggct | 720 |
| gcgctgcaga ctgtgttcat cggtctggcg gcactgaccg tgccgcacat gattctgatc | 780 |
| gacttcatct tccgtccgca ctcttcccgt atcaaaatca aaaactaa | 828 |

<210> SEQ ID NO 33
<211> LENGTH: 1041
<212> TYPE: DNA
<213> ORGANISM: Cronobacter sakazakii

<400> SEQUENCE: 33

| | |
|---|---|
| atgaaggaca aggaactgag ccaacgcaag aacgatcatc tggatatcgt tctgcacccg | 60 |
| gagcgggcta acaaacgat tcgcaccggc tttgagcagt ggcgttttga gcactgcgcc | 120 |
| ctgccggaac tcgcgcttga cgacatcgat ctcagcaccc gctgtttgg ccgcgtgatg | 180 |
| aaagcgccgc ttctgattag ctccatgacc ggcggtgcgc ggcgcgcgag cgatatcaac | 240 |
| cgtcacctcg ccgaagccgc gcagacgctg gggctggcga tgggcgtcgg ctcgcagcgt | 300 |
| gtggcgctgg agagcgaaga caactggggg ctgacgggcg aactgcgccg gtacgcgccg | 360 |
| gatattccgc tgctggcgaa tctcggggcc gcgcagatag gcagcctcca ggggctcgat | 420 |
| tacgcccgac gcgccgtcga gatggtggaa gccgacgcgc tcattattca tcttaatccg | 480 |
| ttgcaggaag cgctccagac tggcggcgat gcgcgactgg gcggcgtgtt ggcagccatc | 540 |
| aagcgcgtcg taaacgcact gtccgtgccg gtggtggtga agaagtcgg cgccgggctc | 600 |
| tcggtgccgg tggcgcgcca gcttgcggag gcaggcgtca cgatgctgga tgtggcaggc | 660 |
| gcaggcggca ccagctgggc ggccgtggaa ggtgaacgcg cggcgagcga ccatgcccgt | 720 |
| agcgtggcga tggccttcgc cgactggggc atacccaccg cgcaggcgct gcgccagata | 780 |
| catcaggcat tcccgtcgat gccgcttatc gcctctggcg gcattcgcga cggtatcgac | 840 |
| accgccaaag ccctggcgat gggcgcaagt tcgtcgggc aggccgcggc ggtgctcggc | 900 |
| agcgcgacca cctccaccag cgcggtgctg gaccatttcg cagtcgtgat tgaacagttg | 960 |
| cgggtcgcct gttttgcac cggcagcgcc agcctcagcg cgctgcgtga ggcccggctg | 1020 |
| gcgcgcgtcg gggatgagga a | 1041 |

<210> SEQ ID NO 34
<211> LENGTH: 1149
<212> TYPE: DNA
<213> ORGANISM: Corynebacterium glutamicum

<400> SEQUENCE: 34

| | |
|---|---|
| ttgcgagata actggccgtg tgatactcga atggacaatg gcatgacaat caccacagaa | 60 |
| cattcaactc atcctgatct tgatttcaat gatgagattt atcgggaact aaaccgcatc | 120 |
| tgcgcttcgc tatctcaaca gtgcagcaca tatcaaccag agttccgtac ctgcctagat | 180 |
| gctgcttttcc aagctttgcg aggtggcaag ttaatccgcc ctcgaatgct actggggcta | 240 |
| tacaacacgc ttgtagacga tgacattgag gtcaaactca acaccgtttt acaggtagca | 300 |
| gtggctttag aactactgca ttttttccctt ttggttcatg acgatgttat tgacggagac | 360 |
| ctctatcgcc gaggcaaact taattttatt ggcagattc tcatgcatcg cacacctgaa | 420 |
| agttttgcac aaatccagcg cgatccagag catctagatt gggcacaatc taatggactg | 480 |
| cttatgggaa atcttttttct tgctgccacc catcaaatct tcgcgcgcct tgaccttcca | 540 |
| catcaccaac gggttcgact tttagattta ctcaaccaca cgataaatga cactattgtg | 600 |

```
ggtgagtttc ttgatgtggg attaagcagc aaagccatca gccccaatat ggacattgct    660
ctagaaatga gtcggctaaa aacagccaca tacacttttg aacttccaat gagagcagcg    720
gcaattctcg cggaactacc tcaggagatt gaaacaaaga taggtgagat aggcacaaac    780
ttgggcatcg cttatcaatt gcaggacgat tacttatcta cttttggtga cgcagccgaa    840
cacggcaaag atgccttttc tgaccttcga gaaggaaaag aaactacaat tatcgccttc    900
gctcgagata ctgctaaatg gactgatatt caagacaact tcggctccgc agatctgagc    960
acctctcagg cagagcgaat tcaacatctt ctcatacagt gtggagcaaa gaatcactcc   1020
ttgaatgcca tctccgacca cttaaatatc tgccgttcga tgatcaaaac actaagcccc   1080
caggtagatc ccaaggctca aaatttatta cttaaacaag ttgagcaact agccagccgc   1140
aaatcttag                                                           1149
```

<210> SEQ ID NO 35
<211> LENGTH: 915
<212> TYPE: DNA
<213> ORGANISM: Corynebacterium glutamicum

<400> SEQUENCE: 35

```
atgacacacc aaaattcgcc tctcttcctt aaaagtgcac tgagacttta caatcgggcc     60
tcattcaagg cttcacataa agtgatcgaa gaatattcga cgagcttcag tctgtctacg    120
tggttgctat ccccacgcat acgaaatgac atacgaaatc tctatgcagt agttcgtatc    180
gccgatgaga ttgtcgacgg cactgcacat gccgctggtt gctcaactgc caaaatcgaa    240
gagattctcg atgcctatga aattgcggtt cttgcagcac cacaacaacg cttcaacaca    300
gatcttgttt tacaagctta tggtgaaact gcccgacgct gtgatttcga acaagagcat    360
gtaatagcct tctttgcatc aatgcgtaag gacctcaaag ctaatacaca cgacccagat    420
agcttcacaa cgtatgtcta tggctccgcg gaagttatag gcctgctttg tctcagcgtt    480
ttcaaccaag gtagaacgat tagcaaaaaa cggctagaga ttatgcaaaa cggagcccgc    540
tcattgggag cggcattcca gaaaattaac tttctccgtg acttggcaga agatcagcaa    600
aatttgggcc gattttattt ccccaaaacc agccaaggaa ctcttactaa agaacaaaaa    660
gaagatctca tcgctgatat ccgtcaagac ctagcaattg cccacgatgc atttccagaa    720
ataccagtgc aggctcgcat cggagtgatc tctgcttatt tgctctttca aaaactcact    780
gaccgaattg aggctactcc taccgccgat ttattgcggg agcgaatcag agttccactt    840
catatcaaac tctctacact cgctagagcc acgatgaaag gtctatctat gagcatctac    900
agaaagaatt cgtga                                                    915
```

<210> SEQ ID NO 36
<211> LENGTH: 1647
<212> TYPE: DNA
<213> ORGANISM: Corynebacterium glutamicum

<400> SEQUENCE: 36

```
atgaaggtct cgactaaaac tccacgctcc tcaggtaccg ccgtagtcat aggcgcaggt     60
gttgctggtt tagccacttc tgcactttta gcacgtgatg ctggcaagt aactgttttg    120 gaaaaaaata ctgatgtcgg tggccgagct ggatcgcttg aaatatcagg ctttcctggc    180
tttcgatggg ataccggacc tcttggtac ctcatgcccg aggcctttga ccatttcttc    240
gcactttttg gtgcatgtac ttctgattat ctcgatttgg tagaattaac gcctggttat    300
```

```
cgagtttttt ctggcacaca tgacgctgtc gatgtcccca ctgggcgtga agaagcaatt      360
gcgctattcg aatccatcga acccggcgcg ggtgcaaaac taggaaatta tcttgatagc      420
gcggcagacg cctatgacat tgccattgat agattccttt ataataattt ctccacgtta      480
ggcccgctgc ttcaccggga tgtactgacc cgagctggcc gactgttttc tctactgacc      540
cgttctttac aaaagtacgt aaatagtcaa ttcagtagcc cggtgttgcg ccagatccta      600
acctatccag cagtcttcct gtcttcccga cccactacta ccccatcgat gtaccacttg      660
atgagtcata ccgatttggt gcagggagtg aaatacccta taggtggttt tactgcagtg      720
gttaacgctc tgcatcagtt agcgctggaa acgggggttg agtttcaact cgattctgag      780
gtcatttcca tcaacactgc ttcatcgagg ggcaacacaa gcgccacagg tgtgagcttg      840
cttcacaaca gaaagtgca aaatctagat gcggatcttg tggtttcagc aggcgaccta      900
caccatacag aaaataatct gcttccccgg gaacttcgaa cctatcccga acgatattgg      960
tccaatcgca atcctggaat tggagcggta ttaatcctcc tgggcgtaaa aggagagtta     1020
ccccagctcg accatcacaa cctttcttc agtgaagatt ggacagatga ttttgctgta     1080
gttttcgacg ggcctcaact tacccgcccc cacaatgcat caaattccat ttatgtctcc     1140
aagccttcaa cgtccgaaga cggcgttgca cctgctggat acgaaaacct ttttgtttta     1200
attccgacca aggcctctag cagcatcggc cacggtgatg cgtatatgca gtcggcttca     1260
gcatccgtgg aaacaatcgc gtcacatgca atcaatcaaa ttgctacgca agccggcatc     1320
cctgacctca ctgaccgaat tgtggtcaaa cgcaccattg gccctgcgga ttttgagcac     1380
cgctaccatt catgggtagg cagtgcgctg ggtccagcac ataccctcag acagtccgct     1440
ttcttaagag ggcgcaatag ctcccgcaag gtcaataacc tcttctattc cggtgccacc     1500
accgtcccgg gtgtaggaat acccatgtgt ttaatttctg ccgagaatat tattaagcgt     1560
ttacatgccg ataccagtgc aggaccactg cccgaaccat tgccgcctaa aacgacacca     1620
tctcaaaaga cctcatacga tcattaa                                         1647
```

<210> SEQ ID NO 37
<211> LENGTH: 588
<212> TYPE: DNA
<213> ORGANISM: Corynebacterium glutamicum

<400> SEQUENCE: 37

```
ttactctgcg tcaaacgctt ccaggatggc ttggcgcagc tcaggggcgc taagctgatc       60
cactagccat ggagaaaaca caaatggtgt ggcatcaaca gcgtcgaaaa gcttctgcgg      120
ttccgcccac tcgaactcct ccacctcatc atccagtggc tccacaaatt cccccaccgc      180
taaacgcacg aggtggaccg ggcacaactc ccactccaca atgccggacg cgtcgacagc      240
acggtactgg taatcaggca gaatctcttg aatatccaag aaagaatcta cctccagccc      300
caactcatcg acaccctgc gacgaatcgc atccgcgttt gtctcatccg gaccagggtg      360
cccacacata gagttcgtcc acacaccagg ccatgtcttc ttcgacaatg cacgacgcgt      420
caccaacagc tccccacgcg ggttcaaaat ataggtggaa aacgcgaaat gcagaggcgt      480
gtccttagtg tgcaccgtag ctttcggcgc agtaccaata ggattgccct cggaatcagc      540
taaaacaacc agttcaacct cagtagtcat gcccctaagc ttagacac                  588
```

<210> SEQ ID NO 38
<211> LENGTH: 1881
<212> TYPE: DNA
<213> ORGANISM: escherichia coli

<400> SEQUENCE: 38

```
atggaattca ggaggcccct gatgagtttt gatattgcca atacccgac cctggcactg      60
gtcgactcca cccaggagtt acgactgttg ccgaaagaga gtttaccgaa actctgcgac    120
gaactgcgcc gctatttact cgacagcgtg agccgttcca gcgggcactt cgcctccggg    180
ctgggcacgg tcgaactgac cgtggcgctg cactatgtct acaacacccc gtttgaccaa    240
ttgatttggg atgtggggca tcaggcttat ccgcataaaa ttttgaccgg acgccgcgac    300
aaaatcggca ccatccgtca gaaaggcggt ctgcacccgt tcccgtggcg cggcgaaagc    360
gaatatgacg tattaagcgt cgggcattca tcaacctcca tcagtgccgg aattggtatt    420
gcggttgctg ccgaaaaaga aggcaaaaat cgccgcaccg tctgtgtcat tggcgatggc    480
gcgattaccg caggcatggc gtttgaagcg atgaatcacg cgggcgatat ccgtcctgat    540
atgctggtga ttctcaacga caatgaaatg tcgatttccg aaaatgtcgg cgcgctcaac    600
aaccatctgg cacagctgct ttccggtaag ctttactctt cactgcgcga aggcgggaaa    660
aaagtttttct ctggcgtgcc gccaattaaa gagctgctca acgcaccga gaacatatt    720
aaaggcatgg tagtgcctgg cacgttgttt gaagagctgg gctttaacta catcggcccg    780
gtggacggtc acgatgtgct ggggcttatc accacgctaa gaacatgcg cgacctgaaa    840
ggcccgcagt cctgcatat catgaccaaa aaggtcgtg gttatgaacc ggcagaaaaa    900
gacccgatca ctttccacgc cgtgcctaaa tttgatccct ccagcggttg tttgccgaaa    960
agtagcggcg gtttgccgag ctattcaaaa atctttggcg actggttgtg cgaaacggca   1020
gcgaaagaca acaagctgat ggcgattact ccggcgatgc gtgaaggttc cggcatggtc   1080
gagttttcac gtaaattccc ggatcgctac ttcgacgtgg caattgccga gcaacacgcg   1140
gtgacctttg ctgcgggtct ggcgattggt gggtacaaac ccattgtcgc gatttactcc   1200
actttcctgc aacgcgccta tgatcaggtc ctgcatgacg tggcgattca aaagcttccg   1260
gtcctgttcg ccatcgaccg cgcgggcatt gttggtgctg acggtcaaac ccatcagggt   1320
gcttttgatc tctcttacct gcgctgcata ccggaaatgg tcattatgac cccgagcgat   1380
gaaaacgaat gtcgccagat gctctatacc ggctatcact ataacgatgg cccgtcagcg   1440
gtgcgctacc cgcgtggcaa cgcggtcggc gtggaactga cgccgctgga aaaactacca   1500
attggcaaag gcattgtgaa gcgtcgtggc gagaaactgg cgatccttaa ctttggtacg   1560
ctgatgccag aagcggcgaa agtcgccgaa tcgctgaacg ccacgctggt cgatatgcgt   1620
tttgtgaaac gcttgatga agcgttaatt ctggaaatgg ccgccagcca tgaagcgctg   1680
gtcaccgtag aagaaacgc cattatgggc ggcgcaggca gcggcgtgaa cgaagtgctg   1740
atggcccatc gtaaaccagt acccgtgctg aacattggcc tgccggactt ctttattccg   1800
caaggaactc aggaagaaat gcgcgccgaa ctcggcctcg atgccgctgg tatggaagcc   1860
aaaatcaagg cctggctggc a                                             1881
```

<210> SEQ ID NO 39
<211> LENGTH: 1911
<212> TYPE: DNA
<213> ORGANISM: Corynebacterium glutamicum

<400> SEQUENCE: 39

```
ttattccccg aacagggaat ccagccatcc aacaacagtg gtttcaatgc cgtcggcgtc      60
gaggccataa tcggcgagca cttcattgcg ggacgcgtga tccaggtact tctgggggcac    120
```

| | |
|---|---|
| ggcgatttgt cggcgagggg tatccacctc agaggcgtta agcgcatcag agagcaagga | 180 |
| tcccacgccg ccgtggatga cgccgtcttc gatggtgatc acgaggtcat gatcatcaga | 240 |
| cagcgcgacc aaggactgcg ggatggggac aatccagcgg gggtcaacaa ccgtgacgtt | 300 |
| cacgccgtgc tgtttaatcc tggaagcaac gtcaagtgca acagttgcgc gctcgcctac | 360 |
| cgcaatgatg agaactgatg gcgcatcgtc ggttgattca acgtcagtgg cgtcttcata | 420 |
| tgcgaggaca tccacgccgt cttccaaggt gtcgatagca acaattggag ttggcaagtc | 480 |
| gcccttgggg aaacgcacaa ctgtggggcc atcatcgatg gaaatagcct cattgagcag | 540 |
| ctcacgcaag gaatcctcat cacgtggtgc cgccacctgc acgcctggaa cgatcgaggt | 600 |
| cagcgccata tcccagacgc cattgtggct cgctccatcc gaacccgtga cacctgagcg | 660 |
| atcaagcacc aaagtaacag gctggttgag catgcccaca tccatgagca gctgatcaaa | 720 |
| agcgcggttc aagaacgtgg agtaaatagc caccacaggg tgttttccac ccaatgcgag | 780 |
| gcctgcggca aagttaccg cgtgctgctc agcaatgccg acatcaaaga atcggttggg | 840 |
| gaaattggct tcgaacttgg acagaccggt aggacctgcc atcgcggcgg tgatggcaac | 900 |
| aacgttttca ttctgcgcac caatcttgac cagctcatcg ctgaacacag aggtccaacc | 960 |
| gggctttgat gcagatttag gagctcctgt gagcggatcg atgacgcccg tggagtgcat | 1020 |
| caattcgtcc aaatcctgct cagcaggcgc gtaaccacga cccttttcgg tgaccatgtg | 1080 |
| cacgatgatg gggccatcat aatcatgagc gtatttcagc gcattgtcga cagctttttg | 1140 |
| gttatgtcca tcaaccggac ccacgtattt catgcccagt tcagggaaca tttcggtggg | 1200 |
| aatgacggtg ctcttcacac cttctttaaa tgcatggagc gcttcaaaag tacgctcccc | 1260 |
| tacccacccc atggatttca gggacgtctt gcccttttcc atgaagcgat catagaaagg | 1320 |
| ctgcatgcga aggcccgcaa ggttttccgc aaatccgcca atggttggag aataactccg | 1380 |
| gccattgtca ttgactacga caacaacttt gcggtcttta ccagcagcaa tattgttcag | 1440 |
| tgcttcccaa cacatgccgc cagttagagc gccatcacca acgacagcaa ccacactatg | 1500 |
| cgtggtatcg ccatccaact gcttggcttt agacaaacca tccgcataag acaaggccgc | 1560 |
| cgaagcatgc gaagactcag tccaatcgtg ctcactttca gcacggcagg tgtaaccaga | 1620 |
| aaggccatct ttttgacgca aagaatcaaa atctttagcg cgacccgtca ggatcttatg | 1680 |
| cacataggac tggtgagaag tatcaaagat gatcgggtct tgaggcgaat cgaaaactcg | 1740 |
| atgaagaccg atggttaatt ccactacgcc caaatttgga cctaagtggc caccagttgc | 1800 |
| tgcgacttta tcgaccagga aagttcggat ttctttggca agagcgtcca atcctcatc | 1860 |
| attaagggcc tttaagtcag caggtgttga aatactgttc agaattccca t | 1911 |

<210> SEQ ID NO 40
<211> LENGTH: 2412
<212> TYPE: DNA
<213> ORGANISM: Enterococcus faecalis

<400> SEQUENCE: 40

| | |
|---|---|
| ttgaaaacag tagttattat tgatgcatta cgaacaccaa ttggaaaata taaaggcagc | 60 |
| ttaagtcaag taagtgccgt agacttagga acacatgtta caacacaact tttaaaaaga | 120 |
| cattccacta tttctgaaga aattgatcaa gtaatctttg gaaatgtttt acaagctgga | 180 |
| aatggccaaa atcccgcacg acaaatagca ataaacagcg gtttatctca tgaaattccc | 240 |
| gcaatgacag ttaatgaggt ctgcggatca ggaatgaagg ccgttatttt ggcgaaacaa | 300 |
| ttgattcaat taggagaagc ggaagtttta attgctggcg ggattgagaa tatgtcccaa | 360 | gcacctaaat tacaacgatt taattacgaa acagaaagct atgatgcgcc ttttctagt      420 atgatgtacg atgggttaac ggatgccttt agtggtcaag caatgggctt aactgctgaa      480 aatgtggccg aaaagtatca tgtaactaga gaagagcaag atcaattttc tgtacattca      540 caattaaaag cagctcaagc acaagcagaa gggatattcg ctgacgaaat agccccatta      600 gaagtatcag gaacgcttgt ggagaaagat gaagggattc gccctaattc gagcgttgag      660 aagctaggaa cgcttaaaac agttttaaa gaagacggta ctgtaacagc agggaatgca      720 tcaaccatta atgatggggc ttctgctttg attattgctt cacaagaata tgccgaagca      780 cacggtcttc cttatttagc tattattcga gacagtgtgg aagtcggtat tgatccagcc      840 tatatgggaa tttcgccgat taaagccatt caaaaactgt tagcgcgcaa tcaacttact      900 acggaagaaa ttgatctgta tgaaatcaac gaagcatttg cagcaacttc aatcgtggtc      960 caaagagaac tggctttacc agaggaaaag gtcaacattt atggtggcgg tatttcatta     1020 ggtcatgcga ttggtgccac aggtgctcgt ttattaacga gtttaagtta tcaattaaat     1080 caaaagaaa agaaatatgg agtggcttct ttatgtatcg gcggtggctt aggactcgct     1140 atgctactag agagacctca gcaaaaaaaa aacagccgat tttatcaaat gagtcctgag     1200 gaacgcctgg cttctcttct taatgaaggc cagatttctg ctgatacaaa aaaagaattt     1260 gaaaatacgg ctttatcttc gcagattgcc aatcatatga ttgaaaatca atcagtgaa     1320 acagaagtgc cgatgggcgt tggcttacat ttaacagtgg acgaaactga ttatttggta     1380 ccaatggcga cagaagagcc ctcagtgatt gcggcttttga gtaatggtgc aaaaatagca     1440 caaggattta aaacagtgaa tcaacaacgt ttaatgcgtg gacaaatcgt tttttacgat     1500 gttgcagacg ccgagtcatt gattgatgaa ctacaagtaa gagaaacgga attttttcaa     1560 caagcagagt taagttatcc atctatcgtt aaacgcggcg gcggcttaag agatttgcaa     1620 tatcgtgctt ttgatgaatc atttgtatct gtcgacttt tagtagatgt taaggatgca     1680 atgggggcaa atatcgttaa cgctatgttg gaaggtgtgg ccgagttgtt ccgtgaatgg     1740 tttgcggagc aaaagatttt attcagtatt ttaagtaatt atgccacgga gtcggttgtt     1800 acgatgaaaa cggctattcc agtttcacgt ttaagtaagg ggagcaatgg ccgggaaatt     1860 gctgaaaaaa ttgtttttagc ttcacgctat gcttcattag atccttatcg ggcagtcacg     1920 cataacaaag ggatcatgaa tggcattgaa gctgtcgttt tagctacagg aaatgataca     1980 cgcgctgtta gcgcttcttg tcatgctttt gcggtgaagg aaggtcgcta ccaaggtttg     2040 actagttgga cgctggatgg cgaacaacta attggtgaaa tttcagttcc gcttgcgtta     2100 gccacggttg gcggtgccac aaaagtctta cctaaatctc aagcagctgc tgatttgtta     2160 gcagtgacga tgcaaaaaga actaagtcga gtagtagcgg ctgttggttt ggcacaaaat     2220 ttagcggcgt tacgggcctt agtctctgaa ggaattcaaa aaggacacat ggctctacaa     2280 gcacgttctt tagcgatgac ggtcggagct actggtaaag aagttgaggc agtcgctcaa     2340 caattaaaac gtcaaaaaac gatgaaccaa gaccgagcct tggctatttt aaatgattta     2400 agaaaacaat aa                                                         2412

<210> SEQ ID NO 41
<211> LENGTH: 1149
<212> TYPE: DNA
<213> ORGANISM: Enterococcus faecalis

<400> SEQUENCE: 41

```
atgacaattg ggattgataa aattagtttt tttgtgcccc cttattatat tgatatgacg    60
gcactggctg aagccagaaa tgtagaccct ggaaaatttc atattggtat tgggcaagac   120
caaatggcgg tgaacccaat cagccaagat attgtgacat ttgcagccaa tgccgcagaa   180
gcgatcttga ccaaagaaga taagaggcc attgatatgg tgattgtcgg gactgagtcc    240
agtatcgatg agtcaaaagc ggccgcagtt gtcttacatc gtttaatggg gattcaacct   300
ttcgctcgct ctttcgaaat caaggaagct tgttacggag caacagcagg cttacagtta   360
gctaagaatc acgtagcctt acatccagat aaaaaagtct tggttgtagc agcagatatt   420
gcaaaatatg gattaaattc tggcggtgag cctacacaag gagctgggc ggttgcaatg    480
ttagttgcta gtgaaccgcg catcttggct ttaaaagagg ataatgtgat gctgacgcaa   540
gatatctatg acttttggcg tccaacaggc catccgtatc ctatggtcga tggtcctttg   600
tcaaacgaaa cctacatcca atcttttgcc caagtctggg atgaacataa aaaagaacc    660
ggtcttgatt ttgcagatta tgatgcttta gcgttccata ttccttacac aaaaatgggc   720
aaaaaagcct tattagcaaa aatctccgac caaactgaag cagaacagga acgaatttta   780
gcccgttatg aagaaagcat catctatagt cgtcgcgtag gaaacttgta tacgggttca   840
ctttatctgg gactcatttc cctttttagaa aatgcaacga ctttaaccgc aggcaatcaa   900
attgggttat tcagttatgg ttctggtgct gtcgctgaat ttttcactgg tgaattagta   960
gctggttatc aaaatcattt acaaaaagaa actcatttag cactgctaga taatcggaca  1020
gaactttcta cgctgaata tgaagccatg tttgcagaaa ctttagacac agatatt gat   1080
caaacgttag aagatgaatt aaaatatagt atttctgcta ttaataatac cgttcgctct  1140
tatcgaaac                                                          1149

<210> SEQ ID NO 42
<211> LENGTH: 879
<212> TYPE: DNA
<213> ORGANISM: Streptococcus pneumoniae

<400> SEQUENCE: 42
atgacaaaaa aagttggtgt cggtcaggca catagtaaga taattttaat aggggaacat    60
gcggtcgttt acggttatcc tgccatttcc ctgcctcttt tggaggtgga ggtgacctgt   120
aaggtagttc ctgcagagag tccttggcgc ctttatgagg aggataccttt gtccatggcg   180
gtttatgcct cactggagta tttgaatatc acagaagcct gcattcgttg tgagattgac   240
tcggctatcc ctgagaaacg ggggatgggt cgtcagcgg ctatcagcat gcggccatt    300
cgtgcagtat ttgactacta tcaggctgat ctgcctcatg atgtactaga aatcttggtc   360
aatcgagctg aaatgattgc ccatatgaat cctagtggtt tggatgctaa gacctgtctt   420
agtgaccaac ctattcgctt tatcaagaac gtaggattta cagaacttga gatggatta    480
tccgcctatt tggtgattgc cgatacgggt gtttatggtc atactcgtga agccatccaa   540
gtggttcaaa ataagggcaa ggatgcccta ccgttttgc atgccttggg agaattaacc    600
cagcaagcag aagttgcgat ttcacaaaaa gatgctgaag gactgggaca atcctcagt    660
caagcgcatt tacattttaaa agaaattgga gtcagtagcc ctgaggcaga cttttttggtt   720
gaaacgactc ttagccatgg tgctctgggt gccaagatga gcggtggtgg gctaggaggt   780
tgtatcatag ccttggtaac caatttgaca cacgcacaag aactagcaga aagattagaa   840
gagaaaggag ctgttcagac atggatagag agcctgtaa                           879
```

<210> SEQ ID NO 43
<211> LENGTH: 1011
<212> TYPE: DNA
<213> ORGANISM: Streptococcus pneumoniae

<400> SEQUENCE: 43

```
atgattgctg ttaaaacttg cggaaaactc tattgggcag gtgaatatgc tattttagag      60
ccagggcagt tagctttgat aaaggatatt cccatctata tgagggctga gattgctttt     120
tctgacagct accgtatcta ttcagatatg tttgatttcg cagtggactt aaggcccaat     180
cctgactaca gcttgattca agaaacgatt gctttgatgg agacttcct cgctgttcgc      240
ggtcagaatt taagaccttt ttccctaaaa atctgtggca aaatggaacg agaagggaaa     300
aagtttggtc taggttctag tggcagcgtc gttgtcttgg ttgtcaaggc tttactggct     360
ctctataatc tttcggttga tcagaatctc ttgttcaagc tgactagcgc tgtcttgctc     420
aagcgaggag acaatggttc catgggcgac cttgcctgta ttgtggcaga ggatttggtt     480
ctttaccagt catttgatcg ccagaaggcg gctgctggt tagaagaaga aaacttggcg      540
acagttctgg agcgtgattg gggattttttt atctcacaag tgaaaccaac tttagaatgt    600
gatttcttag tgggatggac caaggaagtg gctgtatcga gtcacatggt ccagcaaatc     660
aagcaaaata tcaatcaaaa ttttttaagt tcctcaaaag aaacggtggt ttctttggtc     720
gaagccttgg agcaggggaa agccgaaaaa gttatcgagc aagtagaagt agccagcaag     780
cttttagaag gcttgagtac agatatttac acgcctttgc ttagacagtt gaaagaagcc     840
agtcaagatt tgcaggccgt tgccaagagt agtggtgctg gtggtggtga ctgtggcatc     900
gccctgagtt ttgatgcgca atcttctcga aacactttaa aaaatcgttg ggccgatctg     960
gggattgagc tcttatatca agaaaggata ggacatgacg acaaatcgta a             1011
```

<210> SEQ ID NO 44
<211> LENGTH: 954
<212> TYPE: DNA
<213> ORGANISM: Streptococcus pneumoniae

<400> SEQUENCE: 44

```
atggatagag agcctgtaac agtacgttcc tacgcaaata ttgctattat caaatattgg      60
ggaaagaaaa aagaaaaaga gatggtgcct gctactagca gtatttctct aactttggaa     120
aatatgtata cagagacgac cttgtcgcct ttaccagcca atgtaacagc tgacgaatt     180
tacatcaatg gtcagctaca aaatgaggtc gagcatgcca agatgagtaa gattattgac     240
cgttatcgtc cagctggtga gggctttgtc cgtatcgata ctcaaaacaa tatgcctacg     300
gcagcgggcc tgtcctcaag ttctagtggt ttgtccgccc tggtcaaggc ttgtaatgct     360
tatttcaagc ttggattgga tagaagtcag ttggcacagg aagccaaatt tgcctcaggc     420
tcttcttctc ggagtttta tggaccacta ggagcctggg ataaggatag tggagaaatt     480
taccctgtag agacagactt gaaactagct atgattatgt tggtgctaga ggacaagaaa     540
aaaccaatct ctagccgtga cgggatgaaa cttttgtgtg aaacctcgac gacttttgac     600
gactgggttc gtcagtctga gaaggactat caggatatgc tgatttatct caaggaaaat     660
gattttgcca agattggaga attaacggag aaaaatgctc tggctatgca tgctacgaca     720
aagactgcta gtccagcctt ttcttatctg acggatgcct cttatgaggc tatggccttt     780
gttcgccagc ttcgtgagaa aggagaggcc tgctacttta ccatggatgc tggtcccaat     840
gttaaggtct tctgtcagga gaaagacttg gagcatttgt cagaaatttt cggtcagcgt     900
```

```
tatcgcttga ttgtgtcaaa acaaaggat ttgagtcaag atgattgctg ttaa        954
```

<210> SEQ ID NO 45
<211> LENGTH: 549
<212> TYPE: DNA
<213> ORGANISM: escherichia coli

<400> SEQUENCE: 45

```
atgcaaacgg aacacgtcat tttattgaat gcacagggag ttcccacggg tacgctggaa   60
aagtatgccg cacacacggc agacacccgc ttacatctcg cgttctccag ttggctgttt  120
aatgccaaag acaattatt agttacccgc cgcgcactga gcaaaaaagc atggcctggc  180
gtgtggacta actcggtttg tgggcaccca caactgggag aaagcaacga agacgcagtg  240
atccgccgtt gccgttatga gcttggcgtg gaaattacgc ctcctgaatc tatctatcct  300
gactttcgct accgcgccac cgatccgagt ggcattgtgg aaaatgaagt gtgtccggta  360
tttgccgcac gcaccactag tgcgttacag atcaatgatg atgaagtgat ggattatcaa  420
tggtgtgatt tagcagatgt attacacggt attgatgcca cgccgtgggc gttcagtccg  480
tggatggtga tgcaggcgac aaatcgcgaa gccagaaaac gattatctgc atttacccag  540
cttaaataa                                                          549
```

<210> SEQ ID NO 46
<211> LENGTH: 450
<212> TYPE: DNA
<213> ORGANISM: Corynebacterium glutamicum

<400> SEQUENCE: 46

```
ttgatcccta tcatcgatat ttcacaaaat gagcaagata gcgatatttt tatggccttt   60
atttatctag gtactctcct agttctcatt gggtgcatgg ctttgtgcga ccaccgttgg  120
aagctagcgt tcttccgcca tccgttacga gcaattcttt cggtaggtgc tgcatatatt  180
ggatttcttt tatgggatat atttggcatt attactggca ctttttatcg cggagactca  240
gcgtttatgt ccggtattaa ccttgcaccc catatgccca ttgaagaact ttttttctta  300
ttcttcctct gctacatcac cctcaacctt acctcggcag cagcattatg gcttaaagca  360
ccactgccta aaaaacccgg taaaaagtct cccctcacac cacagcgcga tactttccaa  420
ccaactacca ctcccgaggt tgaaccatga                                   450
```

<210> SEQ ID NO 47
<211> LENGTH: 393
<212> TYPE: DNA
<213> ORGANISM: Corynebacterium glutamicum

<400> SEQUENCE: 47

```
atgacttata tttttataag cattcctttt ttagcaatag ccatggtcct atttgtctta   60
aagctgcagt ctggaacacc taaacttta ccaatcaccg ctgtcagtgc ccttacccta  120
tgttccctaa ctatcatatt tgataacctc atggtttggg ctgatctctt tggatatggc  180
gataccagc accttggcat ttggctcggt ttaatccccc tagaggatct tttctatccg  240
ctcttcgcag tacttctgat tcctgcccta tggttgcctg aaatatgtt taaacgcagg  300
aaaaaacgtc cacaccattc cttacccacc atcgccaatg aagcatcac tactagatcc  360
accaccacgc aatctgagcc agaaaagccg tag                               393
```

<210> SEQ ID NO 48
<211> LENGTH: 864

<212> TYPE: DNA
<213> ORGANISM: Corynebacterium glutamicum

<400> SEQUENCE: 48

```
atgatggaaa aaataagact aattctattg tcatctcgcc ccattagctg gatcaatacc      60
gcctacccct ttggtctggc ctacctatta aatgcaggag agattgactg gctgttttgg     120
ctaggcatcg tattttttct tatcccgtat aacatcgcca tgtatggtat caacgatgtt     180
tttgattacg aatctgatat gcgtaatccc cgcaaaggcg cgtcgaggg ggccgtgcta      240
ccgaaaagtt cccacagcac actgttatgg gcctcggcta tctcaacaat tcctttccta     300
gttattcttt tcatatttgg cacctggatg tcgtctttat ggctgacact ctcagtgcta     360
gcagtgattg cttattcagc accgaaattg cgttttaaag aacgcccctt tatcgatgct     420
ctaacatctt ctactcactt cacttcacct gcattaatcg gtgcaacgat cactggaaca     480
tctccttcag cagcgatgtg gatagcactg ggatcctttt tcttgtgggg catggccagt     540
cagatccttg gagcagtaca ggatgttaat gcagaccggg aagctaatct gagctcaatt     600
gccactgtaa ttggggcgcg tggagccatt cggctttcag tagtacttta tttactagct     660
gctgtgttag tcactacttt gcctaatccg gcgtggatca tcgggattgc gattctaact     720
tacgtattta atgccgcacg attttggaac attacagatg ccagttgtga acaggctaat     780
cgcagttgga aagttttcct gtggctgaac tactttgttg gtgctgtgat aacgatactg     840
ctaatagcaa ttcatcagat ataa                                            864
```

<210> SEQ ID NO 49
<211> LENGTH: 37
<212> TYPE: DNA
<213> ORGANISM: Artificial Sequence
<220> FEATURE:
<223> OTHER INFORMATION: primer

<400> SEQUENCE: 49

```
gcgcgaattc atggaccaat tggtgaaaac tgaagtc                               37
```

<210> SEQ ID NO 50
<211> LENGTH: 37
<212> TYPE: DNA
<213> ORGANISM: Artificial Sequence
<220> FEATURE:
<223> OTHER INFORMATION: primer

<400> SEQUENCE: 50

```
gcgcgtcgac ttttaggatt taatgcaggt gacggac                               37
```

<210> SEQ ID NO 51
<211> LENGTH: 36
<212> TYPE: DNA
<213> ORGANISM: Artificial Sequence
<220> FEATURE:
<223> OTHER INFORMATION: primer

<400> SEQUENCE: 51

```
gcgcgaattc aaaaatggtg agtggcagta aagcgg                                36
```

<210> SEQ ID NO 52
<211> LENGTH: 33
<212> TYPE: DNA
<213> ORGANISM: Artificial Sequence
<220> FEATURE:
<223> OTHER INFORMATION: primer

```
<400> SEQUENCE: 52
gcgcgtcgac ttaggcgatt ttcatgaccg gtg                               33

<210> SEQ ID NO 53
<211> LENGTH: 32
<212> TYPE: DNA
<213> ORGANISM: Artificial Sequence
<220> FEATURE:
<223> OTHER INFORMATION: primer

<400> SEQUENCE: 53
gcgcgaattc aaaaatgagc caaccgccgc tg                                32

<210> SEQ ID NO 54
<211> LENGTH: 31
<212> TYPE: DNA
<213> ORGANISM: Artificial Sequence
<220> FEATURE:
<223> OTHER INFORMATION: primer

<400> SEQUENCE: 54
gcgcgtcgac ttaaacggga cgctgccaaa g                                 31

<210> SEQ ID NO 55
<211> LENGTH: 37
<212> TYPE: DNA
<213> ORGANISM: Artificial Sequence
<220> FEATURE:
<223> OTHER INFORMATION: primer

<400> SEQUENCE: 55
gcgcgaattc aaaaatgaaa aaaccgttg tgattgg                            37

<210> SEQ ID NO 56
<211> LENGTH: 35
<212> TYPE: DNA
<213> ORGANISM: Artificial Sequence
<220> FEATURE:
<223> OTHER INFORMATION: primer

<400> SEQUENCE: 56
gcgcgtcgac ttattgcaga tcctcaatca tcagg                             35

<210> SEQ ID NO 57
<211> LENGTH: 39
<212> TYPE: DNA
<213> ORGANISM: Artificial Sequence
<220> FEATURE:
<223> OTHER INFORMATION: primer

<400> SEQUENCE: 57
gcgcgaattc aaaaatgcaa ccgcattatg atctgattc                         39

<210> SEQ ID NO 58
<211> LENGTH: 37
<212> TYPE: DNA
<213> ORGANISM: Artificial Sequence
<220> FEATURE:
<223> OTHER INFORMATION: primer

<400> SEQUENCE: 58
gcgcgtcgac ttaacgatga gtcgtcataa tggcttg                           37

<210> SEQ ID NO 59
<211> LENGTH: 38
```

```
<212> TYPE: DNA
<213> ORGANISM: Artificial Sequence
<220> FEATURE:
<223> OTHER INFORMATION: primer

<400> SEQUENCE: 59
gcgcgaattc aaaaatgggt ctgatgctga ttgattgg                                38

<210> SEQ ID NO 60
<211> LENGTH: 38
<212> TYPE: DNA
<213> ORGANISM: Artificial Sequence
<220> FEATURE:
<223> OTHER INFORMATION: primer

<400> SEQUENCE: 60
gcgcgtcgac ttagtttttg attttgatac gggaagag                                38

<210> SEQ ID NO 61
<211> LENGTH: 36
<212> TYPE: DNA
<213> ORGANISM: Artificial Sequence
<220> FEATURE:
<223> OTHER INFORMATION: primer

<400> SEQUENCE: 61
gcgcgcggcc gcatcgcttc gctgattaat tacccc                                  36

<210> SEQ ID NO 62
<211> LENGTH: 33
<212> TYPE: DNA
<213> ORGANISM: Artificial Sequence
<220> FEATURE:
<223> OTHER INFORMATION: primer

<400> SEQUENCE: 62
gcgcactagt acaatgagcc ttgctgcaac atc                                     33

<210> SEQ ID NO 63
<211> LENGTH: 34
<212> TYPE: DNA
<213> ORGANISM: Artificial Sequence
<220> FEATURE:
<223> OTHER INFORMATION: primer

<400> SEQUENCE: 63
gcgcggtacc atcgcttcgc tgattaatta cccc                                    34

<210> SEQ ID NO 64
<211> LENGTH: 35
<212> TYPE: DNA
<213> ORGANISM: Artificial Sequence
<220> FEATURE:
<223> OTHER INFORMATION: primer

<400> SEQUENCE: 64
gcgcgcggcc gcacaatgag ccttgctgca acatc                                   35

<210> SEQ ID NO 65
<211> LENGTH: 40
<212> TYPE: DNA
<213> ORGANISM: Artificial Sequence
<220> FEATURE:
<223> OTHER INFORMATION: primer

<400> SEQUENCE: 65
```
gcgcgatatc actagtatcg cttcgctgat taattacccc                    40

<210> SEQ ID NO 66
<211> LENGTH: 33
<212> TYPE: DNA
<213> ORGANISM: Artificial Sequence
<220> FEATURE:
<223> OTHER INFORMATION: primer

<400> SEQUENCE: 66
gcgcgctagc acaatgagcc ttgctgcaac atc                           33

<210> SEQ ID NO 67
<211> LENGTH: 34
<212> TYPE: DNA
<213> ORGANISM: Artificial Sequence
<220> FEATURE:
<223> OTHER INFORMATION: primer

<400> SEQUENCE: 67
gcgcgctagc atcgcttcgc tgattaatta cccc                          34

<210> SEQ ID NO 68
<211> LENGTH: 33
<212> TYPE: DNA
<213> ORGANISM: Artificial Sequence
<220> FEATURE:
<223> OTHER INFORMATION: primer

<400> SEQUENCE: 68
gcgcagatct acaatgagcc ttgctgcaac atc                           33

<210> SEQ ID NO 69
<211> LENGTH: 31
<212> TYPE: DNA
<213> ORGANISM: Artificial Sequence
<220> FEATURE:
<223> OTHER INFORMATION: primer

<400> SEQUENCE: 69
gcgcggatcc atcgcttcgc tgattaatta c                             31

<210> SEQ ID NO 70
<211> LENGTH: 35
<212> TYPE: DNA
<213> ORGANISM: Artificial Sequence
<220> FEATURE:
<223> OTHER INFORMATION: primer

<400> SEQUENCE: 70
gcgcttaatt aaacaatgag ccttgctgca acatc                         35

<210> SEQ ID NO 71
<211> LENGTH: 36
<212> TYPE: DNA
<213> ORGANISM: Artificial Sequence
<220> FEATURE:
<223> OTHER INFORMATION: primer

<400> SEQUENCE: 71
gcgcttaatt aaatcgcttc gctgattaat taccccc                       36

<210> SEQ ID NO 72
<211> LENGTH: 38
<212> TYPE: DNA
<213> ORGANISM: Artificial Sequence
<220> FEATURE:
<223> OTHER INFORMATION: primer

<400> SEQUENCE: 72
gcgctctaga ggggaaactt aagaaattc tattcttg                        38

<210> SEQ ID NO 73
<211> LENGTH: 33
<212> TYPE: DNA
<213> ORGANISM: Artificial Sequence
<220> FEATURE:
<223> OTHER INFORMATION: primer

<400> SEQUENCE: 73
ataaagcttc ttcctgtctt cccgacccac tac                            33

<210> SEQ ID NO 74
<211> LENGTH: 53
<212> TYPE: DNA
<213> ORGANISM: Artificial Sequence
<220> FEATURE:
<223> OTHER INFORMATION: primer

<400> SEQUENCE: 74
cccatccact aaacttaaac aaatttaatg atcgtatgag gtcttttgag atg      53

<210> SEQ ID NO 75
<211> LENGTH: 55
<212> TYPE: DNA
<213> ORGANISM: Artificial Sequence
<220> FEATURE:
<223> OTHER INFORMATION: primer

<400> SEQUENCE: 75
tgtttaagtt tagtggatgg gtcatgatgg aaaaaataag actaattcta ttgtc    55

<210> SEQ ID NO 76
<211> LENGTH: 37
<212> TYPE: DNA
<213> ORGANISM: Artificial Sequence
<220> FEATURE:
<223> OTHER INFORMATION: primer

<400> SEQUENCE: 76
aaacctgcag gtgattctgt tttggttact catcccg                        37

<210> SEQ ID NO 77
<211> LENGTH: 19
<212> TYPE: DNA
<213> ORGANISM: Artificial Sequence
<220> FEATURE:
<223> OTHER INFORMATION: primer

<400> SEQUENCE: 77
actgcccgaa ccattgccg                                            19

<210> SEQ ID NO 78
<211> LENGTH: 22
<212> TYPE: DNA
<213> ORGANISM: Artificial Sequence
<220> FEATURE:
<223> OTHER INFORMATION: primer

<400> SEQUENCE: 78
aggccagacc aaagggtag gc                                         22

<210> SEQ ID NO 79
<211> LENGTH: 30
<212> TYPE: DNA
<213> ORGANISM: Artificial Sequence
<220> FEATURE:
<223> OTHER INFORMATION: primer

<400> SEQUENCE: 79
gctaagcttg gctgttttgg cggatgagag                                    30

<210> SEQ ID NO 80
<211> LENGTH: 35
<212> TYPE: DNA
<213> ORGANISM: Artificial Sequence
<220> FEATURE:
<223> OTHER INFORMATION: primer

<400> SEQUENCE: 80
cgaatcgata gagtttgtag aaacgcaaaa aggcc                              35

<210> SEQ ID NO 81
<211> LENGTH: 42
<212> TYPE: DNA
<213> ORGANISM: Artificial Sequence
<220> FEATURE:
<223> OTHER INFORMATION: primer

<400> SEQUENCE: 81
gctgccggca gatctcatat gccaatacgc aaaccgcctc tc                      42

<210> SEQ ID NO 82
<211> LENGTH: 45
<212> TYPE: DNA
<213> ORGANISM: Artificial Sequence
<220> FEATURE:
<223> OTHER INFORMATION: primer

<400> SEQUENCE: 82
gctgaattca ctagtgcggc cgcttattcg ccattcaggc tgcgc                   45

<210> SEQ ID NO 83
<211> LENGTH: 44
<212> TYPE: DNA
<213> ORGANISM: Artificial Sequence
<220> FEATURE:
<223> OTHER INFORMATION: primer

<400> SEQUENCE: 83
catactagta ggaggtaata aatatggttg cccaacaaac acga                    44

<210> SEQ ID NO 84
<211> LENGTH: 40
<212> TYPE: DNA
<213> ORGANISM: Artificial Sequence
<220> FEATURE:
<223> OTHER INFORMATION: primer

<400> SEQUENCE: 84
cggctcgagt taatattttc tggcaacaat atattcggcg                         40

<210> SEQ ID NO 85
<211> LENGTH: 43
<212> TYPE: DNA
<213> ORGANISM: Artificial Sequence
<220> FEATURE:
<223> OTHER INFORMATION: primer

<400> SEQUENCE: 85
gctctcgagg aggtaataaa tatgctcgat cctggcccca atc                43

<210> SEQ ID NO 86
<211> LENGTH: 36
<212> TYPE: DNA
<213> ORGANISM: Artificial Sequence
<220> FEATURE:
<223> OTHER INFORMATION: primer

<400> SEQUENCE: 86
gcagctagct tatgatgtca ccagactgtc ggcctc                        36

<210> SEQ ID NO 87
<211> LENGTH: 42
<212> TYPE: DNA
<213> ORGANISM: Artificial Sequence
<220> FEATURE:
<223> OTHER INFORMATION: primer

<400> SEQUENCE: 87
gcagctagca ggaggtaata aatatgagcc aaccgccgct gc                 42

<210> SEQ ID NO 88
<211> LENGTH: 29
<212> TYPE: DNA
<213> ORGANISM: Artificial Sequence
<220> FEATURE:
<223> OTHER INFORMATION: primer

<400> SEQUENCE: 88
ctcctctaga ttactaaacg ggacgctgc                                29

<210> SEQ ID NO 89
<211> LENGTH: 44
<212> TYPE: DNA
<213> ORGANISM: Artificial Sequence
<220> FEATURE:
<223> OTHER INFORMATION: primer

<400> SEQUENCE: 89
ccatctagag gaggtaataa aatatgaagg acaaggaact gagc               44

<210> SEQ ID NO 90
<211> LENGTH: 33
<212> TYPE: DNA
<213> ORGANISM: Artificial Sequence
<220> FEATURE:
<223> OTHER INFORMATION: primer

<400> SEQUENCE: 90
cgtgcggccg cttattcctc atccccgacg cgc                           33

<210> SEQ ID NO 91
<211> LENGTH: 49
<212> TYPE: DNA
<213> ORGANISM: Artificial Sequence
<220> FEATURE:
<223> OTHER INFORMATION: primer

<400> SEQUENCE: 91
cggtcgacag gaggtaataa atatgcaacc gcattatgat ctgattctc          49

<210> SEQ ID NO 92

```
<211> LENGTH: 43
<212> TYPE: DNA
<213> ORGANISM: Artificial Sequence
<220> FEATURE:
<223> OTHER INFORMATION: primer

<400> SEQUENCE: 92
cgcctgcagg aggcctttaa cgatgagtcg tcataatggc ttg          43

<210> SEQ ID NO 93
<211> LENGTH: 48
<212> TYPE: DNA
<213> ORGANISM: Artificial Sequence
<220> FEATURE:
<223> OTHER INFORMATION: primer

<400> SEQUENCE: 93
cgaggcctag gaggtaataa atatgggtct gatgctgatt gattggtg     48

<210> SEQ ID NO 94
<211> LENGTH: 40
<212> TYPE: DNA
<213> ORGANISM: Artificial Sequence
<220> FEATURE:
<223> OTHER INFORMATION: primer

<400> SEQUENCE: 94
cgcctgcagg ttagtttttg attttgatac gggaagagtg              40
```

MICROORGANISM COMPRISING GENE FOR CODING ENZYME INVOLVED IN PRODUCING RETINOID AND METHOD FOR PRODUCING RETINOID BY USING SAME

CROSS REFERENCE TO RELATED APPLICATION

This application claims benefit under 35 U.S.C. 119(e), 120, 121, or 365(c), and is a National Stage entry from International Application No. PCT/KR2013/009643, filed Oct. 28, 2013, which claims priority to and the benefit of Korean Patent Application No. 10-2013-0071130 filed in the Korean Intellectual Property Office on Jun. 20, 2013, the entire contents of which are incorporated herein by reference.

TECHNICAL FIELD

The present invention relates to a microorganism including genes coding enzymes involved in retinoid production, and a retinoid producing method using the same.

BACKGROUND ART

Retinoids are a class of lipophilic isoprenoid molecules chemically related vitamin A. The retinoids possess a β-ionone ring and a polyunsaturated side chain with an alcohol (for example, retinol), an aldehyde (for example, retinal), a carboxylic acid (for example, retinoic acid) group or an ester (for example, retinyl acetate) functional group. It is known that the retinoids have essential roles in human health such as eye protection, bone development and regeneration, and providing antioxidative effects, and skin anti-aging, and decrease a risk of certain cancers.

In recent years, the retinoids have received great attention as effective cosmetics and medicine sources for anti-wrinkle and skin disease treatment. The worldwide retinoid market size is estimated at about 16 billion dollars. Chemically synthesized retinoids are representative commercial sources. Retinol is produced through acidification or hydrolysis of chemically synthesized retinal due to reduction of pentadiene derivatives. However, such chemical processes have disadvantages such as a complex purification operation and undesired by-product formation. Animals produce retinoids from carotenoids obtained from fruits and vegetables, but plants are unable to synthesize retinoids. A complete pathway in retinoid synthesis is possible only in microorganisms having bacteriorhodopsin or proteorhodopsin that includes retinal as a prosthetic group. However, since microorganisms produce retinal-binding protein forms, it is inappropriate for mass production of free retinoids. Limited attempts for biological production using enzymes have been tried so far, but the results were unsuccessful. Therefore, it is necessary to develop a biotechnological method for producing retinoids using metabolically transformed microorganisms.

Retinoids are chemically very unstable and easily oxidized and isomerized by heat, oxygen and light due to their reactive conjugated double bonds. Also, retinoids are easily biodegraded by retinoic acid. Therefore, a method of producing retinoids more efficiently is necessary.

In Korean Laid-open Patent Application No. 2008-42387, a method of mass-producing an isoprenoid, *E. coli* transformed with carotenoid biosynthesis genes and astaxanthin using the same is disclosed.

[Patent Literature] Korean Laid-open Patent Application No. 2008-42387

SUMMARY

The present invention provides a microorganism capable of safely producing retinoid with high efficiency.

The present invention provides a retinoid producing method using the same microorganism.

1. A microorganism (the genus *Saccharomyces*) including genes coding enzymes involved in retinoid production.
2. In item 1, the genes may code at least one amino acid sequence selected from the group consisting of SEQ ID NOs 2 to 9.
3. In item 1, the genes may code an amino acid sequence of at least one of SEQ ID NOs 2, 3 and 10; at least one of SEQ ID NOs 4 and 11; at least one of SEQ ID NOs 5, 6 and 12; SEQ ID NO 7; SEQ ID NO 8; and at least one of SEQ ID NOs 9, 13 and 21.
4. In item 3, the microorganism may further include a gene coding an amino acid sequence of SEQ ID NO 1.
5. In item 1, the microorganism may be *Saccharomyces cerevisiae*.
6. In item 1, the microorganism may be *Saccharomyces cerevisiae* Y2805.
7. A microorganism (the genus *Corynebacterium*) including genes coding enzymes involved in retinoid production.
8. In item 7, the genes may code at least one amino acid sequence selected from the group consisting of SEQ ID NOs 2 to 9.
9. In item 7, the genes may code an amino acid sequence of at least one of SEQ ID NOs 2, 3 and 10; at least one of SEQ ID NOs 4 and 11; at least one of SEQ ID NOs 5, 6 and 12; SEQ ID NO 7; SEQ ID NO 8; and at least one of SEQ ID NOs 9, 13 and 21.
10. In item 9, the microorganism may further include a gene coding at least one amino acid sequence of SEQ ID NOs 14 and 15.
11. In item 9, the microorganism may further include a gene coding an amino acid sequence of SEQ ID NOs 16 to 20.
12. In item 7, in the microorganism, a gene coding at least one amino acid sequence selected from the group consisting of SEQ ID NOs 22 to 24 may be inactivated or deleted.
13. In item 7, the microorganism may be *Corynebacterium glutamicum*.
14. In item 7, the microorganism may be *Corynebacterium glutamicum* ATCC13032.
15. In any of items 1 to 14, the gene may be introduced by a vector.
16. A retinoid producing method including: culturing the microorganism according to any of items 1 to 14; and isolating a retinoid from a culture product of the microorganism.
17. In item 16, the microorganism may be cultured in a medium including a lipophilic substance.
18. In item 17, the isolating may be performed from a lipophilic substance phase.
19. In item 17, the lipophilic substance may be octane, decane, dodecane, tetradecane, phytosqualane, mineral oil, isopropyl myristate, cetyl ethylhexanoate, to dioctanoyl decanoyl glycerol, squalane, or combinations thereof.

The microorganism including genes coding enzymes involved in retinoid production of the present invention can safely produce retinoids on a large scale with high efficiency.

The retinoids obtained through the retinoid producing method using the microorganism of the present invention can be widely used as sources of cosmetics, food, medicines and the like. When there is a need to effectively produce specific retinoids for preparing cosmetics, food, medicines, and the like, the retinoid producing method of the present invention can be appropriately used.

DETAILED DESCRIPTION

Figure 1:
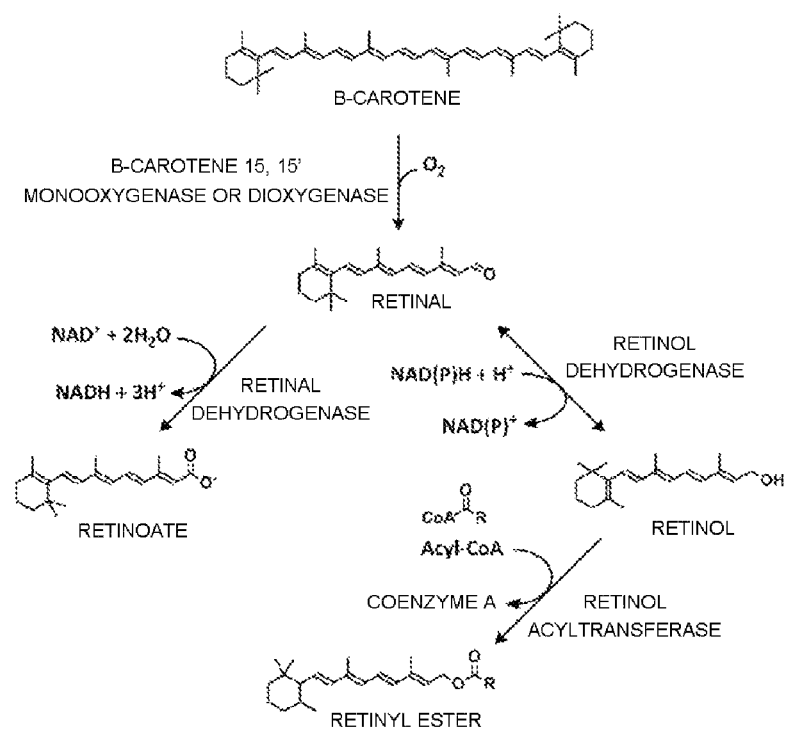
FIG. 1 is a diagram showing conversion of β-carotene into retinoids including retinal, retinol, retinoic acid, and a retinyl ester.

The present invention relates to a microorganism and a retinoid producing method using the same through which genes coding enzymes involved in retinoid production are included and thus retinoids can be safely produced on a large scale with high efficiency.

The present invention will be described below in further detail.

The present invention provides a microorganism having retinoid productivity.

The term "retinoids" refer to a class of chemical substances that are chemically related to vitamin A. Retinoids have a structure including a cyclic end group, a polyene side chain and a polar end group. A conjugated system formed by alternating C=C double bonds in the polyene side chain is responsible for the color of retinoids (typically yellow, orange or red). Many retinoids are chromophores. Alteration of side chains and end groups can create various retinoids. The retinoids may be retinal, retinol, retinoic acid, retinyl acetate, or combinations thereof. The retinoid may also be an in vivo degradation product of retinal, retinol, retinoic acid, retinyl acetate, or combinations thereof.

The microorganism may be the genus *Saccharomyces* or the genus *Corynebacterium*.

The microorganism (the genus *Saccharomyces*) is not specifically limited, but may be appropriately selected according to retinoid productivity, and may be, for example, *Saccharomyces cerevisiae*, and preferably, *Saccharomyces cerevisiae* Y2805.

The microorganism (the genus *Corynebacterium*) is not specifically limited, but may be appropriately selected according to retinoid productivity, and may be, for example, *Corynebacterium glutamicum*, and preferably *Corynebacterium glutamicum* ATCC13032 (*Corynebacterium glutamicum* ATCC13032, taxid: 196627; GenBank NID: NC_003450, ATCC13032).

*Corynebacterium glutamicum* ATCC13032 is deposited in the International Depository Authority, ATCC (American Type Culture Collection, Manassas, USA), and available therefrom.

The microorganism having retinoid productivity of the present invention includes genes coding enzymes involved in retinoid production.

The enzymes involved in retinoid production in the present invention generally refer to enzymes necessary for retinoid production, enzymes for increasing an amount of retinoid production, or combinations thereof.

The genes may code an amino acid sequence of geranylgeranyl pyrophosphate (GGPP) synthase derived from *Pantoea agglomerans* of SEQ ID NO 2, an amino acid sequence of geranylgeranyl pyrophosphate (GGPP) synthase derived from *Synechocystis* sp. PCC6803 of SEQ ID NO 3, an amino acid sequence of phytoene synthase derived from *Pantoea agglomerans* of SEQ ID NO 4, an amino acid sequence of phytoene dehydrogenase derived from *Pantoea agglomerans* of SEQ ID NO 5, an amino acid sequence of phytoene dehydrogenase derived from *Rhodopseudomonas palustris* of SEQ ID NO 6, an amino acid sequence of lycopene-beta-cyclase derived from *Pantoea ananatis* of SEQ ID NO 7, an amino acid sequence of beta carotene monooxygenase derived from uncultured marine bacterium 66A03 of SEQ ID NO 8, an amino acid sequence of IPP isomerase derived from *Cronobacter sakazakii* of SEQ ID NO 9, and the like. These may be used alone or in combinations of two or more thereof.

When the microorganism having retinoid productivity of the present invention is the genus *Saccharomyces*, the gene may preferably code an amino acid sequence of at least one of SEQ ID NOs 2, 3 and 10; at least one of SEQ ID NOs 4 and 11; at least one of SEQ ID NOs 5, 6 and 12; SEQ ID NO 7; SEQ ID NO 8; and at least one of SEQ ID NOs 9, 13 and 21. In this case, it is possible to maximize an amount of production by producing retinoids more efficiently.

SEQ ID NO 10 is an amino acid sequence of GGPP synthase derived from *Corynebacterium glutamicum*. SEQ ID NO 11 is an amino acid sequence of phytoene synthase derived from *Corynebacterium glutamicum*. SEQ ID NO 12 is an amino acid sequence of phytoene dehydrogenase derived from *Corynebacterium glutamicum*. SEQ ID NO 13 is an amino acid sequence of isopentenyl diphosphate (IPP) isomerase derived from *Corynebacterium glutamicum*. SEQ ID NO 21 is an amino acid sequence of isopentenyl diphosphate (IPP) isomerase derived from *E. coli*.

Also, the microorganism (the genus *Saccharomyces*) may further include a gene coding an amino acid sequence of hydroxymethylglutaryl (HMG)-CoA reductase derived from *Saccharomyces cerevisiae* of SEQ ID NO 1. This further increases an amount of retinoid production.

When the microorganism having retinoid productivity of the present invention is the genus *Corynebacterium*, the gene may preferably code an amino acid sequence of at least one of SEQ ID NOs 2, 3 and 10; at least one of SEQ ID NOs 4 and 11; at least one of SEQ ID NOs 5, 6 and 12; SEQ ID NO 7; SEQ ID NO 8; and at least one of SEQ ID NOs 9, 13 and 21. In this case, it is possible to maximize an amount of production by producing retinoids more efficiently.

Also, the microorganism (the genus *Corynebacterium*) may further include genes coding an amino acid sequence of 1-deoxy-D-xylulose 5-phosphate (DXP) synthase derived from *E. coli* of SEQ ID NO 14, an amino acid sequence of intrinsic 1-deoxy-D-xylulose 5-phosphate (DXP) synthase of SEQ ID NO 15 and the like. These may be used alone or in combinations of two or more thereof. This further increases an amount of retinoid production.

DXP is an enzyme related to a rate determining step in an intrinsic MEP pathway. The microorganism of the present invention further includes a gene coding an amino acid sequence of DXP synthase, and thus can produce beta carotene at a high concentration. FIG. 1 shows conversion of β-carotene into retinoids including retinal, retinol, retinoic acid, and a retinyl ester.

Figure 2:
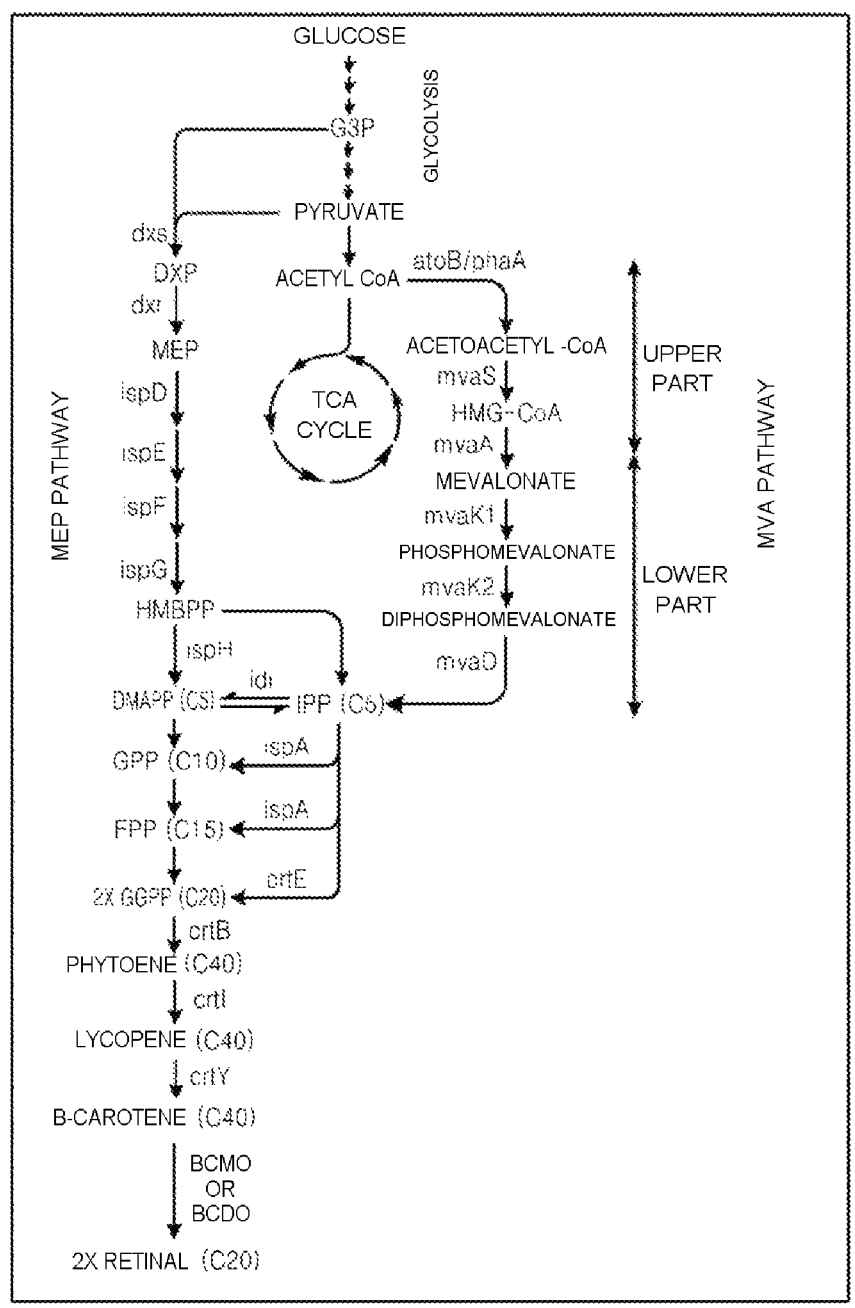
FIG. 2 is a diagram schematically showing an MEP pathway and a foreign MVA pathway in retinal biosynthesis.

Also, the microorganism (the genus *Corynebacterium*) has an intrinsic MEP pathway, and may further include genes coding enzymes of a foreign mevalonate pathway involved in producing IPP from acetyl-CoA. FIG. 2 is a diagram schematically showing an MEP pathway and a foreign MVA pathway in retinal biosynthesis.

The genes coding enzymes of the foreign mevalonate pathway may code, for example, an amino acid sequence of acetyl-CoA acetyltransferase/hydroxymethylglutaryl (HMG)-CoA reductase derived from *Enterococcus faecalis* of SEQ ID NO 16, an amino acid sequence of HMG-CoA synthase derived from *Enterococcus faecalis* of SEQ ID NO 17, an amino acid sequence of mevalonate kinase derived from *Streptococcus pneumoniae* of SEQ ID NO 18, an amino acid sequence of phosphomevalonate kinase derived from *Streptococcus pneumoniae* of SEQ ID NO 19, an amino acid sequence of mevalonate diphosphate decarboxylase derived from *Streptococcus pneumoniae* of SEQ ID NO 20, and the like. These may be used alone or in combinations of two or more thereof.

The IPP isomerase has a decisive role in regulating a combination ratio of isoprene units during a carotenoid or isoprenoid biosynthesis process, that is, a ratio of IPP and DMAPP with respect to each isoprene unit.

Also, in the microorganism of the present invention, genes coding enzymes involved in synthesizing beta carotene from the IPP may be further introduced, or two copies of the IPP isomerase may be introduced and thus conversion from IPP to DMAPP may be promoted. Therefore, the microorganism can produce beta carotene at a high concentration.

The genes may be introduced by any method known in the related art. The genes may be introduced by, for example, a vector.

The term "vector" refers to a nucleic acid molecule that can deliver other linked nucleic acids. In terms of nucleic acid sequences mediating introduction of specific genes, the vector in the present invention can be regarded as being used interchangeably with a nucleic acid structure and a cassette.

The vector includes a vector that is derived from, for example, a plasmid or virus. The plasmid refers to a circular double stranded DNA loop to which additional DNA can be linked. The vector used in the present invention includes, for example, a plasmid expression vector, a plasmid shuttle vector, a virus expression vector (for example, a replication-defective retroviral vector, a retroviral vector, an adenoviral vector, a herpes simplex viral vector, a poxviral vector, a lentiviral vector, and an adeno-associated viral vector) and a viral vector that can perform the same function thereof, but the present invention is not limited thereto.

A specific gene may be activated, or inactivated or deleted in the microorganism of the present invention in order to promote productivity of retinoids. For example, a gene coding at least one amino acid sequence selected from the group consisting of SEQ ID NOs 22 to 24 may be inactivated or deleted in the microorganism (the genus *Corynebacterium*).

In the microorganism (the genus *Corynebacterium*), flavuxanthin is synthesized from lycopene by prenyl transferase having an amino acid sequence of SEQ ID NO 22 coded by an intrinsic crtEb gene, and the synthesized flavuxanthin is converted into decaprenoxanthin by carotenoid-ε-cyclase having sequences of SEQ ID NOs 23 and 24 coded by intrinsic crtYe and crtYf genes, respectively.

In the present invention, by inactivating or deleting genes coding at least one amino acid sequence selected from the group consisting of SEQ ID NOs 22 to 24, production of decaprenoxanthin is suppressed, and lycopene is accumulated, which can be used as a precursor of retinoids serving as final products.

The term "deletion" or "inactivation" refers to the fact that expression of the gene decreases or no expression is performed. The "inactivation" may be performed by a method known in the related art. For example, the gene may be inactivated by homologous recombination. The homologous recombination may be mediated by, for example, transposon mutagenesis or P1 transduction.

A gene (HMG1) coding an amino acid sequence of SEQ ID NO 1 has a nucleotide sequence of SEQ ID NO 25. A gene (crtE) coding an amino acid sequence of SEQ ID NO 2 has a nucleotide sequence of SEQ ID NO 26. A gene (crtE) coding an amino acid sequence of SEQ ID NO 3 has a nucleotide sequence of SEQ ID NO 27. A gene (crtB) coding an amino acid sequence of SEQ ID NO 4 has a nucleotide sequence of SEQ ID NO 28. A gene (crtI) coding an amino acid sequence of SEQ ID NO 5 has a nucleotide sequence of SEQ ID NO 29. A gene (crtI) coding an amino acid sequence of SEQ ID NO 6 has a nucleotide sequence of SEQ ID NO 30. A gene (crtY) coding an amino acid sequence of SEQ ID NO 7 has a nucleotide sequence of SEQ ID NO 31. A gene (SR) coding an amino acid sequence of SEQ ID NO 8 has a nucleotide sequence of SEQ ID NO 32. A gene (idi) coding an amino acid sequence of SEQ ID NO 9 has a nucleotide sequence of SEQ ID NO 33. A gene (crtE) coding an amino acid sequence of SEQ ID NO 10 has a nucleotide sequence of SEQ ID NO 34.

A gene (crtB) coding an amino acid sequence of SEQ ID NO 11 has a nucleotide sequence of SEQ ID NO 35. A gene (crtI) coding an amino acid sequence of SEQ ID NO 12 has a nucleotide sequence of SEQ ID NO 36. A gene (idi) coding an amino acid sequence of SEQ ID NO 13 has a nucleotide sequence of SEQ ID NO 37. A gene (dxs) coding an amino acid sequence of SEQ ID NO 14 has a nucleotide sequence of SEQ ID NO 38. A gene (dxs) coding an amino acid sequence of SEQ ID NO 15 has a nucleotide sequence of SEQ ID NO 39. A gene (mvaE) coding an amino acid sequence of SEQ ID NO 16 has a nucleotide sequence of SEQ ID NO 40. A gene (mvaS) coding an amino acid sequence of SEQ ID NO 17 has a nucleotide sequence of SEQ ID NO 41. A gene (mvaK1) coding an amino acid sequence of SEQ ID NO 18 has a nucleotide sequence of SEQ ID NO 42. A gene (mvaK2) coding an amino acid sequence of SEQ ID NO 19 has a nucleotide sequence of SEQ ID NO 43. A gene (mvaD) coding an amino acid sequence of SEQ ID NO 20 has a nucleotide sequence of SEQ ID NO 44.

A gene (idi) coding an amino acid sequence of SEQ ID NO 21 has a nucleotide sequence of SEQ ID NO 45. A gene (crtYe) coding an amino acid sequence of SEQ ID NO 22 has a nucleotide sequence of SEQ ID NO 46. A gene (crtYf) coding an amino acid sequence of SEQ ID NO 23 has a nucleotide sequence of SEQ ID NO 47. A gene (CrtEb) coding an amino acid sequence of SEQ ID NO 24 has a nucleotide sequence of SEQ ID NO 48.

The present invention also provides a retinoid producing method using a microorganism having retinoid productivity.

According to an implementation example of the present invention, operations of the retinoid producing method of the present invention will be described in detail.

First, the microorganism having retinoid productivity is cultured.

The culture may be performed in a synthetic, semi-synthetic or complex culture medium.

The culture medium is not specifically limited. A medium including a carbon source, a nitrogen source, a vitamin and a mineral may be used. For example, a Man-Rogosa-Sharp (MRS) liquid medium, and a liquid medium including milk may be used.

The carbon source of the medium may be selected from the group consisting of, for example, a starch, glucose, sucrose, galactose, fructose, glycerol and mixtures thereof and used. Preferably, glucose or galactose may be used.

The nitrogen source of the medium may be selected from the group consisting of, for example, ammonium sulfate, ammonium nitrate, sodium nitrate, glutamic acid, casamino acid, *Saccharomyces* extracts, a peptone, a tryptone, soybean meal and mixtures thereof, and used. The mineral may be selected from the group consisting of, for example, sodium chloride, dipotassium phosphate, magnesium sulfate and mixtures thereof, and used.

Contents of the carbon source, the nitrogen source and the mineral in the medium are not specifically limited. For example, 10 to 100 g, 5 to 40 g and 0.5 to 4 g per liter may be used.

The vitamin may be selected from the group consisting of, for example, vitamin B, vitamin C, vitamin D, vitamin E and mixtures thereof. The vitamin may be added to the medium simultaneously with the carbon source, the nitrogen source, and the mineral, or may be added to a prepared medium that is sterilized.

The culture may be performed under general culture conditions of the genus *Saccharomyces* or the genus *Corynebacterium*, and may be performed for, for example, 24 to 96 hours at 15 to 45° C.

In order to remove the culture medium from a culture solution and isolate or remove only concentrated cells, a centrifugation or filtration process may be performed. Such a process may be performed by those killed in the art as necessary. The concentrated cells may be frozen or freeze-dried by a general method and preserved without losing activity.

When the microorganism having retinoid productivity is the genus *Saccharomyces*, the culture may be performed in a medium including glucose and galactose as the carbon source. Since galactose promotes promoter expression of introduced genes, when the culture is performed in the medium including galactose, production of retinoids is further promoted.

A galactose content of the medium including galactose is not specifically limited, may be appropriately selected to sufficiently promote promoter expression and obtain optimal growth, and may be included, for example, at 0.5 to 2 vol %, and preferably 0.5 to 1.5 vol %.

The medium may include, for example, a peptone (0.5 to 4 wt %), *Saccharomyces* extracts (0.5 to 2 wt %), glucose (0.5 to 2 vol %), and galactose (0.5 to 2 vol %).

When the microorganism having retinoid productivity is the genus *Corynebacterium*, the culture may be performed in a medium including glucose as the carbon source.

A glucose content of the medium including glucose is not specifically limited, and may be appropriately selected to obtain optimal growth, and may be included, for example, at 0.5 to 2 vol %, and preferably 0.5 to 1.5 vol %.

The medium may include, for example, 0.5 to 2 g of $K_2HPO_4$, 5 to 20 g of $(NH_4)_2SO_4$, 0.1 to 1 g of $MgSO_4 \cdot 7H_2O$, 5 to 40 mg of $FeSO_4 \cdot 7H_2O$, 5 to 40 mg of $MnSO_4 \cdot H_2O$, 20 to 80 mg of NaCl, 0.5 to 4 g of urea, 0.05 to 0.5 mg of biotin and 0.05 to 0.5 mg of thiamine, per liter The culture of the microorganism having retinoid productivity according to the present invention may be performed in a culture medium in the presence of a lipophilic substance. In this case, the microorganism is placed in a lipophilic substance phase of a medium surface and cultured.

An amount of retinoid production from the microorganism having retinoid productivity shows the highest value at a certain time and gradually decreases thereafter. This is because additional synthesis of retinoids is stopped during a stagnant state of microorganism growth, and oxidative degradation of retinoids occurs in the cells.

However, the lipophilic substance absorbs produced retinoids before the retinoids are degraded in the cells, and thus may improve retinoid production efficiency.

The lipophilic substance is not specifically limited as long as it has the above function and has no influence on the microorganism growth, and may be, for example, octane, decane, dodecane, tetradecane, phytosqualane, mineral oil, isopropyl myristate, cetyl ethyl hexanonate, dioctanoyl decanoyl glycerol, squalane, or combinations thereof, and preferably decane, dodecane, heavy mineral oil, or combinations thereof.

The lipophilic substance may have no influence on the microorganism growth, and have low volatility and hydrophobicity in order to extract hydrophobic retinoids.

When the microorganism of the present invention is the genus *Saccharomyces*, the culture is more preferably performed in a medium including dodecane or decane. When the microorganism of the present invention is the genus *Corynebacterium*, the culture is more preferably performed in a medium including heavy mineral oil.

A content of the lipophilic substance in the medium is not specifically limited as long as it is within a range at which all of the above functions can be performed. For example, a volume ratio of the lipophilic substance with respect to the medium may be 1:0.1-3.0, 1:0.2-3.0, 1:0.5-3.0, 1:1.0-3.0, 1:1.5-3.0, 1:2.0-3.0, 1:2.5-3.0, 1:0.2-2.5, 1:0.2-2.0, 1:0.2-1.5, 1:0.2-1.0, 1:0.2-0.5, 1:0.5-2.5, 1:0.5-2.0, 1:0.5-1.5, 1:0.5-1.0, 1:0.8-2.5, 1:0.8-2.0, 1:0.8-1.5, 1:0.8-1.2, and 1:0.8-1.0.

The culture may be performed with stirring.

Stirring may be performed at 100 to 300 rpm, for example, 100 to 280 rpm, 100 to 260 rpm, 100 to 240 rpm, 100 to 220 rpm, 100 to 200 rpm, 100 to 180 rpm, 100 to 160 rpm, 100 to 140 rpm, 100 to 120 rpm, 120 to 300 rpm, 120 to 280 rpm, 120 to 260 rpm, 120 to 240 rpm, 120 to 220 rpm, 120 to 200 rpm, 120 to 180 rpm, 120 to 160 rpm, 120 to 140 rpm, 150 to 300 rpm, 150 to 280 rpm, 150 to 260 rpm, 150 to 240 rpm, 150 to 220 rpm, 150 to 200 rpm, 150 to 180 rpm, 140 to 160 rpm, 200 to 300 rpm, 200 to 280 rpm, 200 to 260 rpm, 200 to 240 rpm, 200 to 220 rpm, or 100 to 150 rpm.

When the culture is performed in a medium including the lipophilic substance, the lipophilic substance is dispersed in the medium and comes in contact with the cells while stirring. When the lipophilic substance is dispersed in the medium, an area with which the microorganism is in contact increases, and retinoids may be efficiently isolated from the cells while culturing, and stabilized and/or dissolved.

Then, retinoids are isolated from a culture product of the microorganism.

When the microorganism is cultured in a culture medium in the presence of the lipophilic substance, isolation is performed from the lipophilic substance phase.

A method of isolating retinoids is not specifically limited, and may be performed by a method known in the related art. For example, centrifugation, filtration, crystallization, ion exchange chromatography, and high performance liquid chromatography (HPLC) may be used. Specifically, in order to obtain a high purity product after cells are isolated and then extracted using a solvent such as acetone, isolation and purification may be performed through HPLC or a crystallization operation.

The retinoids are widely used as sources of cosmetics, food or medicines.

Hereinafter, in order to specifically describe the present invention, examples will be described in detail.

Example 1-1. Preparation of Transformant of Saccharomyces Cerevisiae

In order to transform Saccharomyces cerevisiae to produce retinoids, first, retinoid producing genes of 6 types were introduced between a promoter and a terminator of a vector including the promoter and the terminator to prepare vectors of 6 types in which respective producing genes have a promoter and a terminator.

A polymerase chain reaction (PCR) was used to amplify genes having a GAL10 promoter and a GAL7 terminator from the recombinant vector. The amplified genes were sequentially introduced into an E. coli-Saccharomyces shuttle vector, and ultimately a recombinant shuttle vector for retinoid production was prepared.

The recombinant shuttle vector transformed the Saccharomyces cerevisiae to prepare a Saccharomyces transformant having retinoid productivity. This will be described in detail in the following sections.

(1) Preparation of Recombinant Shuttle Vector Including Genes Involved in Retinoid Production In order to transform Saccharomyces cerevisiae to have retinoid productivity, first, retinoid producing genes of 6 types were introduced between a promoter and a terminator of a vector including the promoter and the terminator to prepare vectors of 6 types in which these respective genes have a promoter and a terminator.

Information on genes of 6 types involved in retinoid production is shown in the following Table 1. Primers used to amplify a corresponding gene are shown in the following Table 2.

HMG1 genes were amplified from genomes of Saccharomyces cerevisiae using primers 1 and 2, cut with restriction enzymes EcoRI and SalI, and introduced into YEGα-HIR525 (KCTC 8519P, Choi et al., Appl. Microbial. biotechnol., 1994, 42, 587) treated with the same restriction enzymes to prepare a recombinant vector pGAL-HMG1.

crtE genes were amplified from genomes of Pantoea agglomerans using primers 3 and 4, cut with restriction enzymes EcoRI and SalI, and introduced into a YEGα-HIR525 vector treated with the same restriction enzymes to prepare pGAL-YEPAcrtE.

crtB genes were amplified from genomes of Pantoea agglomerans using primers 5 and 6, cut with restriction enzymes EcoRI and SalI, and introduced into a YEGα-HIR525 vector treated with the same restriction enzymes to prepare pGAL-YEPAcrtB.

crtI genes were amplified from genomes of Pantoea agglomerans using primers 7 and 8, cut with restriction enzymes EcoRI and SalI, and introduced into a YEGα-HIR525 vector treated with the same restriction enzymes to prepare pGAL-YEPAcrtI.

crtY genes were amplified from genomes of Pantoea ananatis using primers 9 and 10, cut with restriction enzymes EcoRI and SalI, and introduced into a YEGα-HIR525 vector treated with the same restriction enzymes to prepare pGAL-YEPAUcrtY.

SR genes were amplified from a pT-DHBSR recombinant plasmid vector (H J Jang et al, 2011, Microbial Cell Factories, 10:59) using primers 11 and 12, cut with restriction enzymes EcoRI and SalI, and introduced into a YEGα-HIR525 vector treated with the same restriction enzymes to prepare pGAL-YESYNSR.

TABLE 1

| SEQ ID NO | Gene name | Enzyme name | Reference or Genbank accession number |
|---|---|---|---|
| 1 | HMG1 | HMG-CoA reductase | 10-2009-0104505 |
| 2 | crtE | Geranylgeranyl pyrophosphate synthase | M87280 |
| 4 | crtB | Phytoene synthase | M87280 |
| 5 | crtI | Phytoene dehydrogenase | M87280 |
| 7 | crtY | Lycopene beta-cyclase | D90087 |
| 8 | SR | Beta carotene monooxygenase | HJ Jang et al, 2011, Microbial Cell Factories, 10:59 |

TABLE 2

| Primer number | Sequence (5'-3') | SEQ ID NO |
|---|---|---|
| 1 | GCGCGAATTCATGGACCAATTGGTGAAAACTGAAGTC | 49 |
| 2 | GCGCGTCGACTTTTAGGATTTAATGCAGGTGACGGAC | 50 |
| 3 | GCGCGAATTCAAAAATGGTGAGTGGCAGTAAAGCGG | 51 |
| 4 | GCGCGTCGACTTAGGCGATTTTCATGACCGGTG | 52 |
| 5 | GCGCGAATTCAAAAATGAGCCAACCGCCGCTG | 53 |
| 6 | GCGCGTCGACTTAAACGGGACGCTGCCAAAG | 54 |
| 7 | GCGCGAATTCAAAAATGAAAAAAACCGTTGTGATTGG | 55 |
| 8 | GCGCGTCGACTTATTGCAGATCCTCAATCATCAGG | 56 |
| 9 | GCGCGAATTCAAAAATGCAACCGCATTATGATCTGATTC | 57 |
| 10 | GCGCGTCGACTTAACGATGAGTCGTCATAATGGCTTG | 58 |
| 11 | GCGCGAATTCAAAAATGGGTCTGATGCTGATTGATTGG | 59 |
| 12 | GCGCGTCGACTTAGTTTTGATTTTGATACGGGAAGAG | 60 |

6 types of genes including the GAL10 promoter and the GAL7 terminator were amplified from the prepared recombinant plasmid vectors pGAL-YEPAcrtE, pGAL-HMG1, pGAL-YEPAcrtI, pGAL-YEPAcrtB, pGAL-YEPAUcrtY, and pGAL-YESYNSR using primers of the following Table 3, and were sequentially introduced into a YEGα-HIR525 shuttle vector used in the above.

More specifically, first, crtE genes including the GAL10 promoter and the GAL7 terminator were amplified from pGAL-YEPAcrtE using primers 13 and 14, cut with restriction enzymes KpnI and NotI, and then inserted into a YEGα-HIR525 shuttle vector cut with the same enzymes.

HMG1 genes including the GAL10 promoter and the GAL7 terminator were amplified from pGAL-HMG1 using primers 15 and 16, cut with restriction enzymes NotI and SpeI, and then inserted into the same restriction site of the prepared recombinant vector.

crtI genes including the GAL10 promoter and the GAL7 terminator were amplified from pGAL-YEPAcrtI using primers 17 and 18, cut with restriction enzymes EcoRV and NheI, and then inserted into the same restriction site of the prepared recombinant vector.

crtB genes including the GAL10 promoter and the GAL7 terminator were amplified from pGAL-YEPAcrtB using primers 19 and 20, cut with restriction enzymes NheI and BglII, and then inserted into the same restriction site of the prepared recombinant vector.

crtY genes including the GAL10 promoter and the GAL7 terminator were amplified from pGAL-YEPAUcrtY using primers 21 and 22, cut with restriction enzymes BamHI and PacI, and then inserted into the same restriction site of the prepared recombinant vector.

SR genes including the GAL10 promoter and the GAL7 terminator were amplified from pGAL-YESYNSR using primers 23 and 24, cut with restriction enzymes PacI and XbaI, and finally inserted into the same restriction site of the prepared recombinant vector to prepare a recombinant shuttle vector pGAL-EHIBYSR that is prepared to biosynthesize retinoids in *Saccharomyces*.

TABLE 3

| Primer number | Sequence (5'-3') | SEQ ID NO |
| --- | --- | --- |
| 13 | GCGCGCGGCCGCATCGCTTCGCTGATTAATTACCCC | 61 |
| 14 | GCGCACTAGTACAATGAGCCTTGCTGCAACATC | 62 |
| 15 | GCGCGGTACCATCGCTTCGCTGATTAATTACCCC | 63 |
| 16 | GCGCGCGGCCGCACAATGAGCCTTGCTGCAACATC | 64 |
| 17 | GCGCGATATCACTAGTATCGCTTCGCTGATTAATTACCCC | 65 |
| 18 | GCGCGCTAGCACAATGAGCCTTGCTGCAACATC | 66 |
| 19 | GCGCGCTAGCATCGCTTCGCTGATTAATTACCCC | 67 |
| 20 | GCGCAGATCTACAATGAGCCTTGCTGCAACATC | 68 |
| 21 | GCGCGGATCCATCGCTTCGCTGATTAATTAC | 69 |
| 22 | GCGCTTAATTAAACAATGAGCCTTGCTGCAACATC | 70 |
| 23 | GCGCTTAATTAAATCGCTTCGCTGATTAATTACCCC | 71 |
| 24 | GCGCTCTAGAGGGGAAACTTAAAGAAATTCTATTCTTG | 72 |

(2) Preparation of Transformant using Prepared Recombinant Shuttle Vector

*Saccharomyces cerevisiae* Y2805 strains were stirred in a 3 mL YPD (20 g of a peptone, 10 g of *Saccharomyces* extracts, and 20 g of glucose, per liter) medium at 30° C. and 250 rpm for a seed culture. The next day, a seed culture solution (0.5 mL) was inoculated into a 50 mL YPD medium and stirred at 30° C. and 180 rpm to perform a main culture for 3 hours.

The culture solution was centrifuged under conditions of 3,000 rpm and 4° C. for 5 minutes to remove a supernatant. Cells were washed with 25 mL of a 1×TE/0.1M LiAC buffer (10 mM Tris-HCl, 1 mM EDTA, 100 mM LiAC, and pH 7.5) once and then resuspended in 0.5 mL of the 1×TE/0.1 M LiAC buffer to prepare water-soluble cells (competent cells).

The prepared water-soluble cells (100 μl), the vector (5 μl), salmon sperm DNA (carrier DNA, Sigma D9156, USA) (5 μl) and PEG/LiAC (40% PEG3350 (Quiagen NeXtal Stock PEG3350 (200), Cat. No. 133083), 10 mM Tris-HCl, 1 mM EDTA, 100 mM LiAC, and pH 7.5) (0.6 mL) were mixed. The mixed solution was left for 30 minutes at 30° C., then added with 100 μl of DMSO, and mixed again. The prepared mixed cell solution was subjected to thermal shock treatment for 15 minutes at 42° C., cooled on ice for 5 minutes, centrifuged for 1 minute at 4° C., and then a supernatant was removed. Obtained pellets were resuspended in 200 μl of a TE buffer (10 mM Tris-HCl, 1 mM EDTA, and pH 7.5), smeared on a UD solid medium (6.7 g of Yeast nitrogen base without Amino Acids (Difco™, Cat. No. 291940), 0.77 g of −Ura DO Supplement (Clontech Cat. No. 630416), 20 g of dextrose, and 20 g of agar, per liter, and pH 5.8) serving as a selective medium, and cultured for 2 days at 30° C. to prepare a transformant.

Example 1-2. Production of Retinoids from *Saccharomyces* Transformant (1) Culture of *Saccharomyces* Transformant A single colony was inoculated into a UD medium (3 mL) and stirred at 30° C. and 250 rpm for a seed culture.

In a main culture, a YPDG medium (20 g of a peptone, 10 g of *Saccharomyces* extracts, 10 g of glucose and 10 g of galactose, per liter) including galactose was used as an experimental group. As a control group thereof, a YPD medium (20 g of a peptone, 10 g of *Saccharomyces* extracts, and 20 g of glucose per liter) including no galactose was used. In the culture, the YPDG medium and the YPD medium were dispensed at 25 mL into a 300 mL baffled flask, and then 5 mL of dodecane (Cat. No. 297879, Sigma, USA) was placed in 25 mL of the culture medium in a two-phase culture for retinoid production.

Initially cultured strains were inoculated at a cell concentration of 0.1 ($OD_{600\ nm}$) and cultured for 96 hours with stirring at 30° C. and 180 rpm. The cell growth was evaluated by measuring an optical density at 600 nm ($OD_{600\ nm}$) 72 hours after the culture.

(2) High Performance Liquid Chromatography (HPLC) Analysis of Retinoid

In the two-phase culture with a dodecane overlay, dodecane phases including retinoids were collected, centrifuged for 10 minutes at 14,000 rpm to remove all cell fragments, and then used for HPLC analysis. The dodecane phases were analyzed at a detection wavelength of 370 nm (retinal) and 340 nm (retinol and retinyl acetate) using HPLC (LC-20A, Shimadzu, Kyoto, Japan). The analysis was performed using an HPLC column of Symmetry C18 (250 mm×4.6 mm, 5 m) having Sentry Guard C18 (15 mm×4.6 mm, 5 m). Methanol and acetonitrile with a mobile-phase volume ratio of 95:5 were used. The HPLC analysis was performed under conditions of a mobile-phase flow rate of 1.0 ml/min and a column temperature of 40° C.

Retinal (Cat. No. R2500), retinol (Cat. No. R7632) and retinyl acetate (Cat. No. R4632) (commercially available from Sigma) were dissolved in acetone and used as standard compounds (FIG. 3(A)).

Figure 3:
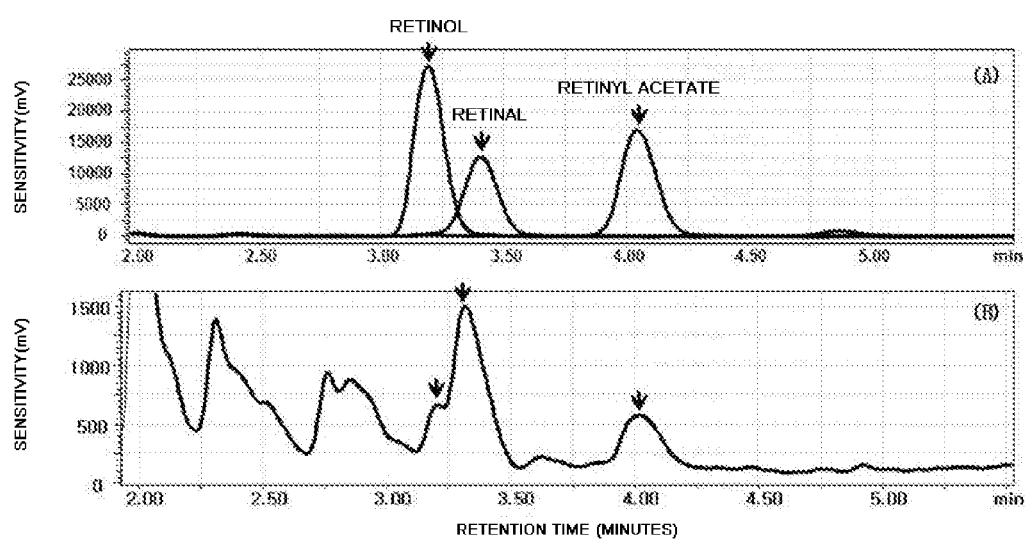
FIG. 3 shows HPLC peaks of retinoids produced through a retinoid standard compound (A) and *saccharomyces* (B).

As shown in FIG. 3, it can be seen that peaks of the retinoids (FIG. 3(B)) produced in the transformant are significantly shown at the same retention times as those of the retinol, the retinal and the retinal acetate (FIG. 3(A)) used as the standard compounds. Therefore, the retinoids produced in the transformant were determined as the same components as the retinoids serving as the standard compounds.

(3) Liquid Chromatography/Mass Spectrometry (LC-MS/MS) Analysis of Retinoids

In order to analyze the retinoid produced from the *Saccharomyces* transformant, liquid chromatography/mass spectrometry (LC-MS/MS) was performed.

Dodecane phases in the culture solution of the transformant were obtained, vacuum-evaporated, and dissolved in methanol having the same weight as the dodecane phases before evaporation. A component of the produced retinoids was analyzed using an ion trap mass spectrometer.

A Symmetry C18 (250 mm×4.6 mm, 5 m) column having Sentry Guard C18 (15 mm×4.6 mm, 5 m) and an AB SCIEX Qtrap 3200 (commercially available from AB SCIEX) serving as an analyzing device were used for LC-MS analysis. Methanol and acetonitrile with a mobile-phase volume ratio of 95:5 were used.

The HPLC analysis was performed under conditions of a mobile-phase flow rate of 1.0 ml/min and a column temperature of 30° C.

The retinol (Cat. No. R7632) and the retinyl acetate (Cat. No. R4632) (commercially available from Sigma) were dissolved in methanol and used as standard compounds.

Figure 4:
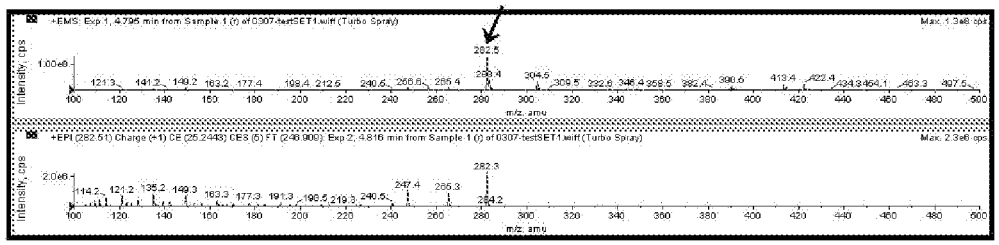
FIG. 4 shows LC-MS peaks of retinoid standard compounds (A and C) and retinoids (B and D) produced in *saccharomyces*.
Figure 4:
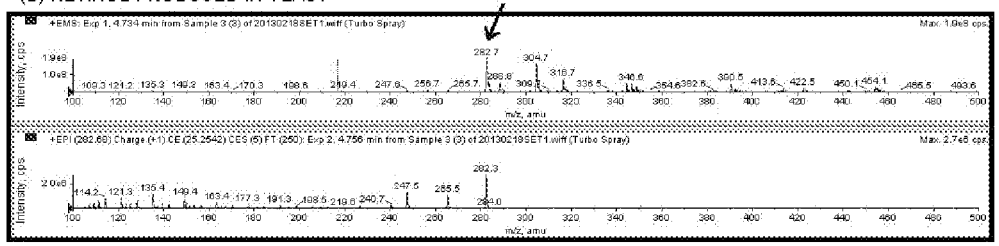
Figure 4:
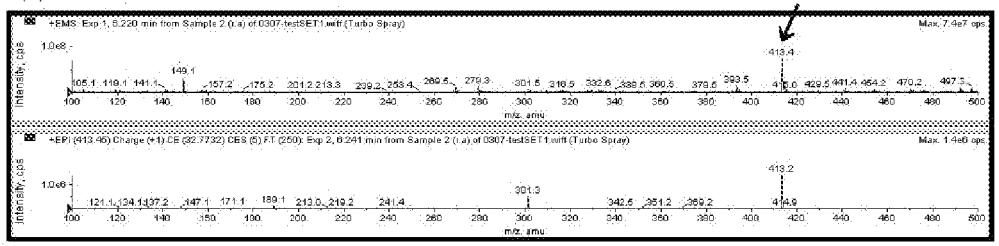
Figure 4:
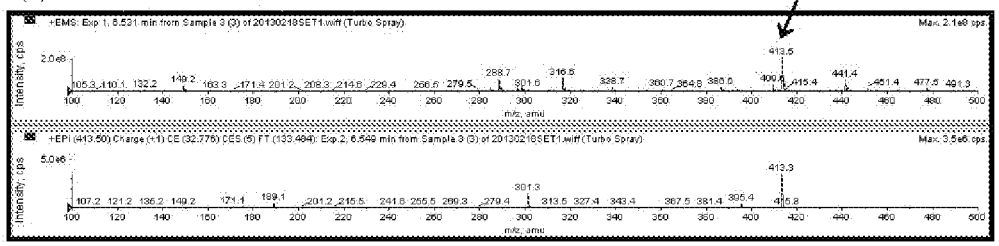

The analysis results are shown in FIG. 4.

As shown in FIG. 4, it can be seen that peaks of the retinoids (FIGS. 4(B) and 4(D)) produced in the transformant are significantly shown at the same retention times as those of the retinol (FIG. 4(A)) and the retinyl acetate (FIG. 4(C)) used as the standard compounds.

Therefore, it was confirmed that the retinoids produced in the transformant were determined as the same components as the retinoids serving as the standard compounds, and the microorganism of the present invention can effectively produce the retinoids.

(4) Culture Results

The culture results are shown in the following Table 4.

TABLE 4

| Classification | Cell concentration ($OD_{600\,nm}$) | Retinal (μg/L) | Retinol (μg/L) | Retinyl acetate (μg/L) |
|---|---|---|---|---|
| Experimental group | 22.76 ± 0.5 | 36 ± 0.67 | 2.8 ± 0.52 | 32.1 ± 2.6 |
| Control group | 18.6 ± 1.2 | 19.6 ± 0.96 | 1.49 ± 0.1 | 30.6 ± 0.98 |

As shown in Table 4, it can be seen that a cell concentration ($OD_{600\,nm}$) 72 hours after the culture was 22.8 in the experimental group that was cultured in the medium including galactose, which is greater than 18.6 of the control group that was cultured in the medium including no galactose.

In the experimental group, 36 μg/L of retinal, 2.8 μg/L of retinol, and 32.1 μg/L of retinyl acetate were produced, and retinoids totaling about 71 μg/L were produced. On the other hand, in the control group, 19.6 μg/L of retinal, 1.49 μg/L of retinol, and 30.6 μg/L of retinyl acetate were produced, and retinoids totaling about 51.7 μg/L were produced.

When a total amount of retinoid production of the transformant was divided by a cell concentration, the experimental group had a value of 3.11, and the control group had a value of 2.78. The experimental group had a higher value. It was confirmed that expression of enzymes involved in retinoid production was induced in the experimental group that was cultured in the medium including galactose.

Example 2-1. Preparation of *Corynebacterium* Transformant

Also, as described above, the transformant in which lycopene is accumulated, shuttle vectors including heterologously screened retinoid biosynthesis genes, crtE, crtB, crtI, idi, crtY, and BCMO were introduced to prepare a *Corynebacterium* transformant capable of producing retinoids. This will be described in detail in the following sections.

(1) Inactivation of Gene crtYe/f Coding Carotenoid-ε-Cyclase of *Corynebacterium Glutamicum*

In order to suppress decaprenoxanthin production and accumulate lycopene, the crtYe/f genes (group) coding amino acid sequences of SEQ ID NO 22 and SEQ ID NO 23 were inactivated.

In order to inactivate the crtYe/f genes, a suicide vector pK19mobsacB was used ("Handbook of *Corynebacterium glutamicum*", Lothar Eggeling et al, ISBN 0-8493-1821-1, 2005 by CRC press).

An upstream part 1036 bp of the crtYe/f gene was amplified using primers 25 and 26. A downstream part 1057 bp of the crtYe/f gene was amplified using primers 27 and 28.

Two amplified PCR products were used as a template, primers 25 and 28 were used to perform PCR amplification, the crtYe/f gene was deleted, and a PCR product having a linker sequence of 21 bp and a length of 2102 bp was obtained. The obtained 2102 bp product was cut with HindIII and SbfI and inserted into the same site of the vector pK19mobsacB to prepare a recombinant suicide vector pK19mobsacB-KOY.

The prepared recombinant vector transformed *Corynebacterium glutamicum* ATCC13032 by a method described in Handbook of *Corynebacterium glutamicum*.

A method of deleting a specific gene site through two-step homologous recombination has been reported in "Handbook of *Corynebacterium glutamicum*" (published in 2005 by CRC press).

First recombination occurred when the pK19mobsacB-KOY plasmid prepared above transformed *Corynebacterium* for deletion. In this case, a vector sequence was inserted (integrated) into a genome, which can be screened through kanamycin resistance. Since a strain having a genome into which the recombinant vector is inserted generates levansurase by sacB genes, it shows sensitivity in 10% sucrose. Also, when the first recombinant is subjected to PCR amplification using primers 29 and 30 of the following Table 5, recombination can be determined again if PCR products having sizes of 169 bp and 987 bp are obtained.

The recombinant vector for gene deletion was removed through second recombination, which was screened as having resistance to sucrose. More specifically, in order to perform the second recombination, the first recombinant was inoculated into a 5 ml BHI medium (12.5 g of calf brains, 5 g of beef heart, 10 g of a peptone, 5 g of sodium chloride, 2 g of glucose, and 2.5 g of sodium dihydrogen phosphate, per liter), stirred at 30° C. and 250 rpm, and cultured for 12 hours.

The culture solution was diluted to $10^{-3}$, $10^{-4}$, and $10^{-5}$ of the original concentration using the BHI medium, 100 μl of each was smeared on an LB (10 g of a tryptone, 5 g of Saccharomyces extracts and 10 g of sodium chloride per liter) agar plate including 10% sucrose and cultured for 3 days at 30° C. to obtain a colony. When the second recombinant was subjected to PCR amplification using primers 29 and 30, recombination can be determined again if a PCR product of 169 bp is obtained. This clone was susceptible to kanamycin at 20 μg/ml and did not grow, and ultimately ΔcrtYe/f strains in which the crtYe/f gene of Corynebacterium glutamicum ATCC 13032 was inactivated were prepared.

TABLE 5

| Primer number | Sequence (5'-3') | SEQ ID NO |
|---|---|---|
| 25 | ATAAAGCTTCTTCCTGTCTTCCCGACCCACTAC | 73 |
| 26 | CCCATCCACTAAACTTAAACAAATTTAATGATCGTATGAGGTCTTTTGAGATG | 74 |
| 27 | TGTTTAAGTTTAGTGGATGGGTCATGATGGAAAAAATAAGACTAATTCTATTGTC | 75 |
| 28 | AAACCTGCAGGTGATTCTGTTTTGGTTACTCATCCCG | 76 |
| 29 | ACTGCCCGAACCATTGCCG | 77 |
| 30 | AGGCCAGACCAAAGGGGTAGGC | 78 |

(2) Preparation of Recombinant Shuttle Vector Including Genes Involved in Retinoid Production In order to express a retinoid producing gene group in Corynebacterium glutamicum, a pSGT208 shuttle vector into which a terminator and a promoter were inserted was prepared based on an E. coli-Corynebacterium shuttle vector pCES208 (J. Microbiol. Biotechnol., 18:639-647, 2008).

More specifically, in order to insert the terminator, genes were amplified from a pTrc99A vector using primers 31 and 32, cut with restriction enzymes HindIII and ClaI, and inserted into a pSTV28 (Takara biotech) vector cut with the same restriction enzymes. In order to easily perform a promoter screening process, a lac promoter including a restriction site and a lacZ alpha fragment were inserted into the recombinant plasmid. In this case, the lacZ alpha fragment was designed to function as an identifier by introducing X-gal when the promoter is replaced.

The lac promoter and the lacZ alpha fragment were amplified from genomes of E. coli using primers 33 and 34, cut with restriction enzymes NgoMIV and EcoRI, and then inserted into the same restriction enzyme site of the prepared recombinant plasmid. A pSGT208 shuttle vector was prepared such that ScaI and ClaI were used for cutting from the recombinant plasmid prepared above, Klenow fragment enzymes were treated to prepare a blunt terminal, and the terminal was cut with restriction enzymes NotI and KpnI, and then inserted into the pCES208 shuttle vector that has generated the blunt terminal.

The pSGT208 shuttle vector has a replication origin of E. coli and Corynebacterium, has kanamycin-resistant genes, a multi-cloning site, and includes a lacZ alpha fragment identifier and a terminator in order to easily replace the promoter. Information on the primers used is shown in Table 6.

TABLE 6

| Primer number | Sequence (5'-3') | SEQ ID NO |
|---|---|---|
| 31 | GCTAAGCTTGGCTGTTTTGGCGGATGAGAG | 79 |
| 32 | CGAATCGATAGAGTTTGTAGAAACGCAAAAAGGCC | 80 |
| 33 | GCTGCCGGCAGATCTCATATGCCAATACGCAAACCGCCTCTC | 81 |
| 34 | GCTGAATTCACTAGTGCGGCCGCTTATTCGCCATTCAGGCTGCGC | 82 |

(3) Preparation of Transformant using Prepared Recombinant Shuttle Vector

Genes of 6 types involved in retinoid synthesis shown in the following Table 7 were sequentially introduced into the prepared E. coli-Corynebacterium shuttle vector pSGT208 using primers shown in Table 8.

More specifically, crtE genes were amplified from genomes of Synechocystis sp. PCC6803 using primers 35 and 36, cut with restriction enzymes SpeI and XhoI, and then inserted into the same site of a pSGT208 shuttle vector.

Next, crtI genes were amplified from genomes of Phodopseudomonas palustris using primers 37 and 38, cut with XhoI and NheI, and sequentially inserted into the same restriction site of the prepared recombinant vector.

Next, crtB genes were amplified from genomes of Pantoea agglomerans using primers 39 and 40, cut with NheI and XbaI, and sequentially inserted into the same site of the prepared recombinant vector.

Next, idi genes were amplified from genomes of Cronobacter sakazakii using primers 41 and 42, cut with XbaI and NotI, and then sequentially inserted into the same site of the prepared recombinant vector.

Next, crtY genes were amplified from genomes of Pantoea ananatis using primers 43 and 44, cut with SalI and StuI, and sequentially inserted into the same site of the prepared recombinant vector.

Finally, SR genes were amplified from pT-DHBSR using primers 45 and 46, cut with StuI and SbfI, inserted into the same site of the prepared recombinant vector, and a recombinant shuttle vector pS208-RET in which retinoid producing genes were sequentially completely included was completed.

TABLE 7

| SEQ ID NO | Gene name | Enzyme name | Reference or Genbank accession number |
|---|---|---|---|
| 3 | crtE | Geranylgeranyl pyrophosphate (GGPP) synthase | slr0739, GI: 16329282 |
| 4 | crtB | Phytoene synthase | M87280 |
| 6 | crtI | Phytoene dehydrogenase | RPA1512, GI: 39934584 |

TABLE 7-continued

| SEQ ID NO | Gene name | Enzyme name | Reference or Genbank accession number |
|---|---|---|---|
| 9 | idi | IPP isomerase | ESA_00346, GI: 156932565 |
| 7 | crtY | Lycopene-beta-cyclase | D90087 |
| 8 | SR | Beta carotene monooxygenase | HJ Jang et al, 2011, Microbial Cell Factories, 10:59 |

TABLE 8

| Primer number | Sequence (5'-3') | SEQ ID NO |
|---|---|---|
| 35 | CATACTAGTAGGAGGTAATAAATATGGTTGCCCAACAAACACGA | 83 |
| 36 | CGGCTCGAGTTAATATTTTCTGGCAACAATATATTCGGCG | 84 |
| 37 | GCTCTCGAGGAGGTAATAAATATGCTCGATCCTGGCCCCAATC | 85 |
| 38 | GCAGCTAGCTTATGATGTCACCAGACTGTCGGCCTC | 86 |
| 39 | GCAGCTAGCAGGAGGTAATAAATATGAGCCAACCGCCGCTGC | 87 |
| 40 | CTCCTCTAGATTACTAAACGGGACGCTGC | 88 |
| 41 | CCATCTAGAGGAGGTAATAAAATATGAAGGACAAGGAACTGAGC | 89 |
| 42 | CGTGCGGCCGCTTATTCCTCATCCCCGACGCGC | 90 |
| 43 | CGGTCGACAGGAGGTAATAAATATGCAACCGCATTATGATCTGATTCTC | 91 |
| 44 | CGCCTGCAGGAGGCCTTTAACGATGAGTCGTCATAATGGCTTG | 92 |
| 45 | CGAGGCCTAGGAGGTAATAAATATGGGTCTGATGCTGATTGATTGGTG | 93 |
| 46 | CGCCTGCAGGTTAGTTTTGATTTTGATACGGGAAGAGTG | 94 |

*Corynebacterium glutamicum* ATCC13032ΔcrtYe/f, which is recombinant *Corynebacterium glutamicum* in which crtYe and crtYf coding carotenoid epsilon-cyclase used to prepare the prepared recombinant shuttle vector pS208-RET were inactivated, was transformed by a method described in Handbook of *Corynebacterium glutamicum*.

Example 2-2. Production of Retinoids from *Corynebacterium* Transformant (1) Culture of *Corynebacterium* Transformant A single colony was inoculated into 3 mL of a 2YT medium, and stirred at 30° C. and 250 rpm for a seed culture. In a main culture, 20 μg/mL of the antibiotic kanamycin was used in a defined minimal medium (1 g of $K_2HPO_4$, 10 g of $(NH_4)_2SO_4$, 0.4 g of $MgSO_4 7H_2O$, 20 mg of $FeSO_4 7H_2O$, 20 mg of $MnSO_4 H_2O$, 50 mg of sodium chloride, 2 g of urea, 0.1 mg of biotin and 0.1 mg of thiamine, per liter). The culture was performed in a baffled flask including a 25 mL medium while stirring at 180 rpm and 30° C.

In a two-phase culture of retinoid production, 10 mL of heavy mineral oil (Cat. No. 5658-4400, Daejung Chemicals and Metals Co., LTD, Korea) was placed on 25 mL of a culture medium.

The cell growth was measured at an optical density of 600 nm ($OD_{600}$).

(2) High Performance Liquid Chromatography (HPLC) Analysis of Retinoids

In a two-phase culture having a heavy mineral oil layer, heavy mineral oil including retinoid was collected and centrifuged for 10 minutes at 14,000 rpm to remove all remaining cell fragments and water-soluble substances. Then, retinoids of the isolated heavy mineral oil layer were extracted using acetone for 15 minutes at room temperature, centrifuged for 10 minutes at 14,000 rpm to remove all heavy mineral oil phases, and then acetone extracts were used for analysis.

The acetone extracts including retinoids were analyzed at a detection wavelength of 370 nm (retinal) and 340 nm (retinol and retinyl acetate) using HPLC (LC-20A, Shimadzu, Kyoto, Japan).

The analysis was performed using an HPLC column of Symmetry C18 (250 mm×4.6 mm, 5 m) having Sentry Guard C18 (15 mm×4.6 mm, 5 m). Methanol and acetonitrile with a mobile-phase volume ratio of 95:5 were used. The HPLC analysis was performed under conditions in which a mobile-phase flow rate of 1.5 ml/min and a column temperature of 40° C.

Retinal (Cat. No. R2500), retinol (Cat. No. R7632) and retinyl acetate (Cat. No. R4632) (commercially available from Sigma) were dissolved in acetone and used as standard compounds (FIG. 5(A)).

Figure 5:
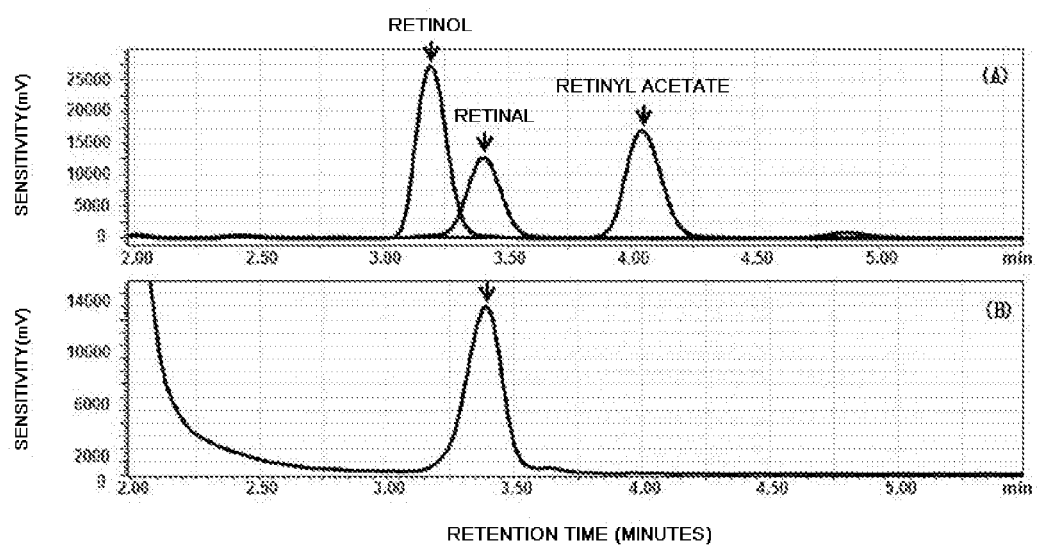
FIG. 5 shows HPLC peaks of retinoids produced through a retinoid standard compound (A) and *corynebacterium* (B).

As shown in FIG. 5, it can be seen that a peak of the retinoid produced in the transformant (FIG. 5(B)) is significantly shown at the same retention time as that of the retinal (FIG. 3(A)) used as the standard compound. Therefore, the retinoid produced in the transformant was determined as the same component as the retinal serving as the standard compound.

(3) Culture Result

The culture results are shown in the following Table 9.

TABLE 9

| Classification | Vector | Cell concentration ($OD_{600\ nm}$) | Retinal (μg/L) | Retinol (μg/L) | Retinyl acetate (μg/L) |
|---|---|---|---|---|---|
| Example | pS208-RET | 14.9 ± 2.9 | 3277.87 ± 134.79 | — | — |
| Comparative Example | pSGT208 | 9.5 ± 0.5 | — | — | — |

As shown in Table 9, it can be seen that a cell concentration ($OD_{600\ nm}$) 48 hours after the culture was 15 in the transformant including genes coding enzymes involved in retinoid production of the Example, which is greater than 9.5 of the Comparative Example in which only a shuttle vector including no genes coding enzymes involved in retinoid production was introduced.

In the Example, about 3,278 μg/L of retinal was produced. However, no retinal was produced in the comparative example.

The invention claimed is:

1. A microorganism of the genus *Saccharomyces*, comprising genes coding enzymes involved in retinoid production.

2. The microorganism according to claim 1, wherein the genes code at least one amino acid sequence selected from the group consisting of SEQ ID NOs 1 to 9.

3. The microorganism according to claim 1, wherein the genes code an amino acid sequence of at least one of SEQ ID NOs 2, 3 and 10; at least one of SEQ ID NOs 4 and 11; at least one of SEQ ID NOs 5, 6 and 12; SEQ ID NO 7; SEQ ID NO 8; and at least one of SEQ ID NOs 9, 13 and 21.

4. The microorganism according to claim 3, further comprising a gene coding an amino acid sequence of SEQ ID NO 1.

5. The microorganism according to claim 1, wherein the microorganism is *Saccharomyces cerevisiae*.

6. The microorganism according to claim 1, wherein the microorganism is *Saccharomyces cerevisiae* Y2805.

7. A microorganism (the genus *Corynebacterium*) comprising genes coding enzymes involved in retinoid production.

8. The microorganism according to claim 7, wherein the genes code at least one amino acid sequence selected from the group consisting of SEQ ID NOs 2 to 9.

9. The microorganism according to claim 7, wherein the genes code an amino acid sequence of at least one of SEQ ID NOs 2, 3 and 10; at least one of SEQ ID NOs 4 and 11; at least one of SEQ ID NOs 5, 6 and 12; SEQ ID NO 7; SEQ ID NO 8; and at least one of SEQ ID NOs 9, 13 and 21.

10. The microorganism according to claim 9, further comprising a gene coding at least one amino acid sequence of SEQ ID NOs 14 and 15.

11. The microorganism according to claim 9, further comprising a gene coding an amino acid sequence of SEQ ID NOs 16 to 20.

12. The microorganism according to claim 7, wherein, in the microorganism, a gene coding at least one amino acid sequence selected from the group consisting of SEQ ID NOs 22 to 24 is inactivated or deleted.

13. The microorganism according to claim 7, wherein the microorganism is *Corynebacterium glutamicum*.

14. The microorganism according to claim 7, wherein the microorganism is *Corynebacterium glutamicum* ATCC13032.

15. The microorganism according to claim 1, wherein the gene is introduced by a vector.

16. The microorganism of claim 1, wherein the microorganism is transformed with a gene encoding a hydroxymethylglutaryl(HMG)-CoA reductase among enzymes in a MVA pathway, and the microorganism has retinoid producing efficacy without being transformed with genes encoding acetyl-CoA acetyltransferase, HMG-CoA synthase, mevalonate kinase, phosphomevalonate kinase, diphosphomevalonate decarboxylase, or isopentenyl diphosphate isomerase in an MVA pathway.

* * * * *